US009796991B2

(12) United States Patent
Wen et al.

(10) Patent No.: US 9,796,991 B2
(45) Date of Patent: Oct. 24, 2017

(54) RECOMBINANT STRAIN PRODUCING L-AMINO ACIDS, CONSTRUCTING METHOD THEREFOR AND METHOD FOR PRODUCING L-AMINO ACIDS

(71) Applicant: INSTITUTE OF MICROBIOLOGY, CHINESE ACADEMY OF SCIENCES, Beijing (CN)

(72) Inventors: Tingyi Wen, Beijing (CN); Xiuling Shang, Beijing (CN); Yun Zhang, Beijing (CN); Shuwen Liu, Beijing (CN); Yong Liang, Beijing (CN); Yu Zhang, Beijing (CN)

(73) Assignee: INSTITUTE OF MICROBIOLOGY, CHINESE ACADEMY OF SCIENCES, Beijing (CN)

(*) Notice: Subject to any disclaimer, the term of this patent is extended or adjusted under 35 U.S.C. 154(b) by 46 days.

(21) Appl. No.: 14/891,622

(22) PCT Filed: Feb. 4, 2015

(86) PCT No.: PCT/CN2015/072220

§ 371 (c)(1),
(2) Date: Nov. 16, 2015

(87) PCT Pub. No.: WO2015/120775

PCT Pub. Date: Aug. 20, 2015

(65) Prior Publication Data

US 2016/0326556 A1 Nov. 10, 2016

(30) Foreign Application Priority Data

Feb. 14, 2014 (CN) .......................... 2014 1 0050868

(51) Int. Cl.

| | |
|---|---|
| ***C12P 13/04*** | (2006.01) |
| ***C12P 13/24*** | (2006.01) |
| ***C12N 9/04*** | (2006.01) |
| ***C12N 9/92*** | (2006.01) |
| ***C12N 15/77*** | (2006.01) |

(52) U.S. Cl.

CPC ............ *C12P 13/24* (2013.01); *C12N 9/0006* (2013.01); *C12N 9/92* (2013.01); *C12N 15/77* (2013.01); *C12Y 101/01043* (2013.01); *C12Y 101/01049* (2013.01); *C12Y 503/01009* (2013.01)

(58) Field of Classification Search

CPC ................................ C12P 13/24; C12N 9/006
USPC .............................................. 435/106, 252.3
See application file for complete search history.

(56) References Cited

U.S. PATENT DOCUMENTS

| | | | |
|---|---|---|---|
| 7,504,242 B2 | 3/2009 | Dunican | |
| 8,993,272 B2 | 3/2015 | Kim | |
| 2003/0138917 A1 | 7/2003 | Dunican et al. | |
| 2005/0079586 A1 | 4/2005 | Ikeda et al. | |
| 2007/0026505 A1 | 2/2007 | Madden et al. | |
| 2008/0032374 A1 | 2/2008 | Zelder et al. | |
| 2008/0268502 A1 | 10/2008 | Haefner et al. | |
| 2009/0137010 A1 | 5/2009 | Shakulov et al. | |

FOREIGN PATENT DOCUMENTS

| | | | |
|---|---|---|---|
| CN | 1317049 A | * | 10/2001 |
| CN | 1317049 A | | 10/2001 |
| CN | 101029310 A | | 9/2007 |
| CN | 102549144 A | | 7/2012 |
| CN | 102676509 A | | 9/2012 |
| EP | 1087015 A2 | | 3/2001 |
| EP | 2107128 A2 | | 10/2009 |
| EP | 2107128 A3 | | 10/2009 |
| JP | 2001136988 | | 5/2001 |
| JP | 2003-504065 | | 2/2003 |
| JP | 2008-523834 | | 7/2008 |
| JP | 2008-259505 | | 10/2008 |
| JP | 2009-501512 | | 1/2009 |
| JP | 2009-112300 A | | 5/2009 |
| JP | 2011-518571 | | 6/2011 |
| WO | WO 0170995 A1 | | 9/2001 |
| WO | WO03/048351 | | 6/2003 |
| WO | WO2009133114 | | 11/2009 |

OTHER PUBLICATIONS

Written Opinion (English translation) filed in PCT/CN2015/072220 (2015).*

Zhang, Yun et al., "Genetic and biochemical characterization of Corynebacterium glutamicum ATP phosphoribosyltransferase and its three mutants resistant to feedback inhibition by histidine", Biochimie, vol. 94, No. 3, Mar. 31, 2012 (Mar. 31, 2012), ISSN: 0300-9084, pp. 829-839.

Allen, S. et al., "Metabolic Flux in Both the Purine Mononucleotide and Histidine Biosynthetic Pathways Can Influence Synthesis of the Hydroxymethyl Pyrimidine Moiety of Thiamine in *Salmonella enterica*", Journal of Bacteriology, vol. 184, No. 22, Nov. 30, 2002 (Nov. 30, 2002), ISSN: 0021-9193, pp. 6130-6137.

Zhang, Yun et al., "Development and Application of an Arabinose-Inducible Expression System by Facilitating Inducer Uptake in Corynebacterium glutamicum", Applied and Environmental Microbiology, vol. 78, No. 16, Aug. 31, 2012 (Aug. 31, 2012), ISSN: 0099-2240, pp. 5831-5838.

(Continued)

*Primary Examiner* — Tekchand Saidha

(74) *Attorney, Agent, or Firm* — Howard IP Law Office, PA

(57) ABSTRACT

The present invention relates to recombinant bacteria producing L-amino acid, in which the recombinant bacteria has reduced expression of the glucose-6-phosphate isomerase gene pgi and improved expression of the glucose-6-phosphate dehydrogenase gene -opcA than the starting bacteria, where the starting bacterium is a bacterial strain that can accumulate target amino acid(s) and preferably, the amino acid is L-histidine.

20 Claims, 2 Drawing Sheets

(56) References Cited

OTHER PUBLICATIONS

International Search Report for PCT/CN2015/072220.
Biotechnol Lett, 2013, vol. 35, pp. 735-741.
Microbial Biotechnology, 2014, 1, vol. 7, No. 1, pp. 5-25.
Biochimie, 2012, vol. 94, pp. 829-838.
Journal of Bacteriology, 1988, vol. 170, No. 3, pp. 1148-1152.
Applied and Environmental Microbiology, 2012, vol. 78, No. 16, pp. 5831-5838.
NCBI [online], 2009, Sep. 23, 2016, URL, https://www.ncbi.nlm.nih.gov/nuccore/42602314?from=1585600&to=1586445.
NCBI [online], 2009, Sep. 23, 2016, URL, https://www.ncbi.nlm.nih.gov/nuccore/42602314?from=997463&to=998440.
FEMS Microbiology Reviews, 2005, vol. 29, pp. 555-590.
NCBI [online], 2009, Sep. 23, 2016, URL, https://www.ncbi.nlm.nih.gov/nuccore/42602314?from=919967&to=921529.

* cited by examiner

RECOMBINANT STRAIN PRODUCING L-AMINO ACIDS, CONSTRUCTING METHOD THEREFOR AND METHOD FOR PRODUCING L-AMINO ACIDS

The present application claims priority from PCT Application No. PCT/CN2015/072220, filed on Feb. 4, 2015 which claims priority from CN 201410050868.2, filed on Feb. 14, 2014, the entirety of each is incorporated herein by reference.

TECHNOLOGICAL FIELD

The present invention relates to the field of microbialfermentation, specifically to a method of producing L-amino acid(s) through microbial fermentation and its special-purposerecombinant bacteria.

BACKGROUND OF THE INVENTION

Microbial fermentation is the method applied most widely to produce L-amino acid(s). The bacteria performance of producing amino acid(s) through fermentation is the key factor affecting whether the fermentation method can be applied at a large scale of industrialization. At present, there are still a few amino acids that are not realized to produce through the fermentation method due to absence of the production bacterial strain(s) with good fermentation performance. Moreover, as for the bacterial strains producing amino acids which have been realized to produce through the fermentation method, the amino acid tilter and yield from glucose still need to be improved in order to save production cost. For example, L-histidine is the ninth amino acid necessary to human and animal life. It plays the role in the fundamental physiological processes such as body growth and development, oxidation resistance and immunoregulation and is an important amino acid for medical purpose. It can be used in infusion preparations for heart disease, anemia and gastrointestinal ulcer. Now L-histidine is mainly produced through the method of protein hydrolysis and extraction with pigs (cow) blood powder as the raw material. However, this method has the drawbacks such as high cost, low utilization of raw materials, complex extraction process and serious environmental pollution resulting in high production cost and high price. Nevertheless, the method of producing L-histidine through microbiological fermentation hasnot been applied at a large scale of industrialization. The bio-synthesis of L-histidine is featured in competing the precursor substances with nucleotide synthesis, complex metabolic regulation mechanism and high energy demand during synthesis process. Thus, the L-histidine production and yield of engineering bacteria are relatively low. The bacterial strains producing L-histidine are mainly bred through the methods of several rounds of traditional mutation-screening and genetic engineering on the basis of mutant strains. However, the strains produced from mutation-screening can accumulate a large amount of negative-effect mutation, resulting in slow growth of strains, reduced environmental tolerance and increased nutrients demand. Therefore, these drawbacks limit the industrial application of strains. Till now, there is only one report about the study of modifying and constructing L-histidine engineering bacteria through systems metabolic engineering (Doroshenko, V. G., Lobanov, A. O., Fedorina, E. A., 2013. The directed modification of *Escherichia coli* MG1655 to obtain histidine-producing mutants, Appl Biochem Microbiol. 49, 130-135.). This study uses the wild type of *E. coli* MG1655 as the starting bacteria and introduced E271K mutation into the gene hisG to weaken the feedback inhibitory regulation of histidine; knocks out the transcription attenuator hisL of the synthetic operon of histidine and enhanced the expression of the synthetic operon of histidine; also knocks out the gene purR and increased the synthesis of histidine synthetic precursor PRPP to construct a strain of engineering bacteria producing L-histidine. This study only modifies the terminal synthetic pathway of L-histidine and the yield of L-histidine is only 4.9 g/L. Thus, it is far from the realization of industrial application.

The L-histidine bio-synthesis is derived from the pentose phosphate pathway. When the glucose is used as the carbon source, the precursor for L-histidine synthesis-phosphoribosyl pyrophosphate (PRPP) is produced from the pentose phosphate pathway and PRPP simultaneously enters the synthetic pathway of nucleotide and the synthetic pathway of L-histidine where the former produces another precursor ATP for L-histidine synthesis.

In addition, the pentose phosphate pathway is also the main path forming cofactor(s) NADPH necessary to the synthesis of many amino acids (such as L-lysine, L-valine, L-threonine, L-proline, L-hydroxyproline), wherein: 4 molecules of NADPH are consumed to synthesize one molecule of L-lysine, 3 molecules of NADPH for 1 molecule of L-threonine, L-proline or L-hydroxyproline, and 2 molecules of NADPH for 1 molecule of L-valine.

The glucose-6-phosphate isomerase of the glycolytic pathway can be inactivated to guide the carbon metabolic flow to the pentose phosphate pathway. However, it will result in weakened growth of bacterial strains and glucose metabolism ability; hence, it is unfavorable for the application of bacterial strains in fermentation production (Marx, A., Hans, S., Mockel, B., Bathe, B., de Graaf, A. A., McCormack, A. C., Stapleton, C., Burke, K., O'Donohue, M., Dunican, L. K., 2003. Metabolic phenotype of phosphoglucose isomerase mutants of *Corynebacterium glutamicum*. J Biotechnol. 104, 185-197.). The results of previous studies by the inventor verified that: knocking out the encoding gene pgi of the glucose-6-phosphate isomerase resulted in serious degradation of strain growth and glucose metabolic ability and also decrease of the yield of L-histidine accordingly. Moreover, the inventor also found that it was not effective to improve the yield of L-histidine only through improving the expression of the glucose-6-phosphate dehydrogenase.

SUMMARY OF THE INVENTION

The purpose of the present invention is to provide a recombinant bacteria, its construction method and the method of producing L-amino acid(s) with said recombinant bacteria, which can improve the yield of L-amino acid(s), especially L-amino acid(s) synthesized with the precursor substances or the cofactor NADPH provided by the pentose phosphate pathway, such as L-histidine.

Thus, on one hand, the present invention will provide a recombinant bacteira of producing L-amino acid(s), wherein: said recombinant bacteria has reduced expression of glucose-6-phosphate isomerase Pgi and improved expression of the glucose-6-phosphate dehydrogenase Zwf-OpcA than the starting bacteria, where said starting bacterium is a bacterial strain that can accumulate target amino acid(s).

According to one implementation way, said starting bacterium is obtained through mutation or genetic engineering modification on original bacteria. In order to obtain the target amino acid(s), said starting bacteria can be either the existing bacterial strain(s) which can accumulate target amino acid(s) or the bacterial strain(s) which can accumulate target amino acid(s) obtained through genetic engineering modification on appropriate original bacteria. In order to obtain a high-yield engineering bacteria, the bacterial strain(s) with higher yield of target amino acid(s) is selected as the starting bacteria.

The target amino acid(s) mentioned in the present invention refers to the L-amino acid(s) synthesized from the precursor substance(s) or the cofactor NADPH provided from the pentose phosphate pathway. Preferably, said amino acid(s) is L-histidine.

According to one implementation way, said recombinant bacteria can have weakened expression of the gene pgi and enhanced expression of the gene zwf-opcA than the starting bacteria. Specifically, the gene pgi on the chromosome of said recombinant bacterium is inactivated and preferably knocked out or the regulatory element of the gene pgi is replaced by that with low transcription or low expression activity. Simultaneously, said recombinant bacteria has two or more copied genes zwf-opcA or the promoter of the operon tkt-tal-zwf-opcA-devB is replaced with a strong promoter, for example, the promoter $P_{eftu}$ of the original bacteria.

As for the recombinant bacteria producing L-histidine, its starting bacteria can have enhanced expression of the gene hisEG and the gene hisDCB of the operon for L-histidine synthesis than the original bacteria. Specifically, a strong promoter can be used to replace the promoter of said gene. For example, the promoter $P_{glyA}$ on the chromosome of the original bacterium is used to replace respectively the promoters of hisEG and hisDCB on the chromosome of the original bacteria. Further preferably, said starting bacteria can have enhanced expression of the PRPP synthetase PrsA than the original bacteria. More preferably, said starting bacteria has two or more copied genes prsA or a strong promoter is used to replace the promoter of the gene prsA, for example, the promoter $P_{sod}$ of the original bacteria can be used to replace the promoter of the geneprsA.

As for the recombinant bacteria producing L-histidine, according to one preferred implementation way, said recombinant bacteria can increase the expression of AICAR transmethylase/IMP ring hydrase PurH than said starting bacteria. Preferably, said recombinant bacteria have two or more copied genespurH or a strong promoter is used to replace the promoter of the gene purH. For example, the promoter $P_{eftu}$ of said original bacterium is used to replace the promoter of the gene purH.

According to one more preferable implementation way, said recombinant bacteria has weakened expression of the amidophosphoribosyl transterase PurF than said starting bacteria. Specifically, a weak promoter can be used to replace the promoter of the genepurF. Preferably, on the chromosome of said recombinant bacteria, the promoter $P_{hom}$ in said original bacterium is used to replace the promoter of the genepurF.

In spite that the implementation ways above provide the examples of strong promoter, the present invention exercises no special limit on it and any one can be feasible as long as the expression of the promoted gene can be enhanced. The strong promoters that can be used in the present invention can be $P_{eftu}$, $P_{sod}$, $P_{glyA}$, $P_{pck}$ and $P_{pgk}$ of the original bacteria in spite of no limitation to them.

Said original bacterium is preferred to be a bacterial strain selected from *corynebacterium*, *dialister* or *brevibacterium*. The bacteria of said *corynebacterium* is preferred to a bacterial strain selected from *Corynebacterium glutamicum*, *Corynebacterium pekinense*, *Corynebacterium efficiens*, *Corynebacterium crenatum*, *Corynebacterium thermoaminogenes*, *Corynebacterium aminogenes*, *Corynebacterium lilium*, *Corynebacterium callunae* and *Corynebacterium herculis*. The bacteria of said *dialister* are preferred to be a bacterial strain selected from *Microbacterium ammoniaphilum*. The bacteria of said *brevibacterium* are preferred to be a bacterial strain selected from *Brevibacteriaceae flvum*, *Brevibacteriaceae lactofermentum*, *Brevibacteriaceae ammoniagenes*.

According to one specific implementation way, said original bacterium is a wild type of *Corynebacterium glutamicum* ATCC13032.

In this case, for the recombinant bacteria producing L-histidine, the chromosome of said starting bacteria has the promoter $P_{glyA}$ as shown by No. 863-1038 nucleotide sequence of 5' end in SEQ ID NO: 7 used to replace respectively the promoters of the operon hisEG and hisDCB for L-histidine synthesis on the chromosome of said *Corynebacterium glutamicum* ATCC13032 and said starting bacteria can express a mutated ATP-phosphoribosyl transferase(s).

Said mutated ATP-phosphoribosyl transferase is the enzyme to mutate No. 215 asparagine of ATP-phosphoribosyl transferase as shown by SEQ ID NO: 6 to lysine, No. 231 leucine to phenylalanine and No. 235 threonine to alanine. Preferably, the chromosome of said starting bacteria has the gene $hisG^{fbr}$ as shown by No. 1007-1852 nucleotide sequence in SEQ ID NO: 4 used to replace the gene hisG on the chromosome of said *Corynebacterium glutamicum* ATCC13032.

According to one preferred implementation way, the chromosome of said starting bacteria has the promoter $P_{sod}$ as shown by No. 656-847 nucleotide sequence of 5' end in SEQ ID NO: 11 used to replace the promoter of the gene prsA on the chromosome of said *Corynebacterium glutamicum* ATCC13032.

According to another preferred implementation way, said starting bacteria has two or more copied genes prsA and $hisG^{fbr}$. Said gene prsA can be selected from the gene coding for PrsA as shown by the SEQ ID NO: 5; and one of the genes whose codes are at least 60% homologous with said PrsA, or preferably at least 70% homologous, more preferably at least 80% homologous, further preferably at least 95% homologous, or even further preferably at least 98% homologous or even 99% homologous and with PrsA activity. Specifically, it can be No. 15-992 nucleotide sequence as shown by SEQ ID NO: 4 in the sequence table.

In the recombinant bacteria according to the present invention, said gene pgi can be selected from the gene coding for Pgi as shown by SEQ ID NO: 14 in the code sequence table; and one of the genes whose codes are at least 60% homologous with said Pgi, or preferably at least 70% homologous, more preferably at least 80% homologous, further preferably at least 95% homologous, or even further preferably at least 98% homologous or even 99% homologous and with the activity of said glucose-6-phosphate isomerase Pgi. Specifically, it can be the nucleotide sequence as shown by SEQ ID NO: 13.

Said gene zwf-opcAcan be selected from the gene of Zwf-OpcA as shown by SEQ ID NO: 3 in the code sequence table; and one of the genes whose codes are at least 60% homologous with said Zwf-OpcA, or preferably at least 70% homologous, more preferably at least 80% homologous, further preferably at least 95% homologous, or even further preferably at least 98% homologous or even 99% homologous and with the activity of said Zwf-OpcA. Specifically, it can be the nucleotide sequence as shown by SEQ ID NO: 2.

Said promoter $P_{eftu}$ can be No. 635-834 nucleotide sequence of 5' end as shown by SEQ ID NO: 12.

Said gene purH can be selected from the gene coding for PurH as shown by SEQ ID NO: 16 in the code sequence table; and one of the genes whose codes are at least 60% homologous with said PurH, or preferably at least 70% homologous, more preferably at least 80% homologous, further preferably at least 95% homologous, or even further preferably at least 98% homologous or even 99% homologous and with the activity of said PurH, preferably, said gene purH can be the nucleotide sequence as shown by SEQ ID NO: 15 in the sequence table.

Said promoter $P_{hom}$ can be No. 736-865 nucleotide sequence of 5' end in SEQ ID NO: 18.

In the recombinant bacteria according to the present invention, a recombinant plasmid(s) containing some gene(s) can be introduced to increase the copy number of this gene or some gene(s) can be inserted directly on the appropriate locus(s) of the strain chromosome. There is no limitation on the vector used to construct the recombinant plasmid and it can be any appropriate one, for example pXMJ19.

According to the second aspect of the present invention, a method of constructing recombinant bacteria producing L-amino acid(s) is provided. Said method comprises the following steps: reduce the expression of the glucose-6-phosphate isomerase Pgi in the starting bacteria and enhance the expression of the glucose-6-phosphate dehydrogenase Zwf-OpcA in said starting bacteria to obtain said recombinant bacteria, where said starting bacterium is a strain(s) which can accumulate target amino acid(s).

The starting bacteria can be obtained through the known methods such as mutation or genetic engineering modification and an existing bacterial strain which can produce target amino acid(s) can be used as the starting bacteria. It is preferred to use those high-yield bacterial strains.

The target amino acid(s) mentioned in the present invention is preferably L-histidine. According to one implementation way, reducing the expression of Pgi in starting bacterium is realized by means of the following A) or B):

A) Inactivate the gene pgi of the chromosome of said starting bacteria; said inactivation is preferably knocking out;

B) Replace the regulatory element of the gene pgi in said starting bacteria with a regulation element with low transcription or low expression activity.

Said increasing the expression of Zwf-OpcA in said starting bacterium is realized by means of the following C) or D):

C) Increase the copy number of the gene zwf-opcA in said starting bacteria;

D) Replace the promoter of the operton tkt-tal-zwf-opcA-devB on the chromosome of said starting bacteria with a strong promoter, for example, the $P_{eftu}$ promoter on the chromosome of said original bacteria.

As for L-histidine, according to one implementation way, obtaining said starting bacteria can comprise the step(s) of replacing respectively the promoters of the operon hisEG and hisDCB for L-histidine synthesis on the chromosome of the original bacteria with a strong promoter, for example, the promoter $P_{glyA}$ on the chromosome of said original bacteria. Further preferably, obtaining said starting bacteria can further comprise the step(s) of increasing the expression of PRPP synthetase PrsA in said starting bacteria. More preferably, said increasing the expression of PrsA in said starting bacterium is realized by means of the following means of E) or F):

E) Increase the copy number of the gene prsA in said starting bacteria;

F) Replace the promoter of the gene prsA on the chromosome of said starting bacteria with a strong promoter, for example, the promoter $P_{sod}$ on the chromosome of said original bacteria.

According to one preferred implementation way, as for L-histidine, said method can further comprise the step(s) of improving the expression of AICAR transmethylase/IMP ring hydrase PurH in said recombinant bacteria. Preferably, said improving the expression of PurH in said recombinant bacteria can be realized by means of the following G) or H):

G) Increase the copy number of the gene purl-fin said starting bacteria;

H) Replace the promoter of the gene purH on the chromosome of said starting bacteria with a strong promoter, for example, the promoter $P_{eftu}$ on the chromosome of said original bacteria.

According to more preferred implementation way, as for L-histidine, said method can further comprise the step(s) of weakening the expression of the amidophosphoribosyl transterase PurF in said recombinant bacteria. Specifically, a weak promoter can be used to replace the promoter of the gene purF. Preferably, said weakening the expression of PurF in said recombinant bacterium is realized through replacing the promoter of the gene purF on the chromosome in said starting bacteria with the promoter $P_{hom}$ on the chromosome in said original bacteria.

Similarly, there is no special limitation on the strong promoter, and any one can be feasible which can enhance the expression of the promoted gene. The promoter can be $P_{eftu}$, $P_{sod}$, $P_{glyA}$, $P_{pck}$ and $P_{pgk}$ of the original bacteria in spite of no any limitation to them. Preferably, the bacterial strain that can be used as the original bacteria can be a bacterial strain selected from *corynebacterium, dialister* or *brevibacterium*. The bacteria of said *corynebacterium* is preferred to a bacterial strain selected from *Corynebacterium glutamicum, Corynebacterium pekinense, Corynebacterium efficiens, Corynebacterium crenatum, Corynebacterium thermoaminogenes, Corynebacterium aminogenes, Corynebacterium lilium, Corynebacterium callunae* and *Corynebacterium herculis*. The bacteria of said *dialister* are preferred to be a bacterial strain selected from *Microbacterium ammoniaphilum*. The bacteria of said *brevibacterium* are preferred to be a bacterial strain selected from *Brevibacteriaceae flvum, Brevibacteriaceae lactofermentum, Brevibacteriaceae ammoniagenes*. The most preferred one is *Corynebacterium glutamicum* or *Brevibacteriaceae flvum.*

According to one implementation way, the original bacterium is the wild type of *Corynebacterium glutamicum* ATCC13032.

As for this implementation way and the recombinant bacteria producing L-histidine, said starting bacteria can be obtained through the following recombination and modification on the starting bacteria:

Replace the promoters of the operon hisEG and hisDCB for L-histidine synthesis on the chromosome of said *corynebacterium glutamicum* ATCC13032 with the promoter $P_{glyA}$ as shown by No. 863-1038 nucleotide sequence of 5' end in SEQ ID NO: 7 (or No. 752-927 nucleotide sequence of 5' end in SEQ ID NO: 8) and As for ATP-phosphoribosyl transferase as shown by SEQ ID NO: 6 expressed by said *Corynebacterium glutamicum* ATCC13032, mutate its No. 215 asparagine to lysine, No.

231 leucine to phenylalanine and No. 235 threonine to alanine. The gene of said mutation above is the gene $hisG^{fbr}$ as shown by No. 1007-1852 nucleotide sequence in SEQ ID NO: 4.

According to one implementation way, in order to obtain starting bacteria with better performance of accumulating L-histidine, the chromosome of said *Corynebacterium glutamicum* ATCC13032 is further modified and the promoter of the gene prsA on the chromosome is replaced with the promoter $P_{sod}$ as shown by No. 656-847 nucleotide sequence of 5' end in SEQ ID NO: 11.

According to another preferred implementation way, the starting bacteria with better performance to accumulate L-histidine can be obtained through increasing the copy number of the gene prsA in said *Corynebacterium glutamicum* ATCC13032 and increasing the copy number of the gene $hisG^{fbr}$ in said *corynebacterium glutamicum* ATCC13032.

Said gene prsA can be selected from the gene coding for PrsA as shown by the code SEQ ID NO: 5; and one of the genes whose codes are at least 60% homologous with said PrsA, or preferably at least 70% homologous, more preferably at least 80% homologous, further to preferably at least 95% homologous, or even further preferably at least 98% homologous or even 99% homologous and with the activity of PrsA. Specifically, it can be No. 15-992 nucleotide sequence as shown by SEQ ID NO: 4 in the sequence table.

Said gene pgi can be selected from the gene coding for Pgi as shown by the code SEQ ID NO: 14; and one of the genes whose codes are at least 60% homologous with said Pgi, or preferably at least 70% homologous, more preferably at least 80% homologous, further preferably at least 95% homologous, or even further preferably at least 98% homologous or even 99% homologous and with the activity of said glucose-6-phosphate isomerase. Specifically, it can be the nucleotide sequence as shown by SEQ ID NO: 13.

Said gene zwf-opcAcan be selected from the gene of Zwf-OpcA as shown by SEQ ID NO: 3 in the code sequence table; and one of the genes whose codes are at least 60% homologous with said Zwf-OpcA, or preferably at least 70% homologous, more preferably at least 80% homologous, further preferably at least 95% homologous, or even further preferably at least 98% homologous or even 99% homologous and with the activity of said Zwf-OpcA. Specifically, it can be the nucleotide sequence as shown by SEQ ID NO: 2.

Said promoter $P_{eftu}$ is No. 635-834 nucleotide sequence of 5' end as shown by SEQ ID NO: 12(or No. 634-833 of 5' end as shown by SEQ ID NO: 20).

Said gene purH can be selected from the gene of PurH as shown by SEQ ID NO: 16 in the code sequence table; and one of the genes whose codes are at least 60% homologous with said PurH, or preferably at least 70% homologous, more preferably at least 80% homologous, further preferably at least 95% homologous, or even further preferably at least 98% homologous or even 99% homologous and with the activity of said PurH. Specifically, it can be the nucleotide sequence as shown by SEQ ID NO: 15.

Said promoter $P_{hom}$ can be No. 736-865 nucleotide sequence of 5' end by SEQ ID NO: 18.

In the methods according to the present invention, increasing the copy number of some gene(s) can be realized through constructing recombinant plasmid(s) containing the gene(s) and then introducing the recombinant plasmid(s) into the starting bacteria/original bacteria. These methods are commonly applied in the art and will not be repeated here. There is no limitation on the vector used to construct the recombinant plasmid and it can be any appropriate one, for example pXMJ19.

The recombinant bacteria according to the present invention can be obtained through the construction method as above.

According the third aspect of the present invention, a method of producing L-amino acid(s) is provided comprising the steps of fermenting and culturing the recombinant bacteria as above. Said L-amino acid is preferably L-histidine.

The method of constructing recombinant bacteria according to the present invention comprises the following steps: reduce the expression of the glucose-6-phosphate isomerase in the starting bacteria and enhance the expression of glucose-6-phosphate dehydrogenase and PRPP synthetase in said starting bacteria, so as to obtain the recombinant bacteria.

In the method as above, said reducing the expression of the glucose-6-phosphate isomerase in the starting bacterium is realized by means of the following A) or B):

A) Inactivate the gene pgi of the chromosome of said starting bacteria; said inactivation is specifically knocking out;

B) Replace the regulatory element of the gene pgi in said starting bacteria with a regulatory element with low transcription and low expression activity;

said improving the expression of the glucose-6-phosphate dehydrogenase and PRPP synthetase in said starting bacterium is realized by means of the following C) or D):

C) Increase the copy number of the gene zwf-opcA and the gene prsA in said starting bacteria;

D) Replace the promoter of the operon tkt-tal-zwf-opcA-devB on the chromosome of said starting bacteria with a strong promoter and also replace the promoter of the gene prsA on the chromosome of said starting bacteria with the promoter $P_{sod}$.

In the method as above, said method of constructing recombinant bacterium is I or II as follows:

The method shown in Iis to knock out the gene pgi of the chromosome of said starting bacteria and increase the copy number of the gene zwf-opcA and the gene prsA in said starting bacteria so as to obtain the recombinant bacteria;

The method shown in II is to knock out the gene pgi of the chromosome of said starting bacteria and replace the promoter of the operon tkt-tal-zwf-opcA-devB on the chromosome of said starting bacteria with the promoter $P_{eftu}$ and also replace the promoter of the gene prsA on the chromosome of said starting bacteria with the promoter $P_{sod}$.

In the aforementioned method, said knocking-out is to introduce the segment containing the upstream and downstream homologous arm of the gene pgi into said starting bacteria to carry out homologous recombination;

Said increasing the copy numbers of the gene zwf-opcA and the gene prsA in said starting bacterium is to introduce the gene zwf-opcA and the segment prsA-$hisG^{fbr}$ into said starting bacteria via recombinant vector;

The aforementioned recombinant vector is the recombinant vector obtained through inserting the gene zwf-opcA and the segment prsA-$hisG^{fbr}$ into the expression vector; said expression vector can be an IPTG inducible expression vector pXMJ19.

In the embodiment 2 according to the present invention, the recombinant vector is pXMJ19-zwf-opcA-prsA-$hisG^{fbr}$, which is a vector obtained through inserting the gene zwf-opcA (SEQ ID NO: 2) between the loci of Hind III and Xba I of pXMJ19 and also inserting the segment prsA-his$G^{fbr}$(SEQ ID NO: 4) between the loci of Xba I and Sma I.

Said replacing the promoter of the operon tkt-tal-zwf-opcA-devB on the chromosome of said starting bacteria with the promoter $P_{eftu}$ is to introduce the segment containing the is promoter $P_{eftu}$ into said starting bacteria to carry out homologous recombination;

Said replacing the promoter of the gene prsA on the chromosome of said starting bacteria with the promoter $P_{sod}$ is to introduce the segment containing the promoter $P_{sod}$ into said starting bacteria to carry out homologous recombination.

In the aforementioned method, the nucleotide sequence of the segment containing the upstream and downstream homologous arm of said gene pgi to knock out is SEQ ID NO: 1 in the sequence table, where No. 1-834 nucleotide of 5' end in SEQ ID NO: 1 is the upstream homologous arm of the gene pgi to knock out, No. 835-1672 nucleotide of 5' end in SEQ ID NO: 1 is the downstream homologous arm of the gene pgi to knock out; the nucleotide sequence of the gene pgi is SEQ ID NO: 13; the nucleotide sequence of said gene zwf-opcA is SEQ ID NO: 2 in the sequence table; the nucleotide sequence of said segment prsA-his$G^{fbr}$ is SEQ ID NO: 4 in the sequence table;

said recombinant vector is the vector obtained through inserting said gene zwf-opcA and said segment prsA-his$G^{fbr}$ into the expression vector;

the nucleotide sequence of said promoter $P_{eftu}$ is No. 635-834 nucleotide of 5' end of SEQ ID NO: 12 in the sequence table;

the nucleotide sequence of said segment containing the promoter $P_{eftu}$ is SEQ ID NO: 12 in the sequence table;

the nucleotide sequence of said segment containing the promoter $P_{sod}$ is SEQ ID NO: 11 in the sequence table.

In the aforementioned method, said starting bacterium is prepared according to the method comprising the following steps: replace the promoter of the operon for L-histidine synthesis on the bacterial chromosome with the promoter $P_{glyA}$ and also carry out point mutation on the gene hisG on said bacterial chromosome so as to yield the starting bacteria;

Said operon for L-histidine synthesis is hisEG and hisDCB;

the nucleotide sequence of said promoter $P_{glyA}$ is No. 863-1038 nucleotide of SEQ ID NO: 7 in the sequence table or No. 752-927 nucleotide of SEQ ID NO: 8 in the sequence table;

Said point mutation is to mutate No. 215 asparagine of the protein encoded by the gene hisG of said bacterial chromosome to lysine, No. 231 leucine to phenylalanine and No. 235 threonine to alanine.

In the aforementioned method, said replacing the promoter of the operon for L-histidine synthesis on said bacterial chromosome with the promoter $P_{glyA}$ is to introduce the segment containing the promoter $P_{glyA}$ of hisEG and the segment containing the promoter $P_{glyA}$ of hisDCB into the bacteria to carry out homologous recombination, wherein: the nucleotide sequence of the segment containing the promoter $P_{glyA}$ of hisEG is SEQ ID NO: 7 in the sequence table, the nucleotide sequence of the segment containing the promoter $P_{glyA}$ of hisDCB is SEQ ID NO: 8 in the sequence table.

In the aforementioned method, said point mutation of the gene hisG on said bacterial chromosome is to introduce the nucleotide sequence as shown by SEQ ID NO: 9 into said bacteria to carry out homologous recombination and then introduce the nucleotide sequence as shown by SEQ ID NO: 10 into the intermediate bacteria to carry out homologous recombination.

In the aforementioned method, said bacterium is a bacteria of *corynebacterium* and said bacteria of *corynebacterium* is specifically *Corynebacterium glutamicum.*

The recombinant bacteria prepared according to the aforementioned method(s) is also protected by the scope of the present invention.

The application of the recombinant bacteria above in the preparation of L-histidine is also protected by the scope of the present invention.

The present invention also provides a method of preparing L-histidine which comprises the following step(s): ferment and culture the recombinant bacteria above to obtain L-histidine.

As for said gene pgi of the inactivated bacteria in the present invention, the "inactivation" refers to that the modified subject changes correspondingly to achieve some effect, including but not limited to site-directed mutation, insertional inactivation and/or knocking-out.

The methods of knocking-out, insertional inactivation, gene knocking-in, replacing promoter and site-directed mutation of chromosome gene used in the present invention are realized through homologous recombination of the homologous arms carrying the modifying target gene of suicide vector pK18mobsacB.

As for said L-histidine engineering bacteria in the present invention, the production intensity of L-histidine after fermentation for 24 hours is 0.01-1 g/Uh and the yield of L-histidine at completion of fermentation is 1-60 g/L. Generally, the yield of fermentation can amount to over 2 g/L.

The experiments of the present invention show that: the present invention has the following advantages compared with the existing L-histidine engineering bacteria and the existing fermentation production method(s) of L-histidine:

(1) The recombinant bacteria provided according to the present invention adopts a strategy of combinational modification through knocking out the gene pgi to block the upstream glycolytic pathway and simultaneously over-expressing the gene zwf-opcA to enhance the metabolic capacity of the pentose phosphate pathway, thus the growth of engineering bacteria and the consumption ability of glucose appear no obvious degradation compared with the wild type of bacterial stain and the yield of L-histidine increases obviously.

(2) The recombinant bacteria provided according to the present invention grows well in the basic medium (used in flask-shaking fermentation test) without any nutrient-defective phenotype and is easy for industrial control.

(3) The recombinant bacteria provided according to the present invention has short fermentation time and the highest accumulation can realize after about 45-72 hours during the scale-up experiment in a fermentation tank (versus the reported 120 hours of fermentation time by L-histidine engineering bacteria to realize the highest yield so far) (Mizukami, T., Hamu, A., Ikeda, M., Oka, T., Katsumata, R., 1994. Cloning of the ATP phosphoribosyl transferase gene of *Corynebacterium glutamicum* and application of the gene to 1-histidine production. Biosci. Biotechnol. Biochem. 58, 635-638.). It is easy to control the process and the cost.

(4) The present invention proposes for the first time a strategy of combinational modification to simultaneously enhance the expression of the glucose-6-phosphate dehydrogenase on the basis of pgi gene deletion. It removes the limitation of strain growth and glucose metabolism due to the pgi gene deletion and can guide the metabolic flux of central carbon to the pentose phosphate pathway as much as possible and simultaneously keep a relatively high growth metabolism and ATP level of the bacteria. Hence, the yield of amino acid(s) is improved obviously so as to be practically used in the industrial production of bacterial fermentation.

(5) The present invention also proposes, for the first time, a strategy of coupling the synthetic pathway of histidine and the synthetic pathway of nucleotide. It utilizes the is byproduct AICAR from histidine synthesis to synthesize the precursor ATP for histidine synthesis. Thus, the yield of L-histidine is improved obviously and hence can be practically used in the industrial production of L-histidine with bacterial fermentation.

From the above, the beneficial effects according to the present invention are that: a new method of improving the fermentation yield of L-histidine is developed and proved in practice, the corresponding engineering bacterium is constructed and it is observed that the yield can be improved through additive effect. Hence, it can be practically used to produce L-amino acid(s) with bacterial fermentation and be convenient to expand the application.

In order to facilitate understanding, the following embodiments will be introduced as follows to describe the present invention in detail. It is necessary to point out in particular that these descriptions are exemplary and do not constitute any limit on the scope of the present invention. According to the discussion in the specification, many changes, modifications on the present invention are obvious for those skilled in the art.

In addition, the present invention cites the published literatures. These literatures are used to describe the present invention more clearly and their full-contents are included in the present invention for reference and it is deemed as if their full contents are narrated in the present invention.

DESCRIPTION OF THE DRAWINGS

The following drawings can be referred to help understand the solution and the beneficial effects according to the present invention.

DETAILED DESCRIPTION OF EMBODIMENTS

Figure 1:
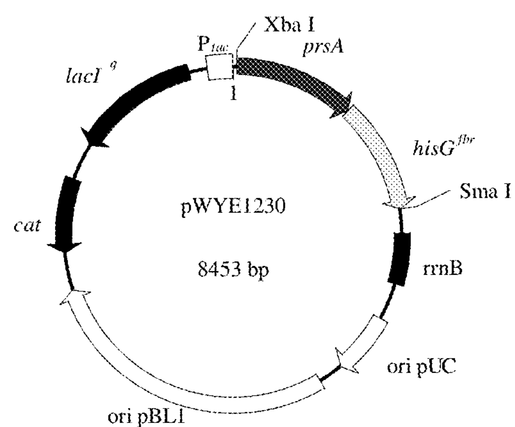
FIG. 1 is the schematic diagram of the recombinant plasmid pXMJ19-prsA-hisG$^{fbr}$.

The specific implementation ways according to the present invention are described in more detail in combination with the drawings and the embodiments in order to better understand the solution and the advantages in each aspect according to the present invention.

Nevertheless, the specific implementation ways and the embodiments described below are just for the purpose of explanation rather than any limit on the present invention. Specifically, all the following descriptions use (the wild type of) *Corynebacterium glutamicum* as the example to explain and test the construction of the recombinant engineering bacteria and the production of L-histidine. Nevertheless, those skilled in the art may easily understand that the modification strategy to the metabolic pathway of amino acid according to the present invention can be used to other appropriate bacterial strains in order to construct the engineering bacteria to improve the yield of L-histidine.

As mentioned in the background technologies, the glucose-6-phosphate isomerase encoded by the gene pgi is the key enzyme of the glycolytic pathway. The precursor PRPP for L-histidine synthesis is synthesized from the pentose phosphate pathway. Thus, it is assumed that knocking out the gene pgi will weaken the metabolic flux of the glycolytic pathway and guide the metabolic flux of central carbon to the pentose phosphate pathway so as to enhance the metabolic flux of L-histidine synthesis pathway. The strategy of modification through knocking out the gene pgito enhance the metabolic flux of the pentose phosphate pathway has been reported in both literature and patents (used to produce the products such as L-lysine, L-valine and nucleoside. Marx, A., Hans, S., Mockel, B., Bathe, B., de Graaf, A. A., McCormack, A. C., Stapleton, C., Burke, K., O'Donohue, M., Dunican, L. K., 2003. Metabolic phenotype of phosphoglucose isomerase mutants of *Corynebacterium glutamicum*. J Biotechnol. 104, 185-197; Blombach, B., Schreiner, M. E., Bartek, T., Oldiges, M., Eikmanns, B. J., 2008. *Corynebacterium glutamicum* tailored for high-yield I-valine production. Appl Microbiol Biotechnol. 79, 471-479; Peifer, S., Barduhn, T., Zimmet, S., Volmer, D., Heinzle, E., Schneider, K., 2012. Metabolic engineering of the purine biosynthetic pathway in *Corynebacterium glutamicum* results in increased intracellular pool sizes of IMP and hypoxanthine. Microb Cell Fact. 11, 138; U.S. Pat. No. 6,586,214B1; EP1087015A2).

However, in fact, after the studies by the inventor, it is found that: knocking out the gene pgi can result in over accumulation of intermediate metabolites of sugar metabolism and sugar metabolic stress and hence cause slow glucose metabolism and growth of bacteria. The inventor also finds that: after the gene pgi is knocked out, the yield of L-histidine produced by the engineering bacteria producing L-histidine is clearly reduced, instead of increasing. The main reason is that: the histidine obtains the precursor to synthesize its molecular skeleton through the pentose phosphate pathway whereas the lysine and the valine acquire the cofactor NADPH of their synthetase through the pentose phosphate pathway. In addition, the synthesis process of histidine needs to consume a large number of energy carriers ATP. Thus, if the strategy of increasing the histidine yield through weakening the expression of the gene pgi and enhancing the metabolic flux of the pentose phosphate pathway is to be adopted, the balance of metabolic fluxes between the pentose phosphate pathway and the glycolytic pathway needs to be kept in order to ensure the synthetic precursor and the energy supply.

In regard to such problems, the present invention finds through the experiments that the over-expression of the gene zwf-opcA (this gene encodes the glucose-6-phosphate dehydrogenase and is the key rate-limiting enzyme of the pentose phosphate pathway) can enhance the ability of bacteria to metabolize sugar, relieve sugar metabolic stress and restore the ability of glucose metabolism and growth of bacteria as well as balance the metabolic fluxes between the pentose phosphate pathway and the glycolytic pathway and balance the supplies of the precursors PRPP and ATP for histidine synthesis so as to hence improve the yield of L-histidine.

According to the present invention, with the modification strategy of weakening (such as knocking out) the gene pgi and simultaneously over-expression of the gene zwf-opcA, the bacterial strains of which the expression of the gene prsA and the expression of the operon gene for L-histidine synthesis are enhanced are recombined and modified to obtain the strain(s) which successfully improves the yield of L-histidine.

The strategy of modification through both weakening the gene pgi and over-expression of the gene zwf-opcA according to the present invention can increase NADPH and also balance the metabolic fluxes between the pentose phosphate pathway and the glycolytic pathway, can smooth away the problems of slow glucose metabolism and growth of bacteria due to weakening of the gene pgi and hence can also improve further the yield of amino acids.

On this basis, the present invention further proposes a strategy to couple the synthetic pathway of L-histidine and the synthetic pathway of nucleotide. During the synthetic process of L-histidine, the imidazole glycerol phosphate synthase encoded by the genes hisH and hisF catalyzes and produces the imidazole glycerol phosphate and the 5-phosphoribosyl-4-formamido-5-aminoimidazole(AICAR), wherein: the former finally synthesizes L-histidine along the synthetic pathway of histidine, but the latter can enter the purine synthetic pathway and finally produce the purine nucleotides (AMP, ATP, etc.). ATP is one of the precursor substances to synthesize histidine and also provides energy for histidine synthesis. The bi-functional enzyme encoded by the gene purH, AICAR transmethylase/IMP ring hydrase, catalyzes two steps of reaction from AICAR to produce IMP. The inventor finds that enhancing the expression of the gene purH in *Corynebacterium glutamicum* can facilitate obviously the accumulation of L-histidine and can further enhance the effect in combination with the above modification strategy.

Moreover, the synthetic pathway of L-histidine and the synthetic pathway of purine nucleotide couple with each other at the metabolite AICAR and use the same precursor substance PRPP. The inventor finds that weakening the encoding gene purF of the enzyme (amidophosphoribosyl transterase) for the first reaction step catalyzing the synthesis of purine nucleotide can conduct the metabolic coupling between the synthetic pathway of nucleotide and the synthetic pathway of histidine, synthesize nucleotide from the by-product AICAR of histidine synthesis, increase the supply of the precursor substance PRPP for histidine synthesis and simultaneously promote the metabolic flux of the synthetic pathway of histidine so as to facilitate the accumulation of L-histidine. Such gene modification can also improve further the yield of L-histidine.

As described above, the present invention can recombine and modify several target spots in the pathways related to histidine synthesis of microorganism and effectively realize the accumulation of L-histidine. In addition to modifying the synthetic pathway of histidine, the synthetic pathway of histidine and the synthetic pathway of nucleotide are coupled to effectively utilize the coupling node AICAR of histidine synthesis and nucleotide synthesis to form a pathway of purine nucleotide and save the synthetic precursor PRPP so as to provide more precursor substances PRPP and ATP for histidine synthesis and further increase the accumulation of L-histidine.

Definitions

The term "starting bacteria" mentioned in this article (also referred to as "base bacteria" in this article) refers to the initial bacterial strain used in the strategy of gene modification according to the present invention. This strain can be naturally occurring or bred by means of mutation or genetic engineering modification. In order to construct the engineering bacteria used to produce some L-amino acid (for example, L-histidine), said starting bacterium is preferred to a bacterial strain which can accumulate this L-amino acid (for example, L-histidine).

The term "original bacteria" mentioned in this article refers to bacterial strain which is not ever modified at all through any genetic engineering. It can be naturally occurring or bred by means of artificial mutation.

The term "homology" mentioned in this article refers to the level of similarity between different nucleotide sequences of DNA or different amino acid sequences of protein. Also, the DNAs and their encoded proteins with (some degree of) homology mentioned in this article shall have the same or better activity at least when used in the function(s) according to the present invention. Similarly, the proteins with (some degree of) homology shall have the same or better activity at least when used in the function(s) according to the present invention. For example, the gene hisG has high similarity with the gene $hisG^{fbr}$ obtained through mutation on three loci, wherein: the former encodes the ATP-phosphoribosyl transferase and the latter encodes the ATP-phosphoribosyl transferase of which the feedback inhibitory regulation of histidine is removed. These two enzymes are somewhat different in functions and activities as a whole, but they are the same in the function of "the catalyzing enzyme for the first step of reaction of histidine synthesis" according to the present invention. Thus, the gene hisG and the gene $hisG^{fbr}$ as well as the enzymes encoded by them are DNAs and proteins with homology meaningfully according to the present invention. They are all covered by the protection scope of the present invention.

The execution order of various steps of the methods mentioned in this article, unless otherwise specified, is not limited to those reflected by the text of this article. That is, the execution order of various steps can be subject to change and other step(s) can be inserted between any two steps as necessary.

Below the specific embodiments will be used to further describe the present invention. Unless otherwise specified, the experiment methods used in the following embodiments are all conventional methods. Unless otherwise specified, the materials, reagents, etc used in the following embodiments can all be obtained commercially.

Unless otherwise specified, the technological means employed in the embodiments are the conventional means well known by those skilled in the art. Please see "Molecular Cloning: A Laboratory Method (Rev. 3)" (China Science Press), "Microbiology Experiment (Rev. 4)" (China Higher Education Press) as well as the manufacturer's instructions of corresponding instruments and reagents, etc. The instruments, equipments and reagents used in the embodiments are commonly sold in the market. The quantitative tests in the following embodiments are all repeated three times to calculate the average value for the result.

Embodiment 1: Obtaining L-Histidine Base Engineering Bacteria CG160

Based on the previous studies by the inventor, this embodiment carries out the modification of enhancing histidine synthesis to the wild type of *Corynebacterium glutamicum ATCC*13032 so as to obtain the base bacteria of the aforementioned multi-target modification according to the present invention. First, replace the promoter of hisEG and hisDCB (two operons of histidine synthetic gene) with the endogenous strong promoter $P_{glyA}$ of *Corynebacterium glutamicum* (as shown by No. 863-1038 nucleotide sequence of 5' end in SEQ ID NO: 7 or as shown by No. 752-927 nucleotide sequence of 5' end in SEQ ID NO: 8) (Zhang, Y., Shang, X., Lai, S., Zhang, G., Liang, Y., Wen, T., 2012. Development and application of an arabinose-inducible expression aystem by facilitating inducer uptake in *Corynebacterium glutamicum*. Appl Environ Microbiol. 78, 5831-5838.). Simultaneously, replace the ribosome binding site (RBS) of the genes hisEand hisD with the conserved RBS sequence (AAAGGAGGA) of the highly expressed gene of *Corynebacterium glutamicum* (as shown by No. 1039-1047 nucleotide sequence of 5' end in SEQ ID NO: 7 or as shown by No. 928-936 nucleotide sequence of 5' end in SEQ ID NO: 8), so as to remove the weakening regulation of transcription and translation of the two operons of histidine synthesis genes, and replace the initiation codon GTG of the gene hisE with ATG (as shown by No. 1053-1055 nucleotide sequence of 5' end in SEQ ID NO: 7) to enhance its expression. Second, replace the encoding gene hisG of the key rate-limiting enzyme ATP-phosphoribosyl transferase (HisG as shown by SEQ ID NO: 6) of the histidine synthesis pathway with the gene $hisG^{fbr}$ containing three loci of amino acid mutation (as shown by No. 1007-1852 nucleotide sequence of 5' end in SEQ ID NO: 4), so as to remove the feedback inhibitory regulation of histidine to this enzyme and enhance the catalytic activity of this enzyme (Zhang, Y., Shang, X., Deng, A., Chai, X., Lai, S., Zhang, G., Wen, T., 2012. Genetic and biochemical characterization of *Corynebacterium glutamicum* ATP phosphoribosyl transferase and its three mutants resistant to feedback inhibition by histidine. Biochimie. 94, 829-838.).

1.1 Replace the Promoter of the Operon for L-Histidine Synthesis in the Wild Type of *Corynebacterium glutamicu* ATCC13032 with the Strong Promoter $P_{glyA}$ The primers are designed separately according to the operon hisEG of *Corynebacterium glutamicu* ATCC13032 in Genbank, its upstream and downstream sequences and the $P_{glyA}$ promoter sequence.

With the genome DNA of *Corynebacterium glutamicu* ATCC13032 as the template and P1 and P2 as the primers, the upstream homologous arm of the promoter of the hisEG operon is amplified through PCR; the promoter $P_{glyA}$ is amplified with P3 and P4 as the primers; the downstream homologous arm of the promoter hisEG is amplified with P5 nd P6 as the primers. Then the PCR product above is purified and used as the template, the technique of overlap extension PCR (SOE) is employed with P1 and P6 as the primers to carry out amplification and obtain PCR product of 1920 bp. It is the segment (SEQ ID NO: 7) containing the replacing promoter $P_{glyA}$ and the upstream and downstream homologous arms of the replaced promoter $P_{glyA}$, wherein: No. 1-862 nucleotides of 5' end in SEQ ID NO: 7 is the upstream homologous arm of the replaced promoter $P_{hisEG}$, No. 863-1038 nucleotides of 5' end in SEQ ID NO: 7 is the promoter $P_{glyA}$, No. 1053-1920 nucleotides of 5' end in SEQ ID NO: 7 is the downstream homologous arm of the replaced promoter $P_{hisEG}$.

After double-enzyme digestion by Xba I and BamH I, the PCR product of 1920 bp as above connects with the homologous recombinant vector pK18mobsacB (purchased from American Type Culture Collection-ATCC, product number: 87097) after the same double-enzyme digestion. The connection product is transformed through chemical method into *Escherichia coli* DH5α and the transformant is screened on LB plate containing Kanamycin (50 μg/mL). Then, after the transformant is sub-cultured three generations, P13 and P14 are used as the primers and the colony PCR is employed to identify the transformant and then obtain 2132 bp being the positive transformant. The plasmid of the transformant after identified is extracted and identified through double-enzyme digestion by Xba I and BamH I to obtain 1920 bp being positive.

The positive plasmid is sequenced and the result shows it is the recombinant plasmid obtained after the nucleotide as shown by SEQ ID NO: 7 in the sequence table is inserted into the vector pK18mobsacB and named as pK18mobsacB-$P_{glyA}$::$P_{hisEG}$.

The same method is employed to construct the homologous recombinant plasmid pK18mobsacB-$P_{glyA}$::$P_{hisDCB}$ with the specific requirements as follows: P7 and P8 are used as the primers to amplify the upstream homologous arm of the promoter of the operon hisDCB; P9 and P10 are used as the primers to amplify the promoter $P_{glyA}$; P11 and P12 are used as the primers to amplify the downstream homologous arm of the promoter of hisDCB. P7 and P12 are used as the primers and the technique of overlap extension PCR (SOE) is employed to carry out amplification. The PCR product of 1694 bp is obtained. It is the long segment (SEQ ID NO: 8) containing the replacing promoter $P_{glyA}$ and the upstream and downstream homologous arms of the replaced promoter $P_{hisDCB}$, wherein: No. 1-751 nucleotides of 5' end in SEQ ID NO: 8 is the upstream homologous arm of the replaced promoter $P_{hisDCB}$, No. 752-927 nucleotides of 5' end of SEQ ID NO: 8 is the promoter $P_{glyA}$, No. 942-1694 nucleotides of 5' end of SEQ ID NO: 8 is the downstream homologous arm of the replaced promoter $P_{hisDCB}$.

After double-enzyme digestion by Hind III and BamH I, the PCR product of 1694 bp as above connects with the homologous recombinant vector pK18mobsacB after the same double-enzyme digestion. The connection product is transformed through chemical method into *Escherichia coli* DH5α and the transformant is screened on LB plate containing Kanamycin (50 μg/mL). After the transformant is sub-cultured three generations, P13 and P14 are used as the primers and the colony PCR is employed to identify the transformant with 1906 bp being the positive transformant. The plasmid of the transformant after identified is extracted and identified through double-enzyme digestion by Hind III and BamH I to obtain 1694 bp being positive. The positive plasmid is sequenced and the result shows it is the recombinant plasmid obtained after the nucleotide as shown by SEQ ID NO: 5 in the sequence table is inserted into the vector pK18mobsacB and named as pK18mobsacB-$P_{glyA}$::$P_{hisDCB}$.

The sequences of the aforementioned primers used are as follows:

```
                                       (SEQ ID NO: 21)
P1:  GCTCTAGAGTATCGGCGTGGAGTTGTC (Xba I)

                                       (SEQ ID NO: 22)
P2:  TAGTGGAGTAGCTTTATTTTGCGACACCTGCC

                                       (SEQ ID NO: 23)
P3:  GTCGCA AAATAAAGCTACTCCACTAGTGTGATCG

                                       (SEQ ID NO: 24)
P4:  GGTTCCTCCTTTGCGTAAGACCTCACTCGC

                                       (SEQ ID NO: 25)
P5:  GAGGTCTTACGCAAAGGAGGAACCGAATGAAGACATTTGA

                                       (SEQ ID NO: 26)
P6:  CGCGGATCCCAGGATCTGCTGCTCTGG (BamH I)

                                       (SEQ ID NO: 27)
P7:  CCCAAGCTTCGAGGAAACCGTTGAGGA (Hind III)

                                       (SEQ ID NO: 28)
P8:  TAGTGGAGTAGCTATGGATTTCACCTCTGTGAATG

                                       (SEQ ID NO: 29)
P9:  TCTCCACTTTAGGTAAGCTACTCCACTAGTGTGATCG

                                       (SEQ ID NO: 30)
P10: CGATCCTCCTTTGCGTAAGACCTCACTCGC

                                       (SEQ ID NO: 31)
P11: GAGGTCTTACGCAAAGGAGGATCGCCATGTTGAATGTC

                                       (SEQ ID NO: 32)
P12: CGCGGATCCGGCAGAGGCATCAGCAAG (BamH I)

                                       (SEQ ID NO: 33)
P13: ATGTGCTGCAAGGCGATTAA

                                       (SEQ ID NO: 34)
P14: TATGCTTCCGGCTCGTATGT

                                       (SEQ ID NO: 35)
P15: TTTTATATATGGGTATCGGCGGTCTATGCT.
```

The homologous recombinant plasmid pK18mobsacB-$P_{glyA}$::$P_{hisEG}$ identified through sequencing is electronically transformed into the wild type of *Corynebacterium glutamicum* ATCC13032. The kanamycin resistance screening is employed to obtain the bacterial colony that the recombinant plasmid is integrated on the chromosome. The sugar screening is employed to obtain the positive bacterial colony after two homologous recombinations. The positive colony is identified through PCR amplification with P15 and P6 as the primers and 948 bp is obtained as the recombinant bacteria and named as *Corynebacterium glutamicum* WT $P_{glyA}$::$P_{hisEG}$.

The homologous recombinant plasmid pK18mobsacB-$P_{glyA}$::$P_{hisEG}$ identified through sequencing is electronically transformed into *Corynebacterium glutamicum* WT-$P_{glyA}$::$P_{hisEG}$. The kanamycin resistance positive screening is employed to obtain the bacterial colony that the recombinant plasmid is integrated on the chromosome. The sugar inverse screening is employed to obtain the positive bacterial colony after two homologous recombinations. The positive colony is identified through PCR amplification with P15 and P12 as the primers and 833 bp is obtained as the recombinant bacteria and named as *Corynebacterium glutamicum* CG158 (WT-$P_{glyA}$::$P_{hisEG}$-$P_{glyA}$::$P_{hisDCB}$).

After the genome DNA of the recombinant bacterium is extracted and sequenced, the result proves that the promoters of the hisEG and hisDCB in the wild type of *Corynebacterium glutamicum* ATCC13032 have been replaced successfully with the endogenous strong $P_{glyA}$ in *Corynebacterium glutamicum*, the RBS of the genes hisE and hisD is replaced with the conserved RBS sequence (AAAGGAGGA) of the highly expressed gene of *Corynebacterium glutamicum*, the initiation codon GTG of the gene hisE is replaced with ATG of high expression intensity, thus *Corynebacterium glutamicum* CG158 (WT-$P_{glyA}$::$P_{hisEG}$-$P_{glyA}$::$P_{hisDCB}$) is constructed successfully.

1. 2. Obtaining L-Histidine Base Engineering Bacteria CG160 Through Site-Directed Mutation of Gene on the Chromosome The site-directed mutation of the gene hisG on chromosome goes through a procedure of two-step replacement in order to realize three simultaneous site-directed mutations on the gene. First, the homologous recombination is carried out between the long segment containing the chloramphenicol resistant gene $Cm^r$ and the upstream and downstream homologous arm of the mutation segment of the gene hisG as shown by SEQ ID NO: 9 in the sequence table, and CG158 to obtain the recombinant bacteria WT-$P_{glyA}$:$P_{hisEG}$-$Cm^r$::hisG-$P_{glyA}$::$P_{hisDCB}$; then another homologous recombination is carried out between the long segment containing the 264 bp of segment at the end of the gene hisG with three point mutations and its upstream and downstream homologous arms as shown by SEQ ID NO: in the sequence table, and the recombinant bacteria WT-$P_{hisEG}$-$CM^r$::hisG-$P_{glyA}$::$P_{hisDCB}$ to obtain CG160.

The details are as follows:

The genome DNA of *Corynebacterium glutamicum* ATCC13032 is used as template with P16 and P17 as the primers to carry out PCR amplification on the upstream homologous arms of the mutation segment of the gene hisG, P18 and P19 are used as the primers to amplify the downstream homologous arm of the mutation segment of the gene hisG; P20 and P21 are used as the primers with the plasmid pXMJ19 (purchased from Biovector Science Lab, Inc. Product number: SMD1168H) as the template to amplify the chloramphenicol resistant gene $Cm^r$. Then the PCR product above is purified and used as the template with P16 and P21 as the primers to carry out amplification with the technique of overlap extension PCR (SOE) and obtain 1689 bp of long segment (SEQ ID NO: 9) containing the chloramphenicol resistant gene $Cm^r$ and the upstream and downstream homologous arms of the mutation segment of the gene hisG, wherein: No. 1-420 nucleotides of 5' end in SEQ ID NO: 9 is the upstream homologous arm of the mutation segment of the gene hisG, No. 421-1281 nucleotides of 5' end in SEQ ID NO: 9 is the chloramphenicol resistant gene $Cm^r$, No. 1282-1689 nucleotides of 5' end in SEQ ID NO: 9 is the downstream homologous arm of the mutation segment of the gene hisG.

The genome DNA of *Corynebacterium glutamicum* is used as the template with P28 and P29 as the primers to amplify the segment of the gene hisG containing C645G (No. 215 asparagine is mutated to lysine) mutation locus, P30 and P31 are used as the primers to amplify the segment hisG containing the mutation loci A693C and A703G (No. 231 leucine is mutated to phenylalanine and No. 235 threonine is mutated to alanine). Then the PCR product above is purified and used as the template with P28 and P31 as the primers to carry out amplification with the technique of overlap extension PCR (SOE) and obtain 846 bp of the gene hisG containing three point mutations (No. 1007-1852 nucleotides of 5' end of SEQ ID NO: 4). P16 and P22 are used as the primers to carry out PCR amplification on the upstream homologous arm of the site-directed mutation of the gene hisG, P25 and P21 are used as the primers to amplify the downstream homologous arm of the site-directed mutation of the gene hisG; P23 and P24 are used as the primers and the gene hisG containing three point mutations obtained as above is used as the template to amplify the 264 bp of segment at the end of the gene hisG containing three point mutations. Then the PCR product above is purified and used as the template with P16 and P21 as the primers to carry out amplification with the technique of overlap extension PCR (SOE) and obtain 1092 bp of long segment (SEQ ID NO: 10) containing 264 bp of segment at the end of the gene hisG with three point mutations and its upstream and downstream homologous arms, wherein: No. 1-420 nucleotides of 5' end in SEQ ID NO: 10 is the upstream homologous arm, No. 421-684 nucleotides of 5' end in SEQ ID NO: 10 is the 264 bp of segment at the end of the gene hisG containing three point mutations, No. 685-1092 nucleotides of 5' end in SEQ ID NO: 10 is the downstream homologous arm.

After double-enzyme digestion, two PCR products after extraction and purification connect with the knocking-out vector pK18mobsacB after the same double-enzyme digestion. The connection product is transformed through chemical method into *Escherichia Coli* DH5α and the transformant is screened on LB plate containing kanamycin (50 μg/mL). After the transformant is sub-cultured three generations, P13 and P14 are used as the primers and the colony PCR is employed to identify the transformant and obtain the positive transformants of 1901 bp and 1304 bp separately containing two types of recombinant plasmids. The plasmids of the transformants after identified are extracted and identified through double-enzyme digestion by BamH I and EcoR I to obtain two recombinant plasmids respectively of 1689 bp and 1092 bp. After further verified through sequencing, the recombinant plasmids pK18mobsacB-$Cm^r$::hisG and pK18mobsacB-$hisG^{fbr}$::$Cm^r$ are constructed successfully.

The pK18mobsacB-$Cm^r$::hisG is the recombinant vector obtained through inserting the long segment (SEQ ID NO: 9) containing the chloramphenicol resistant gene $Cm^r$ and the upstream and downstream homologous arms of the mutation segment of the gene hisG into the vector pK18mobsacB.

pK18mobsacB-$hisG^{fbr}$::$Cm^r$ is the recombinant vector obtained through inserting the long segment (SEQ ID NO: 10) containing the 264 bp of segment at the end of the gene hisG with three point mutatios and its upstream and downstream homologous arms into the vector pK18mobsacB.

The sequences of the primers used above are as follows:

```
                                   (SEQ ID NO: 36)
P16: CGCGGATCCATCTACGTTGCTGGTGGC (BamH I)

                                   (SEQ ID NO: 37)
P17: ACGGGCAACAGCTGCTGCTCTGGGGTGAC

                                   (SEQ ID NO: 38)
P18: CAGAGCAGCAGCTGTTGCCCGTCTCACTGGT

                                   (SEQ ID NO: 39)
P19: GGTAGTTAAAATTACGCCCCGCCCTGCCACT

                                   (SEQ ID NO: 40)
P20: GCGGGGCGTAATTTTAACTACCCCCGAAAAT

                                   (SEQ ID NO: 41)
P21: CCGGAATTCCGAATGAAATCTGGGACG (EcoR I)

                                   (SEQ ID NO: 42)
P22: CGAAGCAGGATCTGCTGCTCTGGGGTGAC
```

-continued

```
                                   (SEQ ID NO: 43)
P23: CAGAGCAGCAGATCCTGCTTCGCCGCATCCA

                                   (SEQ ID NO: 44)
P24: GGTAGTTAAAACTAGATGCGGGCGATGCG

                                   (SEQ ID NO: 45)
P25: CCCGCATCTAGTTTTAACTACCCCCGAAAAT

                                   (SEQ ID NO: 46)
P26: TCCCAAACAAAGGCTCGC

                                   (SEQ ID NO: 47)
P27: CAGTCGGCGGTTTGCTAA

                                   (SEQ ID NO: 48)
P28: ATGTTGAAAATCGCTG

                                   (SEQ ID NO: 49)
P29: TTACTGCAGTGGCAGCGTCCAGGTTGTCGCGGTCGACCTTGTAAT

CCAGCAT

                                   (SEQ ID NO: 50)
P30: ACCTGGACGCTGCCACTGCAGTAACCCCAGGCTTCTCCGGCCCAG

CGGTATC

                                   (SEQ ID NO: 51)
P31: CTAGATGCGGGCGATGCGG.
```

The homologous recombinant plasmid pK18mobsacB-$Cm^r$::hisG identified through sequencing is electronically transformed into *Corynebacterium glutamicum* CG158 and the kanamycin resistance screening is employed to obtain the bacterial colony that the recombinant plasmid is integrated on the chromosome and the sugar screening is employed to obtain the positive bacteria after two homologous recombinations. P26 and P27 are used as the primers to carry out PCR amplification and identification on the positive bacteria and obtain 1872 bp of recombinant bacteria WT-$P_{glyA}$::$P_{hisEG}$-$Cm^r$::hisG-$P_{glyA}$::$P_{hisDCB}$.

The homologous recombinant plasmid identified through sequencing pK18mobsacB-$hisG^{fbr}$::$Cm^r$ is electronically transformed into the aforementioned constructed recombinant bacteria WT-$P_{oyA}$::$P_{hisEG}$-$Cm^r$::hisG-$P_{glyA}$::$P_{hisDCB}$ and the kanamycin resistance screening is employed to obtain the bacterial colony where the recombinant plasmid is integrated onto the chromosome and the sugar screening is employed to obtain the positive bacterial colony after two homologous recombinations. P26 and P27 are used as the primers to carry out PCR amplification and identification on the positive colony and obtain 1275 bp of the recombinant bacteria which is named as *Corynebacterium glutamicum* CG160 (WT-$P_{glyA}$::$P_{hisEG}$-$hiSG^{fbr}$-$P_{glyA}$::$P_{hisDCB}$).

After the genome DNA of the recombinant bacterium is extracted and sequenced, the result proves that the N215K/L231F/T235A of the gene hisG of the chromosome of *Corynebacterium glutamicum* CG158 have successful point mutation and *Corynebacterium glutamicum* CG160 (WT-$P_{hisEG}$-$SG^{fbr}$-$P_{hisDCB}$) is constructed successfully.

The point mutations of N215K/L231F/T235A of the gene hisGare to mutate No. 215 asparagine of ATP-phosphoribosyl transferase (HisG) encoded by the gene hisGto lysine, No. 231 leucine to phenylalanine and No. 235 threonine to alanine.

Embodiment 2: Construction of L-Histidine High-Yield Recombinant Bacteria CG171 Containing Plasmid In this embodiment, on the basis of the primary engineering bacteria obtained in Embodiment 1, the gene prsAis further over-expressed and the gene $hisG^{fbr}$ (No. 1007-1852 nucleotide sequence in SEQ ID NO: 4) is also over-expressed. Then knocking-out of the gene pgi (SEQ ID NO: 13) and over-expression of the gene zwf-opcA (SEQ ID NO: 2) are combined to obtain the high-yield engineering bacteria CG171.

2.1 Construction of L-Histidine Primary Engineering Bacteria CG176

The gene prsA encodes the PRPP synthetase (PrsA as shown by SEQ ID NO: 5. PRPP is the precursor substance for histidine synthesis), enhances the expression of the gene prsA in order to increase the synthesis of the precursor PRPP for histidine synthesis and provides more precursor substances for histidine synthesis.

On the basis of the base engineering bacteria CG160 obtained in Embodiment 1, both the gene prsA (as shown by No. 15-992 nucleotide sequence of 5' end in SEQ ID NO: 4) and the gene $hisG^{fbr}$ (as shown by No. 1007-1852 nucleotide of 5' end in SEQ ID NO: 4) are over-expressed in order to obtain the primary engineering bacteria CG176 with higher histidine yield. Thus, it will be convenient to implement the strategy according to the present invention and achieve a better performance. Of course, the skilled in the art may easily understand that the modification strategy according to the present invention shall not only be limited to recombination and modification on the primary engineering bacteria obtained in this embodiment, it can also be applied to other engineering bacteria of histidine.

The genome DNA of the strain CG160 is used as the template with P32/P33 and P34/P35 respectively as the primers to carry out PCR amplification on the gene prsA (992 bp) and the gene $hisG^{fbr}$ (860 bp). The overlap extension PCR is employed to connect both genes and the amplified genes of $hisG^{fbr}$ and prsA are used as the template with P32 and P35 as the primers to carry out PCR amplification. The obtained 1852 bp of PCR product is the segment prsA-$hisG^{fbr}$ (SEQ ID NO: 4), wherein: No. 15-992 nucleotides of 5' end in SEQ ID NO: 4 is prsA, No. 1007-1852 nucleotides of 5' end in SEQ ID NO: 4 is $hisG^{fbr}$ (the gene hisG containing three point mutations).

After double-enzyme digestion by Xba I and Sma I, the PCR product as above connects with the shuttle expression plasmid pXMJ19 of *Corynebacterium glutamicum-Escherichia coli* after the same double-enzyme digestion. The connection product is transformed through chemical method into *Escherichia coli* DH5α and the transformant is screened on LB plate containing chloramphenicol (20 μg/mL). After the transformant is sub-cultured three generations, P36 and P37 are used as the primers and the colony PCR is employed to identify the transformant and obtain 2054 bp being the positive transformant. The plasmid of the transformant after identified is extracted and identified through double-enzyme digestion by Xba I and Sma I to obtain 1852 bp being positive.

The pXMJ19-prsA-$hisG^{fbr}$ is further sequenced and analyzed. This plasmid is the vector pXMJ19-prsA-$hisG^{fbr}$ obtained through inserting the segment prsA-$hisG^{fbr}$ (SEQ ID NO: 4) between the enzyme digestion sites of Xba I and Sma I of the plasmid pXMJ19. It is named as the recombinant plasmid pWYE 1230 (as shown in FIG. 1).

The plasmid pXMJ19-prsA-$hisG^{fbr}$ is transformed into the base engineering bacteria CG160 constructed as above. P36 and P37 are used as the primers and the colony PCR is employed to identify the transformant and obtain 2054 bp being the positive transformant. The plasmid of the transformant identified is extracted and identified to further confirm that the over-expressed plasmid is successfully transformed into the engineering bacteria and the L-histidine engineering bacteria CG176 WT-$P_{glyA}$::$P_{hisEG}$-$hisG^{fbr}$-$P_{glyA}$::$P_{hisDCB}$/PXMJ19-prsA-$hisG^{fbr}$) is constructed successfully.

The sequences of the primers used above are as follows:

```
                                          (SEQ ID NO: 52)
P32: GCTCTAGAAAAGGAGGATCCTCATGACTGCTCACTGG (Xba I)

                                          (SEQ ID NO: 53)
P33: TTGTCCTCCTTTTTAGGCCTCGCCCTCGAA

                                          (SEQ ID NO: 54)
P34: GGCGAGGCCTAAAAAGGAGGACAATCATGTTGAAAATCGCTG

                                          (SEQ ID NO: 55)
P35: TCCCCCGGGCTAGATGCGGGCGATGCGG (Sma I)

                                          (SEQ ID NO: 56)
P36: CAATTAATCATCGGCTCGTA

                                          (SEQ ID NO: 57)
P37: ACCGCTTCTGCGTTCTGATT.
```

2.2 Obtaining L-Histidine Primary Engineering Bacteria CG161 and CG172

The gene pgi encodes the glucose phosphate isomerase (Pgi as shown by SEQ ID NO: 14). On the basis of the base bacteria CG160 obtained as above, the gene pgi is knocked out (SEQ ID NO: 13) to obtain the primary engineering bacteria CG161. On the basis of CG161, both the gene prsA and the gene $hisG^{fbr}$ are over-expressed to obtain the engineering bacteria CG172 in which the pgi gene is knocked out.

The primary engineering bacteria CG161 is obtained through knocking out the gene pgi (SEQ ID NO: 13) from the L-histidine base engineering bacteria CG160. The details are as follows:

First, the primers are separately designed according to the gene pgi of the *Corynebacterium glutamicum* ATCC13032 and its upstream and downstream sequences in Genbank.

The genome DNA of *Corynebacterium glutamicum* ATCC13032 is used as the template with P38 and P39 as the primers to carry out PCR amplification on the upstream homologous arm of the gene pgi; P40 and P41 are used as the primers to amplify the downstream homologous arm of the gene pgi. Then the PCR product as above is purified and used as the template with P38 and P41 as the primers to carry out amplification with the technique of overlap extension PCR (SOE). 1672 bp of segment containing the upstream and downstream homologous arms of the gene pgi to be knocked out is obtained (SEQ ID NO: 1), wherein: No. 1-834 nucleotides of 5' end in SEQ ID NO: 1 is the upstream homologous arm of the gene pgi to be knocked out, No. 835-1672 nucleotides of 5' end in SEQ ID NO: 1 is the downstream homologous arm of the gene pgi to be knocked out.

After double-enzyme digestion by BamH I and EcoR I, the purified and extracted PCR product connects with the homologous recombinant vector pK18mobsacB after the same double-enzyme digestion. The connection product is transformed through chemical method into *Escherichia coli* DH5α and the transformant is screened on LB plate containing kanamycin (50 μg/mL). After the transformant is sub-cultured three generations, P13 and P14 are used as the primers and the colony PCR is employed to identify the transformant and obtain 1884 bp being the positive transformant. The plasmid of the transformant after identified is extracted and identified through double-enzyme digestion by BamH I and EcoR I to obtain 1672 bp being positive. After further verified through sequencing, the recombinant plasmid pK18mobsacB-Δpgi is constructed successfully. It is the vector obtained through inserting the segment (SEQ ID NO: 1) containing the upstream and downstream homologous arms of the gene pgi to be knocked out between the enzyme digestion sites of BamH I and EcoR I of the vector pK18mobsacB.

The sequences of the primers used are as follows:

```
                                 (SEQ ID NO: 58)
P38: CGCGGATCCGCTCTTTCGGAGTGACCT (BamH I)

                                 (SEQ ID NO: 59)
P39: TAAGCAAGCGAGAAAACTCCTTTATTGTCG

                                 (SEQ ID NO: 60)
P40: TAAAGGAGTTTTCTCGCTTGCTTATAGGGTC

                                 (SEQ ID NO: 61)
P41: CCGGAATTCTCGGGAAGCAGTTAGTGAAA (EcoR I)

                                 (SEQ ID NO: 62)
P42: TTGACGACGCAAGAGCCA

                                 (SEQ ID NO: 63)
P43: CACCATTACCGATGAGAAAC.
```

Figure 2:
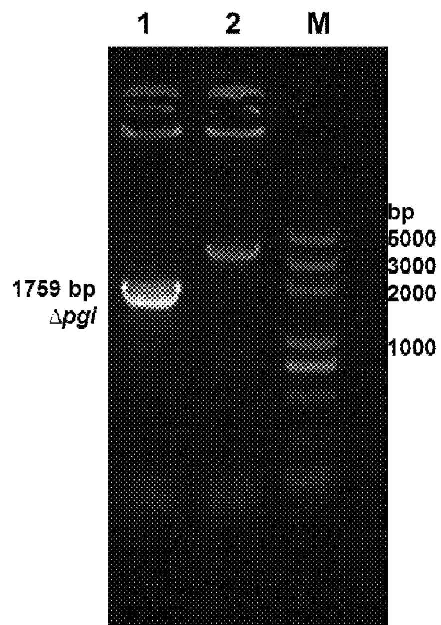
FIG. 2 is the electro-phoretogram of PCR identification of the genome DNA of the bacterial strain CG161 (gene pgi is knocked out).

The homologous recombinant plasmid pK18mobsacB-Δpgi identified through sequencing is electronically transformed into the *Corynebacterium glutamicum* CG160. The kanamycin resistance screening is employed to obtain the bacterial colony that the recombinant plasmid is integrated on the chromosome and the sugar screening is employed to obtain the bacterial colony after a second homologous recombination. P42 and P43 are used as the primers for PCR identification with the extracted genome DNA of the colony as the template so as to obtain 1759 bp being positive (FIG. 2). It is named as CG161 (WT-$P_{glyA}$::$P_{hisEG}$-hiS$G^{fbr}$-$P_{glyA}$::$P_{hisDCB}$-ΔPgi).

The CG161 (WT-$P_{glyA}$::$P_{hisEG}$-hiS$G^{fbr}$-$P_{glyA}$::$P_{hisDCB}$-ΔPgi) is further sequenced and analyzed.

The result shows that the gene pgi of the chromosome of the L-histidine base engineering bacteria CG160 is knocked out successfully and CG161 is constructed successfully.

The engineering bacteria CG172 is the recombinant bacteria (WT-$P_{glyA}$::$P_{hisEG}$-his$G^{fbr}$-$P_{glyA}$::$P_{hisDCB}$-Δpgi/pXMJ19-prsA-his$G^{fbr}$) obtained through introducing the plasmid pXMJ19-prsA-his$G^{fbr}$ into the engineering bacteria CG161. The specific operating methods are conventional and hence omitted here.

3. Construction of L-Histidine High-Yield Engineering Bacteria CG171 and Comparative Engineering Bacteria CG173

The gene zwf-opcA encodes the glucose-6-phosphate dehydrogenase (Zwf-OpcA as shown by SEQ ID NO: 3 where No. 1-514 amino acids of 5' end constitute Zwf subunit and No. 515-833 amino acids constitute OpcA subunit). The combinational modification through knocking out the gene pgi and over-expression the gene zwf-opcA (SEQ ID NO: 2) is carried out to obtain the high-yield engineering bacteria CG171. As comparison, the engineering bacteria CG173 whose gene pgi is not knocked out but the gene zwf-opcA is over-expressed is obtained.

The primer is designed according to the gene sequence zwf-opcA of *Corynebacterium glutamicum* ATCC13032 in Genbank. The genome DNA of *Corynebacterium glutamicum* ATCC13032 is used as the template with the primers P44 and P45 as the primers to carry out PCR amplification on 2519 bp of the segment zwf-opcA (the initiation codon of the gene zwf is replaced from GTG to ATG in order to enhance its expression) (SEQ ID NO: 2). After double-enzyme digestion by Hind III and Xba I, it connects with the expression plasmid pXMJ19 after the same double-enzyme digestion to obtain the recombinant plasmid pXMJ19-zwf-opcA. The pXMJ19-zwf-opcA is further processed through double-enzyme digestion by XbaI and SmaI and then connects with 1852 bp of the segment prsA-his$G^{fbr}$ obtained through double-enzyme digestion by Xba I and Sma I of the plasmid pXMJ19-prsA-his$G^{fbr}$ prepared above.

In the segment zwf-opcA, No. 1-1545 nucleotides of 5' end in SEQ ID NO: 2 is the gene zwf and No. 1560-2519 nucleotides of 5' end in SEQ ID NO: 2 is the gene opcA.

The connection product is transformed through chemical method into *Escherichia coli* DH5α and the transformant is screened on LB plate containing chloramphenicol (20 μg/mL). After the transformant is sub-cultured three generations, P36 and P37 are used as the primers and the colony PCR is employed to identify the transformant and obtain 4587 bp being the positive transformant. The plasmid of the transformant after identified is extracted and identified through double-enzyme digestion by Xba I/Sma I and Hind III/Xba I to obtain separately 1852 bp and 2533 bp being positive.

Figure 3:
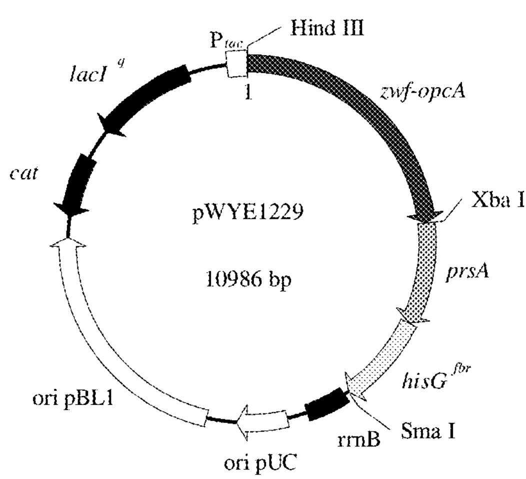
FIG. 3 is the schematic diagram of the recombinant plasmid pXMJ19-zwf-opcA-prsA-hisG$^{fbr}$.

After verified through sequencing, the recombinant plasmid pXMJ19-zwf-opcA-prsA-his$G^{fbr}$ is constructed successfully and named as the recombinant plasmid pWYE 1229 (FIG. 3). It is the vector obtained through inserting the gene zwf-opcA (SEQ ID NO: 2) between the sites of Hind III and Xba I of pXMJ19 as well as inserting the segment prsA-his$G^{fbr}$ (SEQ ID NO: 4) between the sites of Xba I and Sma I.

```
                                                     (SEQ ID NO: 64)
P44: CCCAAGCTTAAAGGAGGACCATCATGAGCACAAACACGACCCCCT

(Hind III)

                                                     (SEQ ID NO: 65)
P45: GCTCTAGATTAGACGGTTTCCAGCTTG (Xba I)
```

The recombinant plasmid pXMJ19-zwf-opcA-prsA-his$G^{fbr}$ is electronically transformed respectively into the engineering bacteria CG160 without pgi deletion and the engineering bacteria CG161 with pgi deletion. P36 and P37 are used as the primers and the colony PCR is employed to identify the transformant. 4587 bp is obtained as the positive transformant. The plasmid of the identified transformant is extracted.

The plasmid is sequenced and the result shows that the engineering bacteria CG173 of L-histidine (WT-$P_{glyA}$::$P_{hisEG}$-his$G^{fbr}$-$P_{glyA}$::$P_{hisDCB}$/pXMJ19-zwf-opcA-prsA-his$G^{fbr}$) contains the plasmid pXMJ19-zwf-opcA-prsA-his$G^{fbr}$. It is the bacteria obtained through introducing the recombinant plasmid pXMJ19-zwf-opcA-prsA-his$G^{fbr}$ into the engineering bacteria CG160.

The CG171 (WT-$P_{glyA}$::$P_{hisEG}$-hiS$G^{fbr}$-$P_{glyA}$::$P_{hisEG}$-his$G^{fbr}$-$P_{glyA}$::$P_{hisDCB}$-Δpgi/pXMJ19-zwf-opcA-prsA-his$G^{fbr}$) contains the plasmid pXMJ19-zwf-opcA-prsA-his$G^{fbr}$. It is the bacteria obtained through introducing the recombinant plasmid pXMJ19-zwf-opcA-prsA-his$G^{fbr}$ into the engineering bacteria CG161.

Figure 4:
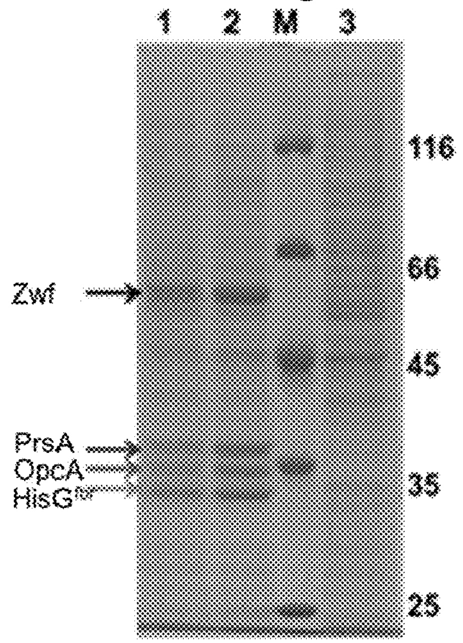
FIG. 4 is the SDS-PAGE diagram of the expression protein of L-histidine engineering bacteria CG171.

The expression of the gene carried by the over-expressed plasmid is further verified. The cell lysis solution of CG171 is prepared to carry out SDS-PAGE test. The result is as shown in FIG. 4 where Lane 1 and 2 are the cell lysis solutions of CG171, Lane 3 is the cell lysis solution of ATCC13032/pXMJ19 (obtained through introducing the plasmid pXMJ19 into ATCC13032). After comparison, it shows that the genes zwf (57.5 kDa), opcA (34.8 kDa), prsA (35.6 kDa) and hisG$^{fbr}$ (30.2 kDa) carried by the over-expressed plasmid are expressed successfully in the engineering bacteria.

Figure 5:
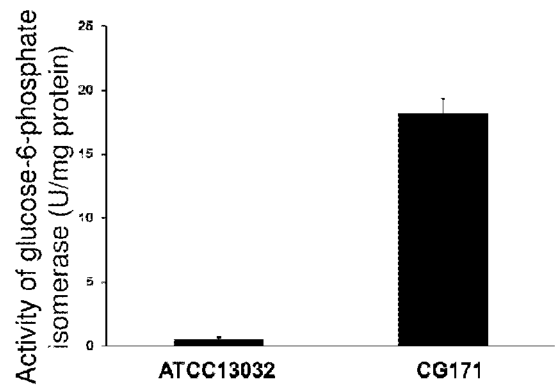
FIG. 5 is the diagram of determining enzyme activity of the glucose-6-phosphate dehydrogenase in L-histidine engineering bacteria CG171.

The specific activity of glucose-6-phosphate dehydrogenase (Zwf-opcA) in the engineering bacterium is further determined. The reaction system for determination (0.5 mL) is as follows: 100 mmol/L Tris-HCl (pH 7.8), 200 mmol/L KCl, 1 mmol/L NADP, 10 mmol/L $MgCl_2$, 5 mmol/L glucose-6-phosphate (G6P) and appropriate amount of cell lysis solution. The reaction is carried out at 30° C. for 5 minutes. The yield of NADPH is reflected through detecting the change of light absorbance at 340 nm. The enzyme activity unit (U) is defined as the amount of enzyme needed to produce 1nmol nicotinamide adenine dinucleotide phosphate (NADPH) in reduced form in every minute. The result is as shown in FIG. 5. Compared with the wild type of strains, the specific activity of glucose-6-phosphate dehydrogenase after over-expression of zwf-opcA through plasmid is improved by 34 times.

Embodiment 3: Construction of L-Histidine High-Yield Engineering Bacteria CG319 Containing Plasmid On the basis of the high-yield engineering bacteria CG171 obtained as above, in order to further over-express the gene purH encoding AICAR transmethylase/IMP ring hydrase (PurH as shown by SEQ ID NO: 16) and hence guide more by-product AICAR increased due to enhanced synthetic pathway of histidine to the synthetic pathway of purine nucleotides, the recombinant plasmid pXMJ19-zwf-opcA-prsA-hisG$^{fbr}$-purH is constructed and introduced into the primary bacteria CG161 to obtain the high-yield engineering bacteria.

The primer is designed according to the gene sequence purH of *Corynebacterium glutamicum* ATCC13032 in Genbank. The genome DAN of ATCC13032 is used as the template and P46 and P47 are used as the primers to carry out PCR amplification on the gene purH (1563 bp) (SEQ ID NO: 15).

After double-enzyme digestion of Sma I and EcoR I, the PCR product as above connects with the shuttle expression plasmid pXMJ19 of *Corynebacterium glutamicum-Escherichia coli* after the same double-enzyme digestion. The connection product is transformed through chemical method into *Escherichia coli* DH5α and the transformant is screened on LB plate containing chloramphenicol (20 μg/mL). After the transformant is sub-cultured three generations, P52 and P53 are used as the primers and the colony PCR is employed to identify the transformant and obtain 1779 bp being the positive transformant. The plasmid of the transformant after identified is extracted and identified through double-enzyme digestion by XbaI and Sma I and obtain 1577 bp being positive and named as the recombinant plasmid pXMJ19-purH.

The recombinant plasmid pXMJ19-zwf-opcA-prsA-hisG$^{fbr}$ is used as the template and P48/P49 and P50/P51 are respectively used as the primer to carry out PCR amplification on the segments zwf-opcA (2519 bp) and prsA-hisG$^{fbr}$ (1852 bp). The overlap extension PCR is employed to connect both segments to obtain 4385 bp of the segment zwf-opcA-prsA-hisG$^{fbr}$ (SEQ ID NO: 17), wherein: No. 15-2533 nucleotides of 5' end in SEQ ID NO: 17 is zwf-opcA and No. 2534-4385 nucleotides of 5' end in SEQ ID NO: 17 is prsA-hisG$^{fbr}$.

Figure 6:
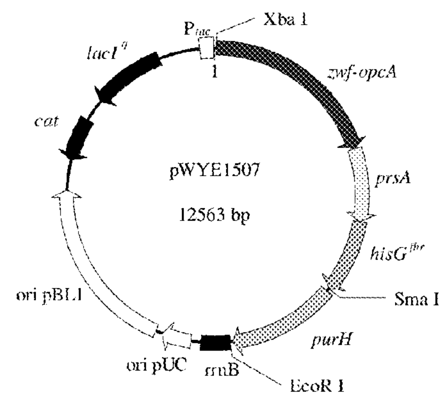
FIG. 6 is the schematic diagram of the recombinant plasmid pXMJ19-zwf-opcA-prsA-hisG$^{fbr}$-purH.

After double-enzyme digestion by Xba I and Sma I, the PCR product as above connects with the recombinant plasmid pXMJ19-purH after the same double-enzyme digestion. The connection product is transformed through chemical method into *Escherichia coli* DH5α and the transformant is screened on LB plate containing chloramphenicol (20 μg/mL). After the transformant is sub-cultured three generations, P52 and P53 are used as the primers and the colony PCR is employed to identify the transformant and obtain the 6164 bp being the positive transformant. The plasmid of the transformant after identified is extracted and identified through double-enzyme digestion by Xba I and Sma I to obtain 4385 bp being positive and named as the recombinant plasmid pWYE1507 pXMJ19-zwf-opcA-prsA-hisG$^{fbr}$-purH) (as shown in FIG. 6).

The pXMJ19-zwf-opcA-prsA-hisG$^{fbr}$-purH is further sequenced and analyzed. The result shows that this plasmid is the vector obtained through inserting the segment zwf-opcA-prsA-hisG$^{fbr}$(SEQ ID NO: 17) between the enzyme digestion sites Xba I and Sma I of pXMJ19 as well as inserting purH between the enzyme digestion sites Sma I and EcoR I of the plasmid pXMJ19.

The plasmid pXMJ19-zwf-opcA-prsA-hisG$^{fbr}$-purH is transformed into the engineering bacteria CG161. P52 and P53 are used as the primers and the colony PCR is employed to identify the transformant and obtain 6164 bp being the positive transformant. The plamid of the transformant after identified is extracted and further confirmed that the over-expressed plasmid is successfully transformed into the engineering bacteria and the engineering bacteria of L-histidine CG319 (WT-$P_{glyA}$::$P_{hisEG}$-hisG$^{fbr}$-$P_{glyA}$::$P_{hisDCB}$-Δpgi/pXMJ19-zwf-opcA-prsA-hisG$^{fbr}$-purH) is constructed successfully.

The sequences of the primers used above are as follows:

```
                                        (SEQ ID NO: 66)
P46: TCCCCCGGGAAAGGAGGACCTTCATGAGCGATGATCGTAAG
(Sma I)

                                        (SEQ ID NO: 67)
P47: CCGGAATTCTTAGTGAGCGAAGTGTCGCG (EcoR I)

                                        (SEQ ID NO: 68)
P48: GCTCTAGAAAAGGAGGACCATCATGAGCACAAACACGACCC
(Xba I)

                                        (SEQ ID NO: 69)
P49: AGTCATGAGGATCCTCCTTTTTAGACGGTTTCCAGCTTG

                                        (SEQ ID NO: 70)
P50: TCAAGCTGGAAACCGTCTAAAAAGGAGGATCCTCATGACTGCTCA
CTG

                                        (SEQ ID NO: 71)
P51: TCCCCCGGGCTAGATGCGGGCGATGCGGATTTC(Sma I)

                                        (SEQ ID NO: 72)
P52: CAATTAATCATCGGCTCGTA

                                        (SEQ ID NO: 73)
P53: ACCGCTTCTGCGTTCTGATT
```

Embodiment 4: Construction of L-Histidine High-Yield Engineering Bacteria CG328 Containing Plasmid On the basis of CG139 obtained as above, in order to weaken the gene purF encoding the amidophosphoribosyl transterase (PurF, SEQ ID NO: 19) and increase the distribution of the precursor substance PRPP to the synthetic pathway of histidine, the promoter of purF in the primary engineering bacteria CG161 is replaced with $P_{hom}$ to obtain CG327 and then the plasmid is introduced to obtain the high-yield engineering bacteria CG328.

The promoter of the gene purF of the primary engineering bacteria CG161 is replaced with $P_{hom}$ to obtain the engineering bacteria CG327. The details are as follows:

First, the primers are designed separately according to the gene purF of *Corynebacterium glutamicum* ATCC13032 and its upstream and downstream sequences in Genbank.

The genome DNA of *Corynebacterium glutamicum* ATCC13032 is used as the template with P54 and P55 as the primers to carry out PCR amplification on the upstream homologous arm of the gene purF; P56 and P57 are used as the primers to amplify the promoter $P_{hom}$, P58 and P59 are used as the primers to amplify the downstream homologous arm of the gene purF. Then the PCR product as above is purified and used as the template with P54 and P59 as the primers to carry out amplification with the technique of overlay extension PCR (SOE) and obtain 1654 bp of the segment containing the promoter $P_{hom}$ and the upstream and downstream homologous arms of the promoter of the gene purF (SEQ ID NO: 18), wherein: No. 1-735 nucleotides of 5' end in SEQ ID NO: 18 is the upstream of the promoter of the gene purF, No. 736-865 nucleotides of 5' end in SEQ ID NO: 18 is the promoter $P_{hom}$, No. 866-1654 nucleotides of 5' end in SEQ ID NO: 18 is the downstream homologous arm of the promoter of the gene purF.

After double-enzyme digestion by BamH I and EcoR I, the purified and extracted PCR product connects with the homologous recombinant vector pK18mobsacB after the same double-enzyme digestion. The connection product is transformed through chemical method into *Escherichia coli* DH5α and the transformant is screened on LB plate containing kanamycin (50 μg/mL). After the transformant is sub-cultured three generations, P13 and P14 are used as the primers and the colony PCR is employed to identify the transformant and obtain 1866 bp being the positive transformant. The plasmid of the transformant after identified is extracted and identified through double-enzyme digestion by BamH I and EcoR I and obtain 1654 bp being positive. After further verified through sequencing, the recombinant plasmid pK18mobsacB-$P_{hom}$::$P_{purF}$ is constructed successfully. It is the vector obtained through inserting the segment (SEQ ID NO: 18) containing the promoter $P_{hom}$ and the upstream and downstream homologous arms of the promoter to be replaced between the enzyme digestion sites BamH I and EcoR I of the vector pK18mobsacB.

The sequences of the primers used above are as follows:

```
                                    (SEQ ID NO: 74)
P54: CGCGGATCCTCCGCAGAAAGCACCTCA (BamH I)

                                    (SEQ ID NO: 75)
P55: TTTAGTTTTCAACGGCTAAAGTTTGACCACTGG

                                    (SEQ ID NO: 76)
P56: GTGGTCAAACTTTAGCCGTTGAAAACTAAAAAGC
```

-continued

```
                                    (SEQ ID NO: 77)
P57: TCCGGTCCTCCTTTTACTTTGTTTCGGCCACCC

                                    (SEQ ID NO: 78)
P58: GGCCGAAACAAAGTAAAAGGAGGACCGGAATGACCCAGGTAAACC

AC

                                    (SEQ ID NO: 79)
P59: CCGGAATTCAACCTTTGCGGGTTGTCT (EcoR I)
```

The homologous recombinant plasmid pK18mobsacB-$P_{hom}$::$P_{purF}$ after identified through sequencing is electronically transformed into *Corynebacterium glutamicum* CG161 and the kanamycin resistance screening is employed to obtain the bacterial colony that the recombinant plasmid is integrated on the chromosome and the sugar screening is employed to obtain the bacterial colony after a second homologous recombination. P56 and P59 are used as the primers to extract the genome DAN of the colony and carry out PCR amplification and identification and obtain 905 bp being positive. It is named as CG327 (WT-$P_{glyA}$::$P_{hisEG}$-hisG$^{fbr}$-$P_{glyA}$::$P_{hisDCB}$-Δpgi::$P_{hom}$::$P_{purF}$). CG327 (WT-$P_{glyA}$::$P_{hisEG}$-hiSG$^{fbr}$-$P_{glyA}$::$P_{hisDCB}$-Δpgi::$P_{hom}$::$P_{purF}$) is further sequenced and analyzed. The result shows that the promoter of the gene purF of the chromosome of the L-histidine primary engineering bacteria CG161 is replaced with $P_{hom}$ and CG327 is constructed successfully.

Figure 7:
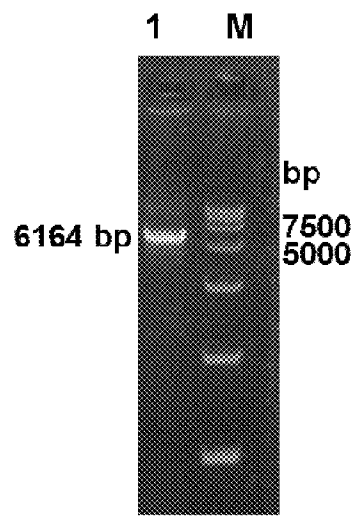
FIG. 7 is the electro-phoretogram of PCR identification of the plasmid DNA carried by the bacterial strain CG328.

The engineering bacteria CG328 is the recombinant bacteria WT-$P_{glyA}$::$P_{hisEG}$-hiSG$^{fbr}$-$P_{glyA}$::$P_{hisDCB}$-Δpgi::$P_{hom}$::$P_{purF}$/pXMJ19-zwf-opcA-prsA-hisG$^{fbr}$-purH) obtained through introducing the plasmid pXMJ19-zwf-opcA-prsA-hisG$^{fbr}$-purH into the engineering bacteria CG327. The specific operating methods are similar to those preparing the engineering bacteria CG319 as above and conventional, so are not detailed here. PCR identification is carried out on the plasmid carried by the strain CG328. P52 and P53 are used as the primers to obtain 6164 bp of segment (FIG. 7). This DNA segment is sequenced and the result shows that it is the segment zwf-opcA-prsA-hisG$^{fbr}$-purH and the strain CG328 is constructed successfully.

Embodiment 5: Construction of L-Histidine High-Yield Recombinant Bacteria CG351 Containing No Plasmid Carrying plasmid can impose metabolic burden on engineering bacteria and is not favorable to control the industrial fermentation of engineering bacteria and the safety of fermented products. Thus, in this embodiment, the expression of the gene carrying plasmid is increased on chromosome to construct a histidine engineering bacteria containing no plasmid so as to reduce the metabolic burden of engineering bacteria and realize the maximum conversion from the fermentation substrate(s) to the product(s).

In this embodiment, further modification is carried out on the basis of the primary engineering bacteria CG161 whose the gene pgi is knocked out: use the promoter $P_{sod}$ to replace the promoter of the gene prsA in order to enhance the expression of PRPP synthetase (PrsA) and hence obtain CG350; moreover, use the promoter $P_{eftu}$ to replace the promoter of the operon tkt-tal-zwf-opcA-devB in order to improve the expression of glucose-6-phosphate dehydrogenase (Zwf-OpcA) and hence obtain CG351.

The primers are designed separately according to the gene prsA of *Corynebacterium glutamicum* ATCC13032 in Genbank and its upstream and downstream sequences as well as the subsequence of the promoter $P_{sod}$.

The genome DNA of *Corynebacterium glutamicum* ATCC13032 is used as the template with P60 and P61 as the primers to amplify the upstream homologous arm of the promoter prsA; P62 and P63 are used as the primers to amplify the promoter $P_{sod}$; P64 and P65 are used as the primers to amplify the downstream homologous arm of the promoter prsA. Then the PCR product as above is purified and used as the template. P60 and P65 are used as the primers and the technique of overlap extension PCR (SOE) is employed to carry out amplification and obtain 1455 bp of PCR product. It is the segment (SEQ ID NO: 11) containing the replacing promoter $P_{sod}$ and the upstream and downstream homologous arms of the replaced promoter $P_{prsA}$; wherein: No. 1-655 nucleotides of 5' end in SEQ ID NO: 11 is the upstream homologous arm of the replaced promoter $P_{prsA}$, No. 656-847 nucleotides of 5' end in SEQ ID NO: 11 is the promoter $P_{sod}$, No. 848-1455 nucleotides of 5' end in SEQ ID NO: 11 is the downstream homologous arm of the replaced promoter $P_{prsA}$.

After double-enzyme digestion by Hind III and BamH I, the PCR product of 1455 bp as above connects with the homologous recombinant vector pK18mobsacB after the same double-enzyme digestion. The connection product is transformed through chemical method into *Escherichia coli* DH5α and the transformant is screened on LB plate containing kanamycin (50 μg/mL). After the transformant is sub-cultured three generations, P13 and P14 are used as the primers and the colony PCR is employed to identify the transformant and obtain 1667 bp being the positive transformant. The plasmid of the transformant after identified is extracted and identified through double-enzyme digestion by Hind III and BamH I to obtain 1455 bp being positive.

The positive plasmid is sequenced and the result shows that this plasmid is the recombinant plasmid obtained through inserting the nucleotide as shown by SEQ ID NO: in the sequence table into the vector pK18mobsacB and named as pK18mobsacB-$P_{sod}$::$P_{prsA}$.

The same method is employed to construct the homologous recombinant plasmid pK18mobsacB-$P_{eftu}$::$P_{tkt}$ and the promoter of the operon tkt-tal-zwf-opcA-devB is replaced with the strong promoter $P_{eftu}$. The details are as follows: use P66 and P67 as the primers to amplify the upstream homologous arm of the promoter of the operon tkt-tal-zwf-opcA-devB; use P68 and P69 as the primers to amplify the promoter $P_{eftu}$; use P70 and P71 as the primers to amplify the downstream homologous arm of the promoter of the operon tkt-tal-zwf-opcA-devB. P66 and P71 are used as the primers and the technique is of overlap extension PCR (SOE) is employed to carry out amplification. The PCR product of 1512 bp is obtained and it is the long segment (SEQ ID NO: 12) containing the replacing promoter $P_{etfu}$ and the upstream and downstream homologous arms of the replaced promoter $P_{tkt}$, wherein: No. 1-634 nucleotides of 5' end in SEQ ID NO: 12 is the upstream homologous arm of the replaced promoter $P_{tkt}$, No. 635-834 nucleotides of 5' end in SEQ ID NO: 12 is the promoter $P_{eftu}$, No. 835-1512 nucleotides of 5' end in SEQ ID NO: 12 is the downstream homologous arm of the replaced promoter $P_{tkt}$.

After double-enzyme digestion by Hind III and BamH I, the PCR product of 1512 bp as above connects with the homologous recombinant vector pK18mobsacB after the same double-enzyme digestion. The connection product is transformed through chemical method into *Escherichia coli* DH5α and the transformant is screened on LB plate containing kanamycin (50 μg/mL). After the transformant is sub-cultured three generations, P13 and P14 are used as the primers and the colony PCR is employed to identify the transformant and obtain 1724 bp being the positive transformant. The plasmid of the transformant after identified is extracted and identified through double-enzyme digestion by Hind III and BamH I to obtain 1512 bp being positive. The positive plasmid is sequenced and the result shows that this plasmid is the recombinant plasmid obtained through inserting the nucleotides as shown by SEQ ID NO: 12 in the sequence table into the vector pK18mobsacB and named as pK18mobsacB-$P_{eftu}$::$P_{tkt}$.

The sequences of the primers used above are as follows:

```
                                        (SEQ ID NO: 80)
P60: CCCAAGCTTTCCAGCAACCACCTGGAT (Hind III)

                                        (SEQ ID NO: 81)
P61: AATTGGCAGCTATTAGCCTTCCTGGTTGTG

                                        (SEQ ID NO: 82)
P62: CAGGAAGGCTAATAGCTGCCAATTATTCCG

                                        (SEQ ID NO: 83)
P63: TTGTCCTCCTTTGGGTAAAAAATCCTTTCG

                                        (SEQ ID NO: 84)
P64: GATTTTTTACCCAAAGGAGGACAACCATGACTGCTCACTGGAA

                                        (SEQ ID NO: 85)
P65: CGCGGATCCCGCCATTGGGGCATCGCC(BamH I)

                                        (SEQ ID NO: 86)
P66: CCCAAGCTTTCAACGATCACTGCCCAG(Hind III)

                                        (SEQ ID NO: 87)
P67: GGGTAACGGCCAGTGTGTCTTAGAAAATG

                                        (SEQ ID NO: 88)
P68: CTAAGACACACTGGCCGTTACCCTGCGAA

                                        (SEQ ID NO: 89)
P69: TTGTCCTCCTTTTGTATGTCCTCCTGGACT

                                        (SEQ ID NO: 90)
P70: GGAGGACATACAAAAGGAGGACAACCTTGACCACCTTGACGCTG

                                        (SEQ ID NO: 91)
P71: CGCGGATCCAAGCGATCTCAGTGTTGT(BamH I)

                                        (SEQ ID NO: 92)
P72: TGTGACCCGCTACCCGATAA

                                        (SEQ ID NO: 93)
P73: CGTTACCCTGCGAATGTC
```

The homologous recombinant plasmid pK18mobsacB-$P_{sod}$::$P_{prsA}$ identified through sequencing is electronically transformed into L-histidine recombinant bacteria CG161. The kanamycin resistance screening is employed to obtain the bacterial colony that the recombinant plasmid is integrated on the chromosome and the sugar screening is employed to obtain the positive bacterial colony after two homologous recombinations. The positive bacterial colony is identified through PCR amplification with P72 and P65 as the primers to obtain 778 bp being the recombinant bacteria WT-$P_{glyA}$::$P_{hisEG}$-hiSG$^{fbr}$-$P_{glyA}$::$P_{hisDCB}$-$P_{sod}$::$P_{prsA}$-Δpgi and named as CG350.

The homologous recombinant plasmid pK18mobsacB-$P_{eftu}$::$P_{tkt}$ identified through sequencing is electronically transformed into *Corynebacterium glutamicum* CG350 and the kanamycin resistance screening is employed to obtain the bacterial colony that the recombinant plasmid is integrated on the chromosome and the sugar screening is employed to obtain the positive bacterial colony after two homologous recombinations. The positive bacterial colony is identified through PCR amplification with P73 and P71 as the primers to obtain 874 bp of the recombinant bacteriaWT-$P_{glyA}$::$P_{hisEG}$-his$G^{fbr}$-$P_{glyA}$::$P_{hisDCB}$-$P_{eftu}$::$P_{tkt}$-$P_{sod}$::$P_{prsA}$Δpgi and name it as *Corynebacterium glutamicum* CG351.

The genome DNA of the recombinant bacterium is extracted and sequenced. The result proves that the promoters of the operon tkt-tal-zwf-opcA-devB and the gene prsA in L-histidine recombinant bacteria CG161 are respectively replaced with the endogenous strong promoter $P_{eftu}$ and $P_{sod}$ in *Corynebacterium glutamicum*, L-histidine recombinant bacteria CG351 containing no plasmid (WT-$P_{glyA}$::$P_{hisEG}$-his$G^{fbr}$-$P_{glyA}$::$P_{hisDCB}$-$P_{eftu}$:$P_{tkt}$-$P_{sod}$::$P_{prsA}$-Δpgi) is constructed successfully.

Embodiment 6: Construction of L-Histidine High-Yield Recombinant Bacteria CG352 and CG353 Containing No Plasmid In this embodiment, on the basis of Embodiment 5 as above, the promoter of the gene purH is replaced with the strong promoter $P_{eftu}$ in order to enhance the expression of the bifunctional enzyme AICAR transmethylase I IMP ring hydrase (PurH, SEQ ID NO: 16) encoded by purH and hence further construct CG352; then the promoter of the gene purF is replaced with the promoter $P_{hom}$ in order to weaken the first enzyme in the synthetic pathway of nucleotide-amidophosphoribosyl transterase (PurF, SEQ ID NO: 19) and hence construct CG353.

The method same as that in Embodiment 5 as above is employed to construct the homologous recombinant plasmid pK18mobsacB-$P_{eftu}$::$P_{purH}$ and replace the promoter of the gene purH with the strong promoter $P_{eftu}$. The primer is designed according to the upstream and downstream sequences of the gene purH of *Corynebacterium glutamicum ATCC*13032 in Genbank. The genome DN of *Corynebacterium glutamicum* ATCC13032 is used as the template with P74 and P75 as the primers to carry out amplification and obtain the promoter $P_{etfu}$. P76 and P77 are used as the primers to carry out amplification and obtain the upstream homologous arm. P78 and P79 are used as the primers to carry out amplification and obtain the downstream homologous arm. Then the PCR product as above is purified and used as the template with P76 and P79 as the primers to carry out amplification with the technique of overlap extension PCR (SOE) and obtain 1473 bp of segment (SEQ ID NO: 20) containing the upstream and downstream homologous arms and the promoter $P_{eftu}$, wherein: No. 1-633 nucleotides of 5' end in SEQ ID NO: 20 is the upstream homologous arm, No. 634-833 nucleotides of 5' end in SEQ ID NO: 20 is $P_{eftu}$, No. 834-1473 nucleotides of 5' end in SEQ ID NO: 20 is the downstream homologous arm.

After double-enzyme digestion by Xba I and Sma I, the PCR product of 1473 bp as above connects with the homologous recombinant vector pK18mobsacB after the same double-enzyme digestion. The connection product is transformed through chemical method into *Escherichia coli* DH5α and the transformant is screened on LB plate containing kanamycin (50 μg/mL). After the transformant is sub-cultured three generations, P13 and P14 are used as the primers and the colony PCR is employed to identify the transformant and obtain 1685 bp being the positive transformant. The plasmid of the transformant after identified is extracted and identified through double-enzyme digestion by Xba I and Sma I and obtain 1473 bp being positive.

The positive plasmid is sequenced and the result shows that this plasmid is the recombinant plasmid obtained through inserting the nucleotide as shown by SEQ ID NO: 20 in the sequence table into the vector pK18mobsacB and named as pK18mobsacB-$P_{eftu}$::$P_{purH}$.

```
                                    (SEQ ID NO: 94)
P74: CTGGAGAGGCTAATGGCCGTTACCCTGCGAA

                                    (SEQ ID NO: 95)
P75: ATCATCGCTCATTGTATGTCCTCCTGGACT

                                    (SEQ ID NO: 96)
P76: GCTCTAGAATGATGGTTCCGAGGCCG (Xba I)

                                    (SEQ ID NO: 97)
P77: GGGTAACGGCCATTAGCCTCTCCAGTTGAG

                                    (SEQ ID NO: 98)
P78: GGAGGACATACAATGAGCGATGATCGTAAG

                                    (SEQ ID NO: 99)
P79: TCCCCCGGGTGGTGCCGATCCAACCTG(Sma I)
```

The homologous recombinant plasmid pK18mobsacB-$P_{eftu}$::$P_{purH}$ identified through sequencing is electronically transformed into the L-histidine recombinant engineering bacteria CG351. The kanamycin resistance screening is employed to obtain the bacterial colony that the recombinant plasmid is integrated on the chromosome and the sugar screening is employed to obtain the positive bacterial colony after two homologous recombinations. The genome DNA of the positive colony is extracted and used as the template with P74 and P79 as the primers to carry out PCR amplification and obtain 840 bp being the positive clone. The sequencing verifies that the promoter of the gene purH in the L-histidine recombinant bacteria CG351 is successfully replaced with the endogenous strong promoter $P_{eftu}$ in *Corynebacterium glutamicum*, L-histidine recombinant bacteria CG352 containing no plasmid (WT-$P_{glyA}$::$P_{hisEG}$-hiS$G^{fbr}$-$P_{glyA}$::$P_{hisDCB}$-$P_{eftu}$::$P_{tkt}$-$P_{sod}$::$P_{prsA}$-Δpgi-$P_{etfu}$::$P_{purH}$) is constructed successfully.

Figure 8:
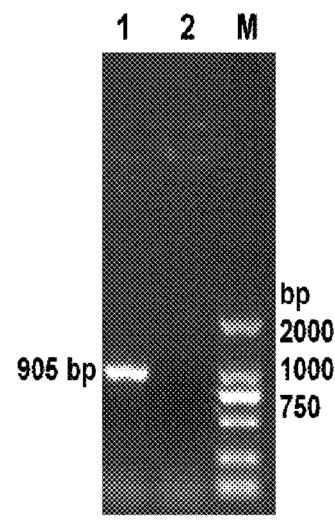
FIG. 8 is the electro-phoretogram of PCR identification of the genome DNA of the bacterial strain CG353 (gene purF is weakened).

The homologous recombinant plasmid pK18mobsacB-$P_{hom}$::$P_{purF}$ identified through sequencing prepared in Embodiment 4 is electronically transformed into *Corynebacterium glutamicum* CG352. The Kanamycin resistance forward screening is employed to obtain the bacterial colony that the recombinant plasmid is integrated on the chromosome and the sugar inverse screening is employed to obtain the bacterial colony after a second homologous recombination. P56 and P59 are used as the primers to extract the genome DNA of the colony and carry out identification through PCR amplification. 905 bp is obtained to be positive (see FIG. 8) and named as CG353 (WT-$P_{glyA}$::$P_{hisEG}$-hiS$G^{fbr}$-$P_{glyA}$::$P_{hisDCB}$-$P_{eftu}$::$P_{tkt}$-$P_{sod}$::$P_{prsA}$-Δpgi-$P_{eftu}$::$P_{purH}$-$P_{hom}$::$P_{purF}$). CG353 is further sequenced and analyzed. The result shows that the promoter of the gene purF of the chromosome of the engineering bacteria CG352 is replaced with $P_{hom}$ and CG353 is constructed successfully.

Embodiment 7: Application of L-Histidine Engineering Bacteria in Production of L-Histidine 1. Fermentation of High-Yield L-Histidine Recombinant Bacteria Containing Plasmid 1. Flask-Shaking Fermentation of High-Yield L-Histidine Recombinant Bacteria Containing Plasmid The details of fermentation medium used in flask shaking are as follows: glucose 40 g/L, $(NH_4)_2SO_4$ 20 g/L, $KH_2PO_4$ 0.5 g/L, $K_2HPO_4.3H_2O$ 0.5 g/L, $MgSO_4.7H_2O$ 0.25 g/L, $FeSO_4.7H_2O$ 0.01 g/L, $MnSO_4.H_2O$ 0.01 g/L, $ZnSO_4.7H_2O$ 0.001 g/L, $CuSO_4$ 0.0002 g/L, $NiCl_2.6H_2O$ 0.00002 g/L, biotin 0.0002 g/L, pH 7.0-7.2, $CaCO_3$ 20 g/L. The glucose is autoclaved separately at 115° C. for 15 minutes. $MgSO_4.7H_2O$ and inorganic ions are autoclaved separately at 121° C. for 20 minutes. The vitamin is sterilized through filtration by 0.22 μm sterile membrane. Other ingredients are autoclaved in 121° C. for 20 minutes.

The details of seed medium are as follows: glucose 20 g/L, $(NH_4)_2SO_4$ 5 g/L, $K_2HPO_4.3H_2O$ 1 g/L, $MgSO_4.7H_2O$ 0.4 g/L, biotin 50 μg, Vitamin $B_1$ 1 mg, Angel yeast powder (FM802) 10 g/L, Angel peptone (FP318) 10 g/L.

1) Obtaining Seed Solution

The engineering bacteria CG176, CG172, CG173 and CG171 prepared in Embodiment 2 as above are respectively inoculated into seed solution. The culture temperature of seed solution is 32° C. The rotation speed of shaker is 220 r/min. The incubation time is 8 h. $OD_{600}$ is 20.

2) Fermentation

The seed solution is inoculated by volume percentage as 3% into the fermentation medium containing chlorampenicol with final concentration of 10 μg/ml (30 mL solution in 500 mL baffled flask) and cultured at 32° C. and 220 r/min for 72 h. After fermented and cultured for 6 h, isopropyl-beta-D-thiogalactopyranoside (IPTG) with final concentration of 1 mmol/L is added to induce the expression of target gene. The strong ammonia water is added intermittently to control pH of fermentation solution to 7.0-7.2. As per the residual sugar, 400 g/L glucose mother liquid is added to control the residual sugar in fermentation solution to 5-10 g/L.

Fermentation product is collected and centrifuged at 12000×g for 5 minutes and then the supernatant is collected.

3) Test the Content of L-Histidine

HPLC is used and the details of test are as follows (2,4-DNFB pre-column derivation HPLC): take 50 μL the supernatant as above in 2 mL centrifuge tube and add 200 μL $NaHCO_3$ aqueous solution (0.5 mol/L, pH 9.0) and 100 μL 1% of 2,4-DNFB-acetonitrile solution (volume ratio). Heat it in the dark in a water bath at 60° C. for 60 min, then cool it to 25° C. Add 650 μL $KH_2PO_4$ aqueous solution (0.01 mol/L, pH 7.2±0.05, adjust pH with NaOH aqueous solution). Keep still for 15 min and then filter before injection. The injection size is 15 μL.

The chromatographic columns used are C18 columns (ZORBAX Eclipse XDB-C18, 4.6*150 mm, Agilent, USA); column temperature: 40° C.; UV detection wavelength: 360 nm; mobile phase A is 0.04 mol/L $KH_2PO_4$ aqueous solution (pH 7.2±0.05, adjust pH with 40 g/L KOH aqueous solution), mobile phase B is 55% acetonitrile aqueous solution (volume ratio). Flow rate of mobile phase is 1 mL/min. The elution process is as shown in Table 1 below:

TABLE 1

| Duration (min) | Mobile A (%) | Mobile B (%) |
|---|---|---|
| 0 | 86 | 14 |
| 2 | 88 | 12 |
| 4 | 86 | 14 |
| 10 | 70 | 30 |
| 20 | 30 | 70 |
| 21 | 10 | 90 |
| 24 | 0 | 100 |

With the wild type of strain *C. glutamicum* ATCC13032 as the control, the glucose consumption, $OD_{600}$ and the final L-histidine yield during fermentation process are determined. The result is shown as in Table 2.

Table 2 shows the glucose consumption, maximum $OD_{600}$, specific growth rate and L-histidine yield by the L-histidine engineering bacteria CG160, CG176, CG172, CG173 and CG171 during flask-shaking test.

TABLE 2

| Strain | Glucose consumption (g) | Maximum $OD_{600}$ | Specific growth rate ($h^{-1}$) | L-histidine yield (g/L) |
|---|---|---|---|---|
| CG160 | 3.8 | 62.67 | 0.131 | 0.03 |
| CG176 | 3.8 | 60.97 | 0.127 | 1.18 |
| CG172 | 1.2 | 46.67 | 0.073 | 0.77 |
| CG173 | 3.8 | 59.07 | 0.120 | 1.50 |
| CG171 | 1.8 | 53.83 | 0.108 | 2.40 |

During the flask-shaking tests, after fermentation for 72 h, no L-histidine accumulation is measured for the wild type of *C. glutamicum* ATCC13032 and L-histidine yield by the base bacteria CG160 is 0.03 g/L. L-histidine yield by the base engineering bacteria CG176 that only L-histidine terminal metabolic pathway is modified is 1.18 g/L. On this basis, L-histidine yield by the engineering bacteria CG172 with only deletion of the gene pgi is 0.77 g/L and L-histidine yield by the engineering bacteria CG173 with only over-expression of zwf-opcA is 1.50 g/L. L-histidine yield by the engineering bacteria CG171 with both deletion of the gene pgi and over-expression of zwf-opcA is 2.40 g/L and increased by 2.1 times than that by the engineering bacteria CG172 with only deletion of the gene pgi, by 60% than that by the engineering bacteria CG173 with only over-expression of the gene zwf-opcA, and by 102% than that by the engineering bacteria CG176 that only the terminal metabolic pathway of L-histidine is modified.

2. L-Histidine Engineering Bacteria CG171, CG319 and CG328 Fermentation Tank Produce L-Histidine in Fermentor The details of the seed medium are as follows: glucose 20 g/L, $(NH_4)_2SO_4$ 5 g/L, $K_2HPO_4.3H_2O$ 1 g/L, $MgSO_4.7H_2O$ 0.9 g/L, biotin 50 μg, Vitamin $B_1$ 1 mg, Angel yeast powder (FM802) 2 g/L, Angel peptone (FP318) 2 g/L.

The details of the fermentation medium are as follows: glucose 20 g/L, $(NH_4)_2SO_4$ 5 g/L, $K_2HPO_4$ 0.5 g/L, $K_2HPO_4.3H_2O$ 0.5 g/L, $MgSO_4.7H_2O$ 0.25 g/L, $FeSO_4.7H_2O$ 10 mg/L, $MnSO_4.H_2O$ 10 mg/L, Vitamin $B_1$ 0.5 mg, Angel yeast powder (FM802) 5 g/L.

1) Obtaining Seed Solution

The engineering bacteria CG171, CG319 and CG328 are inoculated into the seed medium. The seed solution is cultured at 32° C. for 8 h with the rotation speed of shaker being 220 r/min to give a seed solution of $OD_{600}$ as 20.

2) Fermentation

The seed solution is inoculated by volume percentage as 10% into the fermentation medium containing chlorampenicol with a final concentration of 10 μg/ml.

7.5 L fermentor is used (BioFlo115, NBS): it is builtin with constant-speed programmable-controlled bump to realize constant-speed feed supplement. During the process of fermentation, a peristaltic pump is used to supplement 600 g/L glucose and control the concentration of glucose in fermentation system to 5-10 g/L. 10 g/L Angel yeast powder (FM802) is dripped in simultaneously. Heating jacket and cooling water are used to control the fermentation temperature at 32° C. Air is introduced to supply dissolved oxygen which is controlled to 30% though cascade control between the rotation speed and dissolved oxygen signal. Strong ammonia water is added to regulate pH and keep it at about 6.9. The fermentation is run continuously for 52 h. When $OD_{600}$=4-5, IPTG (isopropyl thiogalactopyranoside is added with final concentration of 0.5 mmol/L) to induce the expression of the gene carried by recombinant plasmid.

The fermentation product is collected and centrifuged at 12000×g for 5 min to collect the supernatant.

3) Test the Content of L-Histidine

L-histidine content in the supernatant is determined according to the method described in 3) of 1 above and the result is shown as follows: the highest yield of L-histidine by the engineering bacteria CG171 is 10.87 g/L, the production intensity is 0.21 g/L/h; the highest yield of L-histidine by the engineering bacteria CG319 is 14.15 g/L, the production intensity is 0.30 g/Uh; the highest yield of L-histidine by the engineering bacteria CG328 is 15.96 g/L and the production intensity is 0.32 g/L/h. See the result in Table 3.

TABLE 3

| Strain | Histidine yield (g/L) | Fermentation duration (h) |
| --- | --- | --- |
| CG171 | 10.87 | 52 |
| CG319 | 14.15 | 47 |
| CG328 | 15.96 | 50 |

As shown in the table above, the fermentor tests show that CG171 achieves a very good result and the Histidine yield amounts to 10.87 g/L after fermentation for 52 h. Compared with CG171, the engineering bacteria CG319 with further over-expression of purH and the engineering bacteria CG328 with both further over-expression of purH and weakening purF respectively produce about 30% and 50% more histidine in shorter fermentation duration. That is, on the basis of weakening pgi and over-expression of zwf-opcA, the histidine synthetic pathway and the nucleotide synthetic pathway are coupled to promote the metabolic flux of histidine synthetic pathway and further improve the histidine yield greatly.

2. L-Histidine Engineering Bacteria CG350, CG351, CG352 and CG353 Containing No Plasmid Produce L-Histidine Through Flask-Shaking Obtaining seed solution of the engineering bacteria CG350, CG351, CG352 and CG353 as well as the flask-shaking fermentation method are the same as those described in 1 as above. The difference is that no chloramphenicol and inducer IPTG is needed during the fermentation process. The test of L-histidine content is the same as that described in 1 of this embodiment. The wild type of *C. glutamicum* ATCC13032 is used as the control. During the flask-shaking tests, after fermentation for 72 h, no accumulation of L-histidine is detected for the wild type of strain *C. glutamicum* ATCC13032. L-histidine yield by the engineering bacteria CG350 constructed through single deletion of the gene pgi is 0.65 g/L. On this basis, the engineering bacteria CG351 constructed with also improved expression quantity of zwf-opcA has a L-histidine yield of 1.86 g/L and increases by 186% than that by the engineering bacteria CG350 with single deletion of the gene pgi. L-histidine yield by the strain CG352 with further improved expression of the gene purH is 2.23 g/L and L-histidine yield by the strain CG353 with further decreased expression of the gene purF is 2.34 g/L. See the result in Table 4.

TABLE 4

| Strain | Histidine yield (g/L) |
| --- | --- |
| Wild type | — |
| CG350 | 0.65 |
| CG351 | 1.86 |
| CG352 | 2.23 |
| CG353 | 2.34 |

The invention claimed is:

1. A recombinant bacteria producing L-amino acid(s), said recombinant bacteria has reduced expression of the glucose-6-phosphate isomerase gene pgi and improved expression of the glucose-6-phosphate dehydrogenase gene zwf-opcA than the starting bacteria, wherein: said starting bacterium is a bacterial strain that can accumulate target amino acid(s) and preferably, said amino acid is L-histidine, wherein, the gene pgi on the chromosome of the recombinant bacterium has been inactivated, preferably knocked out or the regulatory element of the gene pgi has been replaced with a regulatory element with low transcription or low expression activity, also said recombinant bacteria has two or more copied genes zwf-opcA, or the promoter of the operon tkt-tal-zwf-opcA-devB on the chromosome of said starting bacterium is replaced with a strong promoter, preferably, said strong promoter is the promoter $P_{eftu}$, of the original bacteria.

2. The recombinant bacteria according to claim 1, wherein: said starting bacteria has enhanced expression of the genes hisEG and hisDCB of the operon for L-histidine synthesis than the original bacteria, preferably a strong promoter is used to replace the promoter of said genes hisEG and hisDCB, more preferably, the promoter $P_{glyA}$ on the chromosome of said original bacteria replaces respectively the promoters of the genes hisEG and hisDCB, further preferably, said starting bacteria has enhanced expression of PRPP synthetase PrsA than the original bacteria, more preferably, said starting bacteria has two or more copied gene prsA or a strong promoter replaces the promoter of the gene prsA, preferably, said strong promoter is the promoter $P_{sod}$ of said original bacteria.

3. The recombinant bacteria according to claim 2, wherein: said recombinant bacteria has enhanced expression of AICAR transmethylase/IMP ring hydrase PurH than said starting bacteria, preferably, said recombinant bacteria has two or more copied genes purH, or the promoter of the gene purH is replaced with a strong promoter, more preferably, said strong promoter is the promoter $P_{eftu}$ of said original bacteria.

4. The recombinant bacteria according to claim 3, wherein:

said recombinant bacteria has weakened expression of the amidophosphoribosyl transterase PurF than said starting bacteria, preferably, the promoter of the gene purF is replaced with a weak promoter, more preferably, said weak promoter is the promoter $P_{hom}$ in said original bacteria.

5. The recombinant bacteria according to claim 4, wherein:

said original bacterium is a bacterial strain selected from *corynebacterium, dialister* or *brevibacterium*, preferably, said bacteria of *corynebacterium* is a bacterial strain selected from *Corynebacterium glutamicum, Corynebacterium pekinense, Corynebacterium efficiens, Corynebacterium crenatum, Corynebacterium thermoaminogenes, Corynebacterium aminogenes, Corynebacterium lilium, Corynebacterium callunae* and *Corynebacterium herculis,* said bacteria of *dialister* is a bacterial strain selected from *Microbacterium ammoniaphilum*, and said bacteria of *brevibacterium* is a bacterial strain selected from *Brevibacteriaceae flvum, Brevibacteriaceae lactofermentum* and *Brevibacteriaceae ammoniagenes*; more preferably, said original bacterium is the wild type of *Corynebacterium glutamicum* ATCC13032.

6. The recombinant bacteria according to claim 5, wherein:

the chromosome of said starting bacteria has the promoter $P_{glyA}$ as shown by nucleotides 863-1038 in the 5' end of the nucleotide sequence of SEQ ID NO: 7 used to replace respectively the promoters of the operons hisEG and hisDCB for L-histidine synthesis on the chromosome of said *Corynebacterium glutamicum* ATCC13032, and said starting bacteria can express the mutated ATP-phosphoribosyl transferase, said mutated ATP-phosphoribosyl transferase is the enzyme of ATP-phosphoribosyl transferase as shown by SEQ ID NO: 6 whose No. 215 asparagine is mutated to lysine, No. 231 leucine to phenylalanine and No. 235 threonine to alanine, preferably, the chromosome of said starting bacteria has a gene $hisG^{fbr}$ as shown by nucleotides 1007-1852 in the 5' end of the nucleotide sequence of SEQ ID NO: 4 used to replace the gene hisG on the chromosome of said *Corynebacterium glutamicum* ATCC13032, preferably, the chromosome of said starting bacteria has the promoter $P_{sod}$ as shown by nucleotides 656-847 in the 5' end of the nucleotide sequence of SEQ ID NO: 11 used to replace the promoter of the gene prsA on the chromosome of said *Corynebacterium glutamicum* ATCC13032, or, said starting bacteria has two or more copied genes prsA and $hisG^{fbr}$, wherein, said gene prsA is, or at least 99% homologous with, the nucleotides 15-992 in the 5' end of the nucleotide sequence as shown by SEQ ID NO: 4 in the sequence table.

7. The recombinant bacteria according to claim 6, wherein: said gene pgi is, or at least 99% homologous with, the nucleotide sequence as shown by SEQ ID NO: 13, said genezwf-opcA is, or at least 99% homologous with, the nucleotide sequence as shown by SEQ ID NO: 2 and said promoter Peftu is nucleotides 635-834 in the 5' end of the nucleotide sequence of SEQ ID NO: 12.

8. The recombinant bacteria according to claim 7, wherein: said gene purH is, or at least 99% homologous with, the nucleotide sequence as shown by SEQ ID NO: 15.

9. The recombinant bacteria according to claim 8, wherein: said promoter $P_{hom}$ is nucleotides 736-865 in the 5' end of the nucleotide sequence of SEQ ID NO: 18.

10. A method of constructing the recombinant bacteria capable of producing L-histidine, which comprises the following steps: reduce the expression of the glucose-6-phosphate isomerase Pgi in the starting bacteria and improve the expression of the glucose-6-phosphate dehydrogenase Zwf-OpcA in said starting bacteria to obtain said recombinant bacteria, wherein: said starting bacterium is a bacterial strain which can accumulate target amino acid(s), more preferably, said target L-amino acid.

11. The method according to claim 10, wherein:

said reducing the expression of Pgi in starting bacterium is realized by means of the following A) or B):

A) Inactivate the gene pgi of the chromosome of said starting bacteria; said inactivation is preferably knocking out, B) Replace the regulatory element of the gene pgi in said starting bacteria with a regulatory element of low transcription and low expression activity, and said improving the expression of Zwf-OpcA in said starting bacterium is realized by means of the following C) or D):

C) Increase the copy number of the gene zwf-opcA in said starting bacteria,

D) Replace the promoter of the operon tkt-tal-zwf-opcA-devB on the chromosome of said starting bacteria with a strong promoter, preferably, said strong promoter is the promoter $P_{eftu}$ on the chromosome of said original bacteria.

12. The method according to claim 10, wherein: obtaining said starting bacteria comprises the step(s) of replacing the promoter of the operon hisEG and hisDCB for L-histidine synthesis on the chromosome of starting bacteria respectively with a strong promoter, preferably, said strong promoter is the promoter $P_{glyA}$ on the chromosome of said original bacteria, preferably, obtaining said starting bacteria further comprises the step(s) of improving the expression of PRPP synthetase PrsA in said starting bacteria, more preferably, said improving the expression of PrsA in said starting bacterium is realized by means of the following E) or F):

E) Increase the copy number of the gene prsA in said starting bacteria,

F) Replace the promoter of the gene prsA on the chromosome of said starting bacteria with a strong promoter, preferably, said strong promoter is the promoter $P_{sod}$ on the chromosome of said original bacteria.

13. The method according to claim 12, wherein: said method further comprises the step(s) of improving the expression of AICAR transmethylase/IMP ring hydrase PurH in said recombinant bacteria, preferably, said improving the expression of PurH in said recombinant bacterium is realized by means of the following G) or H):

G) Increase the copy number of the gene purH in said starting bacteria,

H) Replace the promoter of the gene purH on the chromosome of said starting bacteria with a strong promoter, preferably, said strong promoter is the promoter $P_{eftu}$ on the chromosome of said original bacteria.

14. The method according to claim 13, wherein: said method further comprises the step(s) of weakening the expression of the amidophosphoribosyl transterase PurF in said recombinant bacteria, preferably, said weakening the expression of PurF in said recombinant bacterium is realized through replacing the promoter of the gene purF with a weak promoter, more preferably, the promoter of the gene purF on the chromosome in said starting bacterium is replaced with the promoter $P_{hom}$ on the chromosome in said original bacteria.

15. The method according to claim 14, wherein: the original bacteria used to obtain said starting bacterium is a bacterial strain selected from *corynebacterium, dialister* or *brevibacterium*, preferably, said bacteria of *corynebacterium* is a bacterial strain selected from *Corynebacterium glutamicum, Corynebacterium pekinense, Corynebacterium efficiens, Corynebacterium crenatum, Corynebacterium thermoaminogenes, Corynebacterium aminogenes, Corynebacterium lilium, Corynebacterium callunae* and *Corynebacterium herculis*, said bacteria of *dialister* is a bacterial strain selected from *Microbacterium ammoniaphilum*, and said bacteria of *brevibacterium* is a bacterial strain selected from *Brevibacteriaceae flvum, Brevibacteriaceae lactofermentum* and *Brevibacteriaceae ammoniagenes*, more preferably said original bacterium is the wild type of *Corynebacterium glutamicum* ATCC13032.

16. The method according to claim 15, wherein: the following steps are comprised to obtain said starting bacteria:

replace the promoter of the operon hisEG and hisDCB for L-histidine synthesis on the chromosome of *Corynebacterium glutamicum* ATCC13032 respectively with the promoter $P_{glyA}$ as shown by nucleotides 863-1038 in the 5' the nucleotide sequence of SEQ ID NO: 7, and mutate No. 215 asparagine to lysine, No. 231 leucine to phenylalanine and No. 235 threonine to alanine on ATP-phosphoribosyl transferase expressed by said *Corynebacterium glutamicum* ATCC13032 as shown in SEQ ID NO: 6, preferably, the gene used to carry out the mutations as above is the gene $hisG^{fbr}$ as shown by nucleotides 1007-1852 in the 5' end of the nucleotide sequence of SEQ ID NO: 4, preferably, obtaining said starting bacteria further comprises the following steps:

replace the promoter of the gene prsA on the chromosome of said *Corynebacterium glutamicum* ATCC13032 with the promoter $P_{sod}$ as shown by nucleotides 656-847 in the 5' end if the nucleotide sequence of SEQ ID NO: 11, or, the following steps are further comprised:

Increase the copy number of the gene prsA in said *Corynebacterium glutamicum* ATCC13032 and increase the copy number the gene $hisG^{fbr}$ in said *Corynebacterium glutamicum* ATCC13032, wherein, said gene prsA is, or at least 99% homologous with, the nucleotides 15-992 in the 5' end of the nucleotide sequence as shown by SEQ ID NO: 4 in the sequence table.

17. The method according to claim 16, wherein: said gene pgi, or at least 99% homologous with, the nucleotide sequence as shown by SEQ ID NO: 13, said gene zwf-opcA is, or at least 99% homologous with, the nucleotide sequence as shown by SEQ ID NO: 2 and said promoter Peftu is nucleotides 635-834 in the 5' end of the nucleotide sequence of SEQ ID NO: 12, and said promoter $P_{eftu}$ is nucleotides 635-834 in the 5' end of the nucleotide sequence of SEQ ID NO: 12.

18. A method according to claim 17, wherein: said gene purH is, or at least 99% homologous with, the nucleotide sequence as shown by SEQ ID NO: 15.

19. The method according to claim 18, wherein: said promoter $P_{hom}$ is nucleotides 736-865 in the 5' end of the nucleotide sequence of SEQ ID NO: 18.

20. A method of constructing recombinant bacteria of claim 1, which comprises the step(s) of fermenting and culturing a recombinant bacteria.

* * * * *

SEQUENCE LISTING

```
<160> NUMBER OF SEQ ID NOS: 99

<210> SEQ ID NO 1
<211> LENGTH: 1672
<212> TYPE: DNA
<213> ORGANISM: Artificial Sequence
<220> FEATURE:
<223> OTHER INFORMATION: Synthesized

<400> SEQUENCE: 1

gctctttcgg agtgaccttc tccccagacg gaaccgccga aatcggagcc tccgtcgatg      60

ctgtggacgg gcacatcatc aacgacgccg tcacccaaca cgcgaagaaa aacgacctca     120

cctacggcga agctttcagc gacatccttc ggaacaatat ccaagtcaag gtagtcctca     180

acttgtacac cgccaaagac ctcgccaacg ccccagtgtg ggccagcgga atcggctggt     240

tggatgccaa gactggaaca ttctggtcag agaaagccaa caaagaacaa gacatggatg     300

cggctgccaa aatcagcacc gacaaacacg atcctccacc agcgttgcgt gacgcactca     360

ttggtcgtga tggcacctgc cgattccctg gctgttcagt cccagcgctc aaaacccaag     420

ccgaccaccg catcccctac gaagaaggcg gagaaacttg cctaggcgga atcggctgcc     480

tctgtcaaca ccaccacaac atgaaaaccg acggccgagt cacctacctt ctcgatccct     540

tctccggcat catcgtctgg ctcatgggag acggaacatg ggcagtgtca gaacccaacg     600
```

```
ggccgctcaa tcccaaaaat gcgagatggg cgcaaacagt cgcccaacac cgggcacgcc    660

accacaagcg ttgggttaag gaggacgcca agtagccgga tggccacgtc gaaaagcagc    720

ccaataaacg cacctaaatt tgtcgtgttt cccactttga acactcttcg atgcgcttgg    780

ccacaaaagc aagctaacct gaagatgtta tttaacgaca ataaaggagt tttctcgctt    840

gcttataggg tcaggggcgt gaagaatcct cgcctcatag cactggccgc tatcatcctg    900

acctcgttca atctgcgaac agctattact gctttagctc cgctggtttc tgagattcgg    960

gatgatttag ggttagtgc ttctcttatt ggtgtgttgg gcatgatccc gactgctatg    1020

ttcgcggttg ctgcgtttgc gcttccgtcg ttgaagagga agttcactac ttcccaactg   1080

ttgatgtttg ccatgctgtt gactgctgcc ggtcagatta ttcgtgtcgc tggacctgct   1140

tcgctgttga tggtcggtac tgtgttcgcg atgtttgcga tcggagttac caatgtgttg   1200

cttccgattg ctgttaggga gtattttccg cgtcacgtcg gtggaatgtc gacaacttat   1260

ctggtgtcgt tccagattgt tcaggcactt gctccgacgc ttgccgtgcc gatttctcag   1320

tgggctacac atgtggggtt gaccggttgg agggtgtcgc tcggttcgtg ggcgctgctg   1380

gggttggttg cggcgatttc gtggattccg ctgttgagtt tgcagggtgc cagggttgtt   1440

gcggcgccgt cgaaggtttc tcttcctgtg tggaagtctt cggttggtgt ggggctcggg   1500

ttgatgtttg ggtttacttc gtttgcgacg tatatcctca tgggttttat gccgcagatg   1560

gtaggtgatc ctcagctcgg tgcggtgttg ttaggctggt ggtcaatttt gggattgccg   1620

ctgaacattc tgggaccgtg gttggtgacg cgtttcacta actgcttccc ga           1672
```

```
<210> SEQ ID NO 2
<211> LENGTH: 2519
<212> TYPE: DNA
<213> ORGANISM: Corynebacterium glutamicum

<400> SEQUENCE: 2

atgagcacaa acacgacccc ctccagctgg acaaacccac tgcgcgaccc gcaggataaa      60

cgactccccc gcatcgctgg cccttccggc atggtgatct tcggtgtcac tggcgacttg     120

gctcgaaaga agctgctccc cgccatttat gatctagcaa accgcggatt gctgcccccca    180

ggattctcgt tggtaggtta cggccgccgc gaatggtcca aagaagactt tgaaaaatac     240

gtacgcgatg ccgcaagtgc tggtgctcgt acggaattcc gtgaaaatgt ttgggagcgc     300

ctcgccgagg gtatggaatt tgttcgcggc aactttgatg atgatgcagc tttcgacaac     360

ctcgctgcaa cactcaagcg catcgacaaa acccgcggca ccgccggcaa ctgggcttac     420

tacctgtcca ttccaccaga ttccttcaca gcggtctgcc accagctgga gcgttccggc     480

atggctgaat ccaccgaaga agcatggcgc cgcgtgatca tcgagaagcc tttcggccac     540

aacctcgaat ccgcacacga gctcaaccag ctggtcaacg cagtcttccc agaatcttct     600

gtgttccgca tcgaccacta tttgggcaag gaaacagttc aaaacatcct ggctctgcgt     660

tttgctaacc agctgtttga gccactgtgg aactccaact acgttgacca cgtccagatc     720

accatggctg aagatattgg cttgggtgga cgtgctggtt actacgacgg catcggcgca     780

gcccgcgacg tcatccagaa ccacctgatc cagctcttgg ctctggttgc catggaagaa     840

ccaatttctt tcgtgccagc gcagctgcag gcagaaaaga tcaaggtgct ctctgcgaca     900

aagccgtgct acccattgga taaaacctcc gctcgtggtc agtacgctgc cggttggcag     960

ggctctgagt tagtcaaggg acttcgcgaa gaagatggct tcaaccctga gtccaccact    1020

gagacttttg cggcttgtac cttagagatc acgtctcgtc gctgggctgg tgtgccgttc    1080
```

```
tacctgcgca ccggtaagcg tcttggtcgc cgtgttactg agattgccgt ggtgtttaaa   1140

gacgcaccac accagccttt cgacggcgac atgactgtat cccttggcca aaacgccatc   1200

gtgattcgcg tgcagcctga tgaaggtgtg ctcatccgct tcggttccaa ggttccaggt   1260

tctgccatgg aagtccgtga cgtcaacatg gacttctcct actcagaatc cttcactgaa   1320

gaatcacctg aagcatacga gcgcctcatt ttggatgcgc tgttagatga atccagcctc   1380

ttccctacca acgaggaagt ggaactgagc tggaagattc tggatccaat tcttgaagca   1440

tgggatgccg atggagaacc agaggattac ccagcgggta cgtggggtcc aaagagcgct   1500

gatgaaatgc tttcccgcaa cggtcacacc tggcgcaggc cataatttag ggcaaaaaa    1560

tgatctttga acttccggat accaccaccc agcaaatttc caagacccta actcgactgc   1620

gtgaatcggg cacccaggtc accaccggcc gagtgctcac cctcatcgtg gtcactgact   1680

ccgaaagcga tgtcgctgca gttaccgagt ccaccaatga agcctcgcgc gagcacccat   1740

ctcgcgtgat cattttggtg gttggcgata aaactgcaga aaacaaagtt gacgcagaag   1800

tccgtatcgg tggcgacgct ggtgcttccg agatgatcat catgcatctc aacggacctg   1860

tcgctgacaa gctccagtat gtcgtcacac cactgttgct tcctgacacc cccatcgttg   1920

cttggtggcc aggtgaatca ccaaagaatc cttcccagga cccaattgga cgcatcgcac   1980

aacgacgcat cactgatgct ttgtacgacc gtgatgacgc actagaagat cgtgttgaga   2040

actatcaccc aggtgatacc gacatgacgt gggcgcgcct tacccagtgg cggggacttg   2100

ttgcctcctc attggatcac ccaccacaca gcgaaatcac ttccgtgagg ctgaccggtg   2160

caagcggcag tacctcggtg gatttggctg caggctggtt ggcgcggagg ctgaaagtgc   2220

ctgtgatccg cgaggtgaca gatgctccca ccgtgccaac cgatgagttt ggtactccac   2280

tgctggctat ccagcgcctg gagatcgttc gcaccaccgg ctcgatcatc atcaccatct   2340

atgacgctca tacccttcag gtagagatgc cggaatccgg caatgcccca tcgctggtgg   2400

ctattggtcg tcgaagtgag tccgactgct tgtctgagga gcttcgccac atggatccag   2460

atttgggcta ccagcacgca ctatccggct tgtccagcgt caagctggaa accgtctaa    2519
```

<210> SEQ ID NO 3
<211> LENGTH: 833
<212> TYPE: PRT
<213> ORGANISM: Corynebacterium glutamicum

<400> SEQUENCE: 3

```
Met Ser Thr Asn Thr Thr Pro Ser Ser Trp Thr Asn Pro Leu Arg Asp
1               5                   10                  15

Pro Gln Asp Lys Arg Leu Pro Arg Ile Ala Gly Pro Ser Gly Met Val
            20                  25                  30

Ile Phe Gly Val Thr Gly Asp Leu Ala Arg Lys Lys Leu Leu Pro Ala
        35                  40                  45

Ile Tyr Asp Leu Ala Asn Arg Gly Leu Leu Pro Pro Gly Phe Ser Leu
    50                  55                  60

Val Gly Tyr Gly Arg Arg Glu Trp Ser Lys Glu Asp Phe Glu Lys Tyr
65                  70                  75                  80

Val Arg Asp Ala Ala Ser Ala Gly Ala Arg Thr Glu Phe Arg Glu Asn
                85                  90                  95

Val Trp Glu Arg Leu Ala Glu Gly Met Glu Phe Val Arg Gly Asn Phe
            100                 105                 110

Asp Asp Asp Ala Ala Phe Asp Asn Leu Ala Ala Thr Leu Lys Arg Ile
        115                 120                 125
```

```
Asp Lys Thr Arg Gly Thr Ala Gly Asn Trp Ala Tyr Tyr Leu Ser Ile
    130                 135                 140

Pro Pro Asp Ser Phe Thr Ala Val Cys His Gln Leu Glu Arg Ser Gly
145                 150                 155                 160

Met Ala Glu Ser Thr Glu Glu Ala Trp Arg Arg Val Ile Ile Glu Lys
                165                 170                 175

Pro Phe Gly His Asn Leu Glu Ser Ala His Glu Leu Asn Gln Leu Val
            180                 185                 190

Asn Ala Val Phe Pro Glu Ser Ser Val Phe Arg Ile Asp His Tyr Leu
        195                 200                 205

Gly Lys Glu Thr Val Gln Asn Ile Leu Ala Leu Arg Phe Ala Asn Gln
    210                 215                 220

Leu Phe Glu Pro Leu Trp Asn Ser Asn Tyr Val Asp His Val Gln Ile
225                 230                 235                 240

Thr Met Ala Glu Asp Ile Gly Leu Gly Gly Arg Ala Gly Tyr Tyr Asp
                245                 250                 255

Gly Ile Gly Ala Ala Arg Asp Val Ile Gln Asn His Leu Ile Gln Leu
            260                 265                 270

Leu Ala Leu Val Ala Met Glu Glu Pro Ile Ser Phe Val Pro Ala Gln
        275                 280                 285

Leu Gln Ala Glu Lys Ile Lys Val Leu Ser Ala Thr Lys Pro Cys Tyr
    290                 295                 300

Pro Leu Asp Lys Thr Ser Ala Arg Gly Gln Tyr Ala Ala Gly Trp Gln
305                 310                 315                 320

Gly Ser Glu Leu Val Lys Gly Leu Arg Glu Glu Asp Gly Phe Asn Pro
                325                 330                 335

Glu Ser Thr Thr Glu Thr Phe Ala Ala Cys Thr Leu Glu Ile Thr Ser
            340                 345                 350

Arg Arg Trp Ala Gly Val Pro Phe Tyr Leu Arg Thr Gly Lys Arg Leu
        355                 360                 365

Gly Arg Arg Val Thr Glu Ile Ala Val Val Phe Lys Asp Ala Pro His
    370                 375                 380

Gln Pro Phe Asp Gly Asp Met Thr Val Ser Leu Gly Gln Asn Ala Ile
385                 390                 395                 400

Val Ile Arg Val Gln Pro Asp Glu Gly Val Leu Ile Arg Phe Gly Ser
                405                 410                 415

Lys Val Pro Gly Ser Ala Met Glu Val Arg Asp Val Asn Met Asp Phe
            420                 425                 430

Ser Tyr Ser Glu Ser Phe Thr Glu Glu Ser Pro Glu Ala Tyr Glu Arg
        435                 440                 445

Leu Ile Leu Asp Ala Leu Leu Asp Glu Ser Ser Leu Phe Pro Thr Asn
    450                 455                 460

Glu Glu Val Glu Leu Ser Trp Lys Ile Leu Asp Pro Ile Leu Glu Ala
465                 470                 475                 480

Trp Asp Ala Asp Gly Glu Pro Glu Asp Tyr Pro Ala Gly Thr Trp Gly
                485                 490                 495

Pro Lys Ser Ala Asp Glu Met Leu Ser Arg Asn Gly His Thr Trp Arg
            500                 505                 510

Arg Pro Met Ile Phe Glu Leu Pro Asp Thr Thr Thr Gln Gln Ile Ser
        515                 520                 525

Lys Thr Leu Thr Arg Leu Arg Glu Ser Gly Thr Gln Val Thr Thr Gly
    530                 535                 540
```

```
Arg Val Leu Thr Leu Ile Val Val Thr Asp Ser Glu Ser Asp Val Ala
545                 550                 555                 560

Ala Val Thr Glu Ser Thr Asn Glu Ala Ser Arg Glu His Pro Ser Arg
                565                 570                 575

Val Ile Ile Leu Val Val Gly Asp Lys Thr Ala Glu Asn Lys Val Asp
            580                 585                 590

Ala Glu Val Arg Ile Gly Gly Asp Ala Gly Ala Ser Glu Met Ile Ile
        595                 600                 605

Met His Leu Asn Gly Pro Val Ala Asp Lys Leu Gln Tyr Val Val Thr
    610                 615                 620

Pro Leu Leu Leu Pro Asp Thr Pro Ile Val Ala Trp Trp Pro Gly Glu
625                 630                 635                 640

Ser Pro Lys Asn Pro Ser Gln Asp Pro Ile Gly Arg Ile Ala Gln Arg
                645                 650                 655

Arg Ile Thr Asp Ala Leu Tyr Asp Arg Asp Asp Ala Leu Glu Asp Arg
            660                 665                 670

Val Glu Asn Tyr His Pro Gly Asp Thr Asp Met Thr Trp Ala Arg Leu
        675                 680                 685

Thr Gln Trp Arg Gly Leu Val Ala Ser Ser Leu Asp His Pro Pro His
    690                 695                 700

Ser Glu Ile Thr Ser Val Arg Leu Thr Gly Ala Ser Gly Ser Thr Ser
705                 710                 715                 720

Val Asp Leu Ala Ala Gly Trp Leu Ala Arg Arg Leu Lys Val Pro Val
                725                 730                 735

Ile Arg Glu Val Thr Asp Ala Pro Thr Val Pro Thr Asp Glu Phe Gly
            740                 745                 750

Thr Pro Leu Leu Ala Ile Gln Arg Leu Glu Ile Val Arg Thr Thr Gly
        755                 760                 765

Ser Ile Ile Ile Thr Ile Tyr Asp Ala His Thr Leu Gln Val Glu Met
    770                 775                 780

Pro Glu Ser Gly Asn Ala Pro Ser Leu Val Ala Ile Gly Arg Arg Ser
785                 790                 795                 800

Glu Ser Asp Cys Leu Ser Glu Glu Leu Arg His Met Asp Pro Asp Leu
                805                 810                 815

Gly Tyr Gln His Ala Leu Ser Gly Leu Ser Ser Val Lys Leu Glu Thr
            820                 825                 830

Val
```

<210> SEQ ID NO 4
<211> LENGTH: 1852
<212> TYPE: DNA
<213> ORGANISM: Artificial Sequence
<220> FEATURE:
<223> OTHER INFORMATION: Synthesized

<400> SEQUENCE: 4

```
aaaggaggat cctcatgact gctcactgga aacaaaacca aaagaacctc atgctgtttt      60

cgggtcgtgc gcacccagaa ctggcagaag ctgtagctaa agagctcgac gtcaacgtca     120

ccccaatgac ggcacgcgat ttcgccaacg gtgaaatcta cgtccgcttc gaggaatcag     180

ttcgtggctc cgactgcttc gtcctgcagt cccacaccca gcctctcaac aagtggctca     240

tggaacagct gctgatgatc gacgctttga agcgtggttc cgcaaagcgc atcaccgcga     300

tcctgccgtt ctacccatat gcccgccagg acaagaagca ccgcggccgc gagccaattt     360

ctgctcgcct catcgccgac ctcatgctca ccgctggcgc ggaccgtatc gtgtccgtgg     420
```

```
acttgcacac cgatcagatc cagggcttct tcgacggccc agtcgatcac atgcacgcca    480
tgccgatcct caccgatcac atcaaggaaa actacaacct ggacaacatc tgcgtggtct    540
cccctgacgc aggtcgcgtg aaggttgcag agaagtgggc taacaccttg ggcgatgccc    600
caatggcgtt cgtgcacaag acccgctcca ccgaggtagc aaaccaggtt gtcgccaacc    660
gcgtcgtcgg tgacgtcgac ggcaaggact gcgtgcttct cgacgacatg atcgacactg    720
gcggcaccat cgccggcgct gtgggcgtcc tgaagaaggc tggcgcaaag tcagtcgtca    780
tcgcctgcac ccacggtgtg ttctctgacc cagcccgcga gcgcctgtct gcatgcggtg    840
ctgaagaagt catcaccacc gacaccctgc cacagtccac cgagggctgg agcaacctga    900
ccgttttgtc gatcgcaccg ctgctggctc gcaccatcaa cgagatcttc gaaaacggtt    960
ccgtcaccac cctcttcgag ggcgaggcct aaaaaggagg acaatcatgt tgaaaatcgc   1020
tgtcccaaac aaaggctcgc tgtccgagcg cgccatggaa atcctcgccg aagcaggcta   1080
cgcaggccgt ggagattcca aatccctcaa cgtttttgat gaagcaaaca acgttgaatt   1140
cttcttcctt cgccctaaag atatcgccat ctacgttgct ggtggccagc tcgatttggg   1200
tatcaccggc cgcgaccttg ctcgcgattc ccaggctgat gtccacgaag ttctttccct   1260
cggcttcggt tcctccactt tccgttacgc agcaccagct gatgaagagt ggagcatcga   1320
aaagctcgac ggcaagcgca tcgctacctc ttaccccaac cttgttcgcg atgacctcgc   1380
agcacgtggg ctttccgctg aggtgctccg cctcgacggt gcagtagagg tatccatcaa   1440
gcttggtgtc gcagatgcca tcgccgatgt tgtatccacc ggccgcacgc tgcgtcagca   1500
aggtcttgca cctttcggcg aggttctgtg cacctctgag gctgtcattg ttggccgcaa   1560
ggatgaaaag gtcaccccag agcagcagat cctgcttcgc cgcatccagg gaattttgca   1620
cgcgcagaac ttcctcatgc tggattacaa ggtcgaccgc gacaacctgg acgctgccac   1680
tgcagtaacc ccaggcttct ccggcccagc ggtatcccca ctggcacgcg acaactgggt   1740
tgctgtacgc gccatggtgc cacgcaggtc agctaacgcc atcatggata agcttgctgg   1800
actcggcgct gaagccatcc tggcttctga aatccgcatc gcccgcatct ag           1852
```

<210> SEQ ID NO 5
<211> LENGTH: 325
<212> TYPE: PRT
<213> ORGANISM: Corynebacterium glutamicum

<400> SEQUENCE: 5

```
Met Thr Ala His Trp Lys Gln Asn Gln Lys Asn Leu Met Leu Phe Ser
1               5                   10                  15

Gly Arg Ala His Pro Glu Leu Ala Glu Ala Val Ala Lys Glu Leu Asp
            20                  25                  30

Val Asn Val Thr Pro Met Thr Ala Arg Asp Phe Ala Asn Gly Glu Ile
        35                  40                  45

Tyr Val Arg Phe Glu Glu Ser Val Arg Gly Ser Asp Cys Phe Val Leu
    50                  55                  60

Gln Ser His Thr Gln Pro Leu Asn Lys Trp Leu Met Glu Gln Leu Leu
65                  70                  75                  80

Met Ile Asp Ala Leu Lys Arg Gly Ser Ala Lys Arg Ile Thr Ala Ile
                85                  90                  95

Leu Pro Phe Tyr Pro Tyr Ala Arg Gln Asp Lys Lys His Arg Gly Arg
            100                 105                 110

Glu Pro Ile Ser Ala Arg Leu Ile Ala Asp Leu Met Leu Thr Ala Gly
```

```
        115                 120                 125

Ala Asp Arg Ile Val Ser Val Asp Leu His Thr Asp Gln Ile Gln Gly
    130                 135                 140

Phe Phe Asp Gly Pro Val Asp His Met His Ala Met Pro Ile Leu Thr
145                 150                 155                 160

Asp His Ile Lys Glu Asn Tyr Asn Leu Asp Asn Ile Cys Val Val Ser
                165                 170                 175

Pro Asp Ala Gly Arg Val Lys Val Ala Glu Lys Trp Ala Asn Thr Leu
            180                 185                 190

Gly Asp Ala Pro Met Ala Phe Val His Lys Thr Arg Ser Thr Glu Val
        195                 200                 205

Ala Asn Gln Val Val Ala Asn Arg Val Val Gly Asp Val Asp Gly Lys
    210                 215                 220

Asp Cys Val Leu Leu Asp Asp Met Ile Asp Thr Gly Gly Thr Ile Ala
225                 230                 235                 240

Gly Ala Val Gly Val Leu Lys Lys Ala Gly Ala Lys Ser Val Val Ile
                245                 250                 255

Ala Cys Thr His Gly Val Phe Ser Asp Pro Ala Arg Glu Arg Leu Ser
            260                 265                 270

Ala Cys Gly Ala Glu Glu Val Ile Thr Thr Asp Thr Leu Pro Gln Ser
        275                 280                 285

Thr Glu Gly Trp Ser Asn Leu Thr Val Leu Ser Ile Ala Pro Leu Leu
    290                 295                 300

Ala Arg Thr Ile Asn Glu Ile Phe Glu Asn Gly Ser Val Thr Thr Leu
305                 310                 315                 320

Phe Glu Gly Glu Ala
                325


<210> SEQ ID NO 6
<211> LENGTH: 281
<212> TYPE: PRT
<213> ORGANISM: Corynebacterium glutamicum

<400> SEQUENCE: 6

Met Leu Lys Ile Ala Val Pro Asn Lys Gly Ser Leu Ser Glu Arg Ala
1               5                   10                  15

Met Glu Ile Leu Ala Glu Ala Gly Tyr Ala Gly Arg Gly Asp Ser Lys
            20                  25                  30

Ser Leu Asn Val Phe Asp Glu Ala Asn Asn Val Glu Phe Phe Phe Leu
        35                  40                  45

Arg Pro Lys Asp Ile Ala Ile Tyr Val Ala Gly Gly Gln Leu Asp Leu
    50                  55                  60

Gly Ile Thr Gly Arg Asp Leu Ala Arg Asp Ser Gln Ala Asp Val His
65                  70                  75                  80

Glu Val Leu Ser Leu Gly Phe Gly Ser Ser Thr Phe Arg Tyr Ala Ala
                85                  90                  95

Pro Ala Asp Glu Glu Trp Ser Ile Glu Lys Leu Asp Gly Lys Arg Ile
            100                 105                 110

Ala Thr Ser Tyr Pro Asn Leu Val Arg Asp Asp Leu Ala Ala Arg Gly
        115                 120                 125

Leu Ser Ala Glu Val Leu Arg Leu Asp Gly Ala Val Glu Val Ser Ile
    130                 135                 140

Lys Leu Gly Val Ala Asp Ala Ile Ala Asp Val Val Ser Thr Gly Arg
145                 150                 155                 160
```

```
Thr Leu Arg Gln Gln Gly Leu Ala Pro Phe Gly Glu Val Leu Cys Thr
                165                 170                 175

Ser Glu Ala Val Ile Val Gly Arg Lys Asp Glu Lys Val Thr Pro Glu
            180                 185                 190

Gln Gln Ile Leu Leu Arg Arg Ile Gln Gly Ile Leu His Ala Gln Asn
        195                 200                 205

Phe Leu Met Leu Asp Tyr Asn Val Asp Arg Asp Asn Leu Asp Ala Ala
    210                 215                 220

Thr Ala Val Thr Pro Gly Leu Ser Gly Pro Thr Val Ser Pro Leu Ala
225                 230                 235                 240

Arg Asp Asn Trp Val Ala Val Arg Ala Met Val Pro Arg Arg Ser Ala
                245                 250                 255

Asn Ala Ile Met Asp Lys Leu Ala Gly Leu Gly Ala Glu Ala Ile Leu
            260                 265                 270

Ala Ser Glu Ile Arg Ile Ala Arg Ile
        275                 280


<210> SEQ ID NO 7
<211> LENGTH: 1920
<212> TYPE: DNA
<213> ORGANISM: Artificial Sequence
<220> FEATURE:
<223> OTHER INFORMATION: Synthesized

<400> SEQUENCE: 7

gtatcggcgt ggagttgtcc gaggaactcc agctgcaccc agagcagtcc acagacgcgt     60

ttgtgctcta ccacccagag gcaaagtact ttaacgtcta acacctttga gagggaaaac    120

tttcccgcac attgcagatc gtgccacttt aactaaggtt gacggcatga ttaaggcgat    180

tttctgggac atggacggca cgatggtgga ctctgagcca cagtggggca ttgctaccta    240

cgagctcagc gaagccatgg gccgccgcct cacccccggag ctccgggaac tcaccgtcgg    300

ctcgagcctg ccgcgcacca tgcgcttatg cgcagagcac gcaggcatta cattgagcga    360

cgcggactac gagcgctacc gggctggcat gttcgcccgg gtccatgagc ttttcgacga    420

atccctcgtc ccaaatccag gcgtcaccga actcctgaca gagttgaagg ccctcgagat    480

ccccatgttg gtcaccacca acacagagcg cgatctcgcg acccgttcag tcgcagccgt    540

gggaaatgag ttcttcatcg gttctatcgc tggtgatgaa gtcccaacag caaagccagc    600

cccgacatg tacctcgaag cagcacgacg tgtgggcttt gacccatcag agtgcctcgt    660

gttcgaagat tcctacaacg gcatgctggg cgctgttact gcaggttgcc gcgtcattgg    720

tctgcaccca gaagaagtcc aagcgccaga aggtgtagtg cctttgcgtt ccctccacgg    780

taaaaactct ttcgaaggtg tcaccgctga gatggtcact gcctggtacc accagatcga    840

gccggcaggt gtcgcaaaat aaagctactc cactagtgtg atcggggtta ttttttcact    900

tcaatgggtg gctaaaagac gtgggcacgt gagtaaactc atgcgcgcga aacgatggga    960

gtgaacccat acttttatat atgggtatcg gcggtctatg cttgtgggcg tacctgtccc   1020

gcgagtgagg tcttacgcaa aggaggaacc gaatgaagac atttgactcg ctgtacgaag   1080

aacttcttaa ccgtgctcag acccgccctg aagggtctgg aaccgtggcc gccttggata   1140

aaggcatcca tcatctaggt aagaaggtca tcgaagaagc cggagaggtc tggattgcag   1200

ccgagtatga gaccgatgaa gagctagccg gagaaatctc ccagctcatt tattggaccc   1260

aggtcatcat ggttgctcgc ggcctgaagc cagaagatat ctacaagaac ctgtaggagt   1320

tttaaagcaa tcatgttgaa aatcgctgtc ccaaacaaag gctcgctgtc cgagcgcgcc   1380
```

```
atggaaatcc tcgccgaagc aggctacgca ggccgtggag attccaaatc cctcaacgtt   1440

tttgatgaag caaacaacgt tgaattcttc ttccttcgcc ctaaagatat cgccatctac   1500

gttgctggtg gccagctcga tttgggtatc accggccgcg accttgctcg cgattcccag   1560

gctgatgtcc acgaagttct ttccctcggc ttcggttcct ccactttccg ttacgcagca   1620

ccagctgatg aagagtggag catcgaaaag ctcgacggca agcgcatcgc tacctcttac   1680

cccaaccttg ttcgcgatga cctcgcagca cgtgggcttt ccgctgaggt gctccgcctc   1740

gacggtgcag tagaggtatc catcaagctt ggtgtcgcag atgccatcgc cgatgttgta   1800

tccaccggcc gcacgctgcg tcagcaaggt cttgcacctt tcggcgaggt tctgtgcacc   1860

tctgaggctg tcattgttgg ccgcaaggat gaaaaggtca ccccagagca gcagatcctg   1920
```

<210> SEQ ID NO 8
<211> LENGTH: 1694
<212> TYPE: DNA
<213> ORGANISM: Artificial Sequence
<220> FEATURE:
<223> OTHER INFORMATION: Synthesized

<400> SEQUENCE: 8

```
cgaggaaacc gttgaggagt tcgtccatgt cgacttcttc aggttcgaag tagtcatcgt     60

ctgtttccca ttcgatttct gagtcatcgt ctaggtagtc gtcttctgca tcctcgtctg    120

ccatgtctga ttcttcccac tctgcgtctt ctagggattc gatgagctct tcaactggag    180

tgggaacgta cagcccccgg attttctcta cgagatctgc ttggtcttgt tcgtcgctga    240

gttcatcggc attgttcgtg tcgtcagggc ttccggtgtc gctgaagtta agttctgaaa    300

aacgctccag aatataggtc acagccatgg cggtggtgtc caaggacagg ttgatgaatt    360

ggcgtagctg ttgggtgctt aacccttcat cgatgcagat ggtcgtgcgg aatttcaatt    420

ccacttcgcc gtcgttgccc agatggacga gggctgttgg cccgatgcgt tcggcattcc    480

attcggtgac agctcgcgcc gcatcgttga tggcaaacat gtccaaatta aggcgcgtgc    540

gaccaaggat ggtgagcatt tgccctgatt cgtggctgaa gtacatcgaa atgcggtgat    600

cttgccacgg cacgatgatg cgatcttctg agctcaaata gtggtagccc aaggaatcaa    660

cagcctccgt cactcgattc aggtcaactg ggaaaggaat ggaggtgttg ggtgcaggga    720

cgtttcgatc attcacagag gtgaaatcca tagctactcc actagtgtga tcggggttat    780

tttttcactt caatgggtgg ctaaaagacg tgggcacgtg agtaaactca tgcgcgcgaa    840

acgatgggag tgaacccata cttttatata tgggtatcgg cggtctatgc ttgtgggcgt    900

acctgtcccg cgagtgaggt cttacgcaaa ggaggatcgc catgttgaat gtcactgacc    960

tgcgaggtca aacaccatcc aagagcgaca tccgacgtgc tttgccacgt ggtggcactg   1020

acgtgtggtc tgtgcttccc atagtgcagc ctgttgtaga agatgtccaa aaccgcggcg   1080

ctgaagctgc tttggattac ggcgagaagt tcgaccatat tcgcccgcc tcggtgcggg   1140

tgccagctga ggttattgct gcagcagaaa acaccttaga tccgttggtg cgtgaatcga   1200

ttgaagagtc gattcgtcgc gtccgcaagg ttcacgctga gcaaaagcca tccgagcaca   1260

ccactgaact ttcaccaggt ggcaccgtca ctgagcgttt catgccgatt gatcgcgtgg   1320

gactgtacgt tccaggcggc aatgcggtgt acccatcaag cgtgattatg aatactgtcc   1380

cagctcaaga ggctggtgtg aactcccttg tggttgcgtc gcctcctcag gctgagcacg   1440

gtggctggcc tcaccccacc attttggcgg cgtgttccat cttgggtgtt gatgaggtgt   1500
```

gggctgtcgg cggcggtcag gccgtggcgt tgctggctta tggtgatgac gctgcaggtc 1560
tcgagcctgt ggatatgatc actggacctg gcaatatctt tgtcaccgct gcgaagcgcc 1620
tggtcagggg agtggtaggt actgattctg aggctggccc tacagaaatc gctgtgcttg 1680
ctgatgcctc tgcc 1694

<210> SEQ ID NO 9
<211> LENGTH: 1689
<212> TYPE: DNA
<213> ORGANISM: Artificial Sequence
<220> FEATURE:
<223> OTHER INFORMATION: Synthesized

<400> SEQUENCE: 9
atctacgttg ctggtggcca gctcgatttg ggtatcaccg gccgcgacct tgctcgcgat 60
tcccaggctg atgtccacga agttctttcc ctcggcttcg gttcctccac tttccgttac 120
gcagcaccag ctgatgaaga gtggagcatc gaaaagctcg acggcaagcg catcgctacc 180
tcttacccca accttgttcg cgatgacctc gcagcacgtg ggctttccgc tgaggtgctc 240
cgcctcgacg gtgcagtaga ggtatccatc aagcttggtg tcgcagatgc catcgccgat 300
gttgtatcca ccggccgcac gctgcgtcag caaggtcttg cacctttcgg cgaggttctg 360
tgcacctctg aggctgtcat tgttggccgc aaggatgaaa aggtcacccc agagcagcag 420
ctgttgcccg tctcactggt gaaaagaaaa accaccctgg cgccggggat cagccccgga 480
tgctttggat acggtctatg agctggcagc gtatttgacc gatccggaca cctgggataa 540
tgtgtggatt ttgtcggatc agcttgagta ggacaaatcc gccgagcttc gacgagattt 600
tcaggagcta aggaagctaa aatggagaaa aaaatcactg gatataccac cgttgatata 660
tcccaatggc atcgtaaaga acattttgag gcatttcagt cagttgctca atgtacctat 720
aaccagaccg ttcagctgga tattacggcc tttttaaaga ccgtaaagaa aaataagcac 780
aagttttatc cggcctttat tcacattctt gcccgcctga tgaatgctca tccggagttc 840
cgtatggcaa tgaaagacgg tgagctggtg atatgggata gtgttcaccc ttgttacacc 900
gttttccatg agcaaactga aacgttttca tcgctctgga gtgaatacca cgacgatttc 960
cggcagtttc tacacatata ttcgcaagat gtggcgtgtt acggtgaaaa cctggcctat 1020
ttccctaaag ggtttattga gaatatgttt ttcgtctcag ccaatccctg ggtgagtttc 1080
accagttttg atttaaacgt ggccaatatg gacaacttct tcgcccccgt tttcaccatg 1140
ggcaaatatt atacgcaagg cgacaaggtg ctgatgccgc tggcgattca ggttcatcat 1200
gccgtctgtg atggcttcca tgtcggcaga atgcttaatg aattacaaca gtactgcgat 1260
gagtggcagg gcggggcgta atttttaacta cccccgaaaa tgtagtgggt agttccacac 1320
tgcctcttac aagtacgtag gataatccac agcaccattg tgatttcctt caacttgtga 1380
gaggcagtac atgtctaaga cgagcaacaa gtcttcagca gactcaaaga atgacgcaaa 1440
agccgaagac attgtgaacg gcgagaacca aatcgccacg aatgagtcgc agtcttcaga 1500
cagcgctgca gtttcggaac gtgtcgtcga accaaaaacc acggttcaga aaaagttccg 1560
aatcgaatcg gatctgcttg gtgaacttca gatcccatcc cacgcatatt acggggtgca 1620
cacccttcgt gcggtggaca acttccaaat ctcacgaacc accatcaacc acgtcccaga 1680
tttcattcg 1689

<210> SEQ ID NO 10
<211> LENGTH: 1092

<212> TYPE: DNA
<213> ORGANISM: Artificial Sequence
<220> FEATURE:
<223> OTHER INFORMATION: Synthesized

<400> SEQUENCE: 10

```
atctacgttg ctggtggcca gctcgatttg ggtatcaccg gccgcgacct tgctcgcgat     60

tcccaggctg atgtccacga agttctttcc ctcggcttcg gttcctccac tttccgttac    120

gcagcaccag ctgatgaaga gtggagcatc gaaaagctcg acggcaagcg catcgctacc    180

tcttacccca accttgttcg cgatgacctc gcagcacgtg ggctttccgc tgaggtgctc    240

cgcctcgacg gtgcagtaga ggtatccatc aagcttggtg tcgcagatgc catcgccgat    300

gttgtatcca ccggccgcac gctgcgtcag caaggtcttg cacctttcgg cgaggttctg    360

tgcacctctg aggctgtcat tgttggccgc aaggatgaaa aggtcacccc agagcagcag    420

atcctgcttc gccgcatcca gggaattttg cacgcgcaga acttcctcat gctggattac    480

aaggtcgacc gcgacaacct ggacgctgcc actgcagtaa ccccaggctt ctccggccca    540

gcggtatccc cactggcacg cgacaactgg gttgctgtac gcgccatggt gccacgcagg    600

tcagctaacg ccatcatgga taagcttgct ggactcggcg ctgaagccat cctggcttct    660

gaaatccgca tcgcccgcat ctagttttaa ctacccccga aaatgtagtg ggtagttcca    720

cactgcctct tacaagtacg taggataatc cacagcacca ttgtgatttc cttcaacttg    780

tgagaggcag tacatgtcta agacgagcaa caagtcttca gcagactcaa agaatgacgc    840

aaaagccgaa gacattgtga acggcgagaa ccaaatcgcc acgaatgagt cgcagtcttc    900

agacagcgct gcagtttcgg aacgtgtcgt cgaaccaaaa accacggttc agaaaaagtt    960

ccgaatcgaa tcggatctgc ttggtgaact tcagatccca tcccacgcat attacggggt   1020

gcacaccctt cgtgcggtgg acaacttcca aatctcacga accaccatca accacgtccc   1080

agatttcatt cg                                                        1092
```

<210> SEQ ID NO 11
<211> LENGTH: 1455
<212> TYPE: DNA
<213> ORGANISM: Artificial Sequence
<220> FEATURE:
<223> OTHER INFORMATION: Synthesized

<400> SEQUENCE: 11

```
tccagcaacc acctggatcg atgtggaggt ttctatcggc cgcgacgtga tcatccaccc     60

tggcacccag ctcaagggcg aaactgtcat cggagaccgc gttgaagttg gtccagacac    120

caccttgacc aacatgacca tcggcgacgg cgcatccgta atccgcaccc acggtttcga    180

ctccaccatc ggtgaaaacg ccaccgttgg ccccttcacc tacatccgcc caggaaccac    240

actgggacca gaaggcaagc tcggtggctt cgtagaaacc aagaaggcca caatcggccg    300

tggctccaag gttccacacc tcacctatgt cggcgacgcc accatcggcg aggaatccaa    360

catcggagcc tcctctgtct tcgtgaacta cgacggtgaa aacaagcacc acaccaccat    420

cggcagccac gttcgcactg gttctgacac catgtttatc gctccagtga ccgtgggtga    480

cggagcgtat tccggagccg gtacagtaat taaagacgat gttccgccag gagcccttgc    540

cgtgtccggc ggacgccaac gaaacatcga aggctgggtg caaaagaagc gccctggaac    600

cgctgcagca caagccgcag aagccgccca aaacgtccac aaccaggaag gctaatagct    660

gccaattatt ccgggcttgt gacccgctac ccgataaata ggtcggctga aaaatttcgt    720
```

tgcaatatca acaaaaaggc ctatcattgg gaggtgtcgc accaagtact tttgcgaagc 780
gccatctgac ggattttcaa aagatgtata tgctcggtgc ggaaacctac gaaaggattt 840
tttacccaaa ggaggacaac catgactgct cactggaaac aaaaccaaaa gaacctcatg 900
ctgttttcgg gtcgtgcgca cccagaactg gcagaagctg tagctaaaga gctcgacgtc 960
aacgtcaccc caatgacggc acgcgatttc gccaacggtg aaatctacgt ccgcttcgag 1020
gaatcagttc gtggctccga ctgcttcgtc ctgcagtccc acacccagcc tctcaacaag 1080
tggctcatgg aacagctgct gatgatcgac gctttgaagc gtggttccgc aaagcgcatc 1140
accgcgatcc tgccgttcta cccatatgcc cgccaggaca agaagcaccg cggccgcgag 1200
ccaatttctg ctcgcctcat cgccgacctc atgctcaccg ctggcgcgga ccgtatcgtg 1260
tccgtggact tgcacaccga tcagatccag ggcttcttcg acggcccagt cgatcacatg 1320
cacgccatgc cgatcctcac cgatcacatc aaggaaaact acaacctgga caacatctgc 1380
gtggtctccc ctgacgcagg tcgcgtgaag gttgcagaga agtgggctaa caccttgggc 1440
gatgccccaa tggcg 1455

<210> SEQ ID NO 12
<211> LENGTH: 1512
<212> TYPE: DNA
<213> ORGANISM: Artificial Sequence
<220> FEATURE:
<223> OTHER INFORMATION: Synthesized

<400> SEQUENCE: 12
tcaacgatca ctgcccagcc gacgagcact ggcatacaac ctgcggctcc gccccacacg 60
atattcatgt gcgtgcggcg cttcagccac ttggtgtaga caaaaatgta gaagaaaatc 120
gtgatcaaca cgaagatgcc ggcgagcatc gaatcgcaca gcagccacag ccacaagaag 180
ctggccactg tcaggaccca cgcaaaaatg gaggcgtcgc gattactcac ggtgtggcgc 240
accaaagggc gagccctagt gcgtcccatg cgctgatcaa tatcggagtc tgccaccatg 300
ttgaaggtgt tggcggcggc cgcacccatc cagccaccga acacagtcag caagatgagc 360
acaatgttgt tctcaccgcg ttcagcctga agcattgtgg ggattgtggc gacaaggagg 420
agttcaataa ccctgggctt cgttagcgca atataggcct tgatcgtgtc caagggttct 480
cctccagaac gttgcatttt caaatcactc atatatttaa gttgtgagtc cttattattt 540
aaatatccct gcggtgagtg tgcaccttgc gttgaaggcc cagactctga cagaagcgtc 600
agagtgttta ctcaagacat tttctaagac acactggccg ttaccctgcg aatgtccaca 660
gggtagctgg tagtttgaaa atcaacgccg ttgcccttag gattcagtaa ctggcacatt 720
ttgtaatgcg ctagatctgt gtgctcagtc ttccaggctg cttatcacag tgaaagcaaa 780
accaattcgt ggctgcgaaa gtcgtagcca ccacgaagtc caggaggaca tacaaaagga 840
ggacaacctt gaccaccttg acgctgtcac ctgaacttca ggcgctcact gtacgcaatt 900
acccctctga ttggtccgat gtggacacca aggctgtaga cactgttcgt gtcctcgctg 960
cagacgctgt agaaaactgt ggctccggcc acccaggcac cgcaatgagc ctggctcccc 1020
ttgcatacac cttgtaccag cgggttatga acgtagatcc acaggacacc aactgggcag 1080
gccgtgaccg cttcgttctt tcttgtggcc actcctcttt gacccagtac atccagcttt 1140
acttgggtgg attcggcctt gagatggatg acctgaaggc tctgcgcacc tgggattcct 1200
tgaccccagg acaccctgag taccgccaca ccaagggcgt tgagatcacc actggccctc 1260
ttggccaggg tcttgcatct gcagttggta tggccatggc tgctcgtcgt gagcgtggcc 1320

```
tattcgaccc aaccgctgct gagggcgaat ccccattcga ccaccacatc tacgtcattg   1380

cttctgatgg tgacctgcag gaaggtgtca cctctgaggc atcctccatc gctggcaccc   1440

agcagctggg caacctcatc gtgttctggg atgacaaccg catctccatc gaagacaaca   1500

ctgagatcgc tt                                                        1512
```

```
<210> SEQ ID NO 13
<211> LENGTH: 1623
<212> TYPE: DNA
<213> ORGANISM: Corynebacterium glutamicum

<400> SEQUENCE: 13

atggcggaca tttcgaccac ccaggtttgg caagacctga ccgatcatta ctcaaacttc     60

caggcaacca ctctgcgtga acttttcaag gaagaaaacc gcgccgagaa gtacaccttc    120

tccgcggctg gcctccacgt cgacctgtcg aagaatctgc ttgacgacgc caccctcacc    180

aagctccttg cactgaccga agaatctggc cttcgcgaac gcattgacgc gatgtttgcc    240

ggtgaacacc tcaacaacac cgaagaccgc gctgtcctcc acaccgcgct gcgccttcct    300

gccgaagctg atctgtcagt agatggccaa gatgttgctg ctgatgtcca cgaagttttg    360

ggacgcatgc gtgacttcgc tactgcgctg cgctcaggca actggttggg acacaccggc    420

cacacgatca agaagatcgt caacattggt atcggtggct ctgacctcgg accagccatg    480

gctacgaagg ctctgcgtgc atacgcgacc gctggtatct cagcagaatt cgtctccaac    540

gtcgacccag cagacctcgt ttctgtgttg gaagacctcg atgcagaatc cacattgttc    600

gtgatcgctt cgaaaacttt caccacccag gagacgctgt ccaacgctcg tgcagctcgt    660

gcttggctgg tagagaagct cggtgaagag gctgtcgcga agcacttcgt cgcagtgtcc    720

accaatgctg aaaaggtcgc agagttcggt atcgacacgg acaacatgtt cggcttctgg    780

gactgggtcg gaggtcgtta ctccgtggac tccgcagttg gtctttccct catggcagtg    840

atcggccctc gcgacttcat gcgtttcctc ggtggattcc acgcgatgga tgaacacttc    900

cgcaccacca agttcgaaga gaacgttcca atcttgatgg ctctgctcgg tgtctggtac    960

tccgatttct atggtgcaga aacccacgct gtcctacctt attccgagga tctcagccgt   1020

tttgctgctt acctccagca gctgaccatg gaatcaaatg gcaagtcagt ccaccgcgac   1080

ggctcccctg tttccactgg cactggcgaa atttactggg gtgagcctgg cacaaatggc   1140

cagcacgctt tcttccagct gatccaccag ggcactcgcc ttgttccagc tgatttcatt   1200

ggtttcgctc gtccaaagca ggatcttcct gccggtgagc gcaccatgca tgaccttttg   1260

atgagcaact tcttcgcaca gaccaaggtt ttggctttcg gtaagaacgc tgaagagatc   1320

gctgcggaag gtgtcgcacc tgagctggtc aaccacaagg tcatgccagg taatcgccca   1380

accaccacca ttttggcgga ggaacttacc ccttctattc tcggtgcgtt gatcgctttg   1440

tacgaacaca tcgtgatggt tcagggcgtg atttgggaca tcaactcctt cgaccaatgg   1500

ggtgttgaac tgggcaaaca gcaggcaaat gacctcgctc cggctgtctc tggtgaagag   1560

gatgttgact cgggagattc ttccactgat tcactgatta agtggtaccg cgcaaatagg   1620

tag                                                                 1623
```

```
<210> SEQ ID NO 14
<211> LENGTH: 540
<212> TYPE: PRT
<213> ORGANISM: Corynebacterium glutamicum
```

<400> SEQUENCE: 14

```
Met Ala Asp Ile Ser Thr Thr Gln Val Trp Gln Asp Leu Thr Asp His
1               5                   10                  15

Tyr Ser Asn Phe Gln Ala Thr Thr Leu Arg Glu Leu Phe Lys Glu Glu
            20                  25                  30

Asn Arg Ala Glu Lys Tyr Thr Phe Ser Ala Ala Gly Leu His Val Asp
        35                  40                  45

Leu Ser Lys Asn Leu Leu Asp Asp Ala Thr Leu Thr Lys Leu Leu Ala
    50                  55                  60

Leu Thr Glu Glu Ser Gly Leu Arg Glu Arg Ile Asp Ala Met Phe Ala
65                  70                  75                  80

Gly Glu His Leu Asn Asn Thr Glu Asp Arg Ala Val Leu His Thr Ala
                85                  90                  95

Leu Arg Leu Pro Ala Glu Ala Asp Leu Ser Val Asp Gly Gln Asp Val
            100                 105                 110

Ala Ala Asp Val His Glu Val Leu Gly Arg Met Arg Asp Phe Ala Thr
        115                 120                 125

Ala Leu Arg Ser Gly Asn Trp Leu Gly His Thr Gly His Thr Ile Lys
    130                 135                 140

Lys Ile Val Asn Ile Gly Ile Gly Gly Ser Asp Leu Gly Pro Ala Met
145                 150                 155                 160

Ala Thr Lys Ala Leu Arg Ala Tyr Ala Thr Ala Gly Ile Ser Ala Glu
                165                 170                 175

Phe Val Ser Asn Val Asp Pro Ala Asp Leu Val Ser Val Leu Glu Asp
            180                 185                 190

Leu Asp Ala Glu Ser Thr Leu Phe Val Ile Ala Ser Lys Thr Phe Thr
        195                 200                 205

Thr Gln Glu Thr Leu Ser Asn Ala Arg Ala Ala Arg Ala Trp Leu Val
    210                 215                 220

Glu Lys Leu Gly Glu Glu Ala Val Ala Lys His Phe Val Ala Val Ser
225                 230                 235                 240

Thr Asn Ala Glu Lys Val Ala Glu Phe Gly Ile Asp Thr Asp Asn Met
                245                 250                 255

Phe Gly Phe Trp Asp Trp Val Gly Gly Arg Tyr Ser Val Asp Ser Ala
            260                 265                 270

Val Gly Leu Ser Leu Met Ala Val Ile Gly Pro Arg Asp Phe Met Arg
        275                 280                 285

Phe Leu Gly Gly Phe His Ala Met Asp Glu His Phe Arg Thr Thr Lys
    290                 295                 300

Phe Glu Glu Asn Val Pro Ile Leu Met Ala Leu Leu Gly Val Trp Tyr
305                 310                 315                 320

Ser Asp Phe Tyr Gly Ala Glu Thr His Ala Val Leu Pro Tyr Ser Glu
                325                 330                 335

Asp Leu Ser Arg Phe Ala Ala Tyr Leu Gln Gln Leu Thr Met Glu Ser
            340                 345                 350

Asn Gly Lys Ser Val His Arg Asp Gly Ser Pro Val Ser Thr Gly Thr
        355                 360                 365

Gly Glu Ile Tyr Trp Gly Glu Pro Gly Thr Asn Gly Gln His Ala Phe
    370                 375                 380

Phe Gln Leu Ile His Gln Gly Thr Arg Leu Val Pro Ala Asp Phe Ile
385                 390                 395                 400

Gly Phe Ala Arg Pro Lys Gln Asp Leu Pro Ala Gly Glu Arg Thr Met
                405                 410                 415
```

```
His Asp Leu Leu Met Ser Asn Phe Phe Ala Gln Thr Lys Val Leu Ala
            420                 425                 430

Phe Gly Lys Asn Ala Glu Glu Ile Ala Ala Glu Gly Val Ala Pro Glu
        435                 440                 445

Leu Val Asn His Lys Val Met Pro Gly Asn Arg Pro Thr Thr Thr Ile
    450                 455                 460

Leu Ala Glu Glu Leu Thr Pro Ser Ile Leu Gly Ala Leu Ile Ala Leu
465                 470                 475                 480

Tyr Glu His Ile Val Met Val Gln Gly Val Ile Trp Asp Ile Asn Ser
                485                 490                 495

Phe Asp Gln Trp Gly Val Glu Leu Gly Lys Gln Gln Ala Asn Asp Leu
            500                 505                 510

Ala Pro Ala Val Ser Gly Glu Glu Asp Val Asp Ser Gly Asp Ser Ser
        515                 520                 525

Thr Asp Ser Leu Ile Lys Trp Tyr Arg Ala Asn Arg
    530                 535                 540


<210> SEQ ID NO 15
<211> LENGTH: 1563
<212> TYPE: DNA
<213> ORGANISM: Corynebacterium glutamicum

<400> SEQUENCE: 15

atgagcgatg atcgtaaggc aattaaacgc gcactaatta gcgtgtatga caagactggc     60

ctggaggatc tagcccaggc acttcaccgc gagaacgtgg aaattgtttc caccggatcc    120

actgcggcga agattgctga gcttggtatt cctgttaccc cggttgagga gctcaccggt    180

ttccctgagt gccttgaggg ccgtgtgaag acactgcacc ctaaggttca cgctggcatc    240

ttggcggaca cccgcaagga agaccacctg cgtcagctca aggaacttga ggtcgcccca    300

ttccagcttg tcgtggtgaa cctgtaccca tttgctgaga ccgttgcgtc cggcgccgat    360

ttcgatgctt gcgttgagca gatcgacatc ggaggcccat ccatggttcg tgctgcggca    420

aagaaccacc catctgtcgc tgtggttgtt tcaccgaacc gctacgagga tgtccaggaa    480

gctttgaaga ccggtggatt ctcccgcgcg gagcgcacca agttggctgc tgaggctttc    540

cgccacaccg caacctacga tgtcaccgtt gcaacctgga tgagcgagca gctggctgcc    600

gaagattctg agactgagtt cccaggttgg atcggcacca ccaacacctt gtcccgcagc    660

ttgcgttacg gtgagaaccc tcaccagtct gcagctttgt acgtgggcaa cacccgcgga    720

cttgcacagg ctaagcagtt ccacggcaag gaaatgagct acaacaacta caccgattct    780

gatgctgcat ggcgtgcagc gtgggatcac gagcgtcctt gtgtagctat catcaagcat    840

gcaaaccctt gtggcattgc tgtttctgat gagtccatcg cagcggcaca ccgcgaggca    900

cacgcatgtg actctgtgtc cgcattcggt ggcgtcatcg cgtccaaccg tgaagtcagc    960

gttgagatgg ctaaccaggt tgcagagatc ttcactgagg tcatcatcgc tccttcctat   1020

gaagagggcg ctgtggagat cctgagccag aagaagaaca tccgtattct tcaggctgaa   1080

gcacctgtgc gtaagggctt tgagtcccgt gagatctccg gcggtctgct tgttcaggaa   1140

cgcgacttga tccacgctga gggcgacaac tccgcaaact ggactcttgc tgccggctct   1200

gctgtttctc ctgaggttct gaaggacctg gagttcgcgt ggactgcagt tcgttccgtg   1260

aagtccaacg caattctgtt ggctaagaac ggcgctaccg ttggcgttgg catgggacag   1320

gtcaaccgcg ttgactctgc tcgcttggct gtcgaccgtg caggtgcaga gcgcgctacc   1380
```

```
ggttccgttg ctgcttccga tgcgttcttc ccattcgctg acggctttga ggttctcgct   1440

gaggctggca tcactgctgt tgtgcagcct ggtggatcca ttcgcgacaa cgaggtcatt   1500

gaggcagcca acaaggctgg cgtgaccatg tacctgactg gtgcgcgaca cttcgctcac   1560

taa                                                                  1563


<210> SEQ ID NO 16
<211> LENGTH: 520
<212> TYPE: PRT
<213> ORGANISM: Corynebacterium glutamicum

<400> SEQUENCE: 16

Met Ser Asp Asp Arg Lys Ala Ile Lys Arg Ala Leu Ile Ser Val Tyr
1               5                   10                  15

Asp Lys Thr Gly Leu Glu Asp Leu Ala Gln Ala Leu His Arg Glu Asn
            20                  25                  30

Val Glu Ile Val Ser Thr Gly Ser Thr Ala Ala Lys Ile Ala Glu Leu
        35                  40                  45

Gly Ile Pro Val Thr Pro Val Glu Glu Leu Thr Gly Phe Pro Glu Cys
    50                  55                  60

Leu Glu Gly Arg Val Lys Thr Leu His Pro Lys Val His Ala Gly Ile
65                  70                  75                  80

Leu Ala Asp Thr Arg Lys Glu Asp His Leu Arg Gln Leu Lys Glu Leu
                85                  90                  95

Glu Val Ala Pro Phe Gln Leu Val Val Val Asn Leu Tyr Pro Phe Ala
            100                 105                 110

Glu Thr Val Ala Ser Gly Ala Asp Phe Asp Ala Cys Val Glu Gln Ile
        115                 120                 125

Asp Ile Gly Gly Pro Ser Met Val Arg Ala Ala Ala Lys Asn His Pro
    130                 135                 140

Ser Val Ala Val Val Val Ser Pro Asn Arg Tyr Glu Asp Val Gln Glu
145                 150                 155                 160

Ala Leu Lys Thr Gly Gly Phe Ser Arg Ala Glu Arg Thr Lys Leu Ala
                165                 170                 175

Ala Glu Ala Phe Arg His Thr Ala Thr Tyr Asp Val Thr Val Ala Thr
            180                 185                 190

Trp Met Ser Glu Gln Leu Ala Ala Glu Asp Ser Glu Thr Glu Phe Pro
        195                 200                 205

Gly Trp Ile Gly Thr Thr Asn Thr Leu Ser Arg Ser Leu Arg Tyr Gly
    210                 215                 220

Glu Asn Pro His Gln Ser Ala Ala Leu Tyr Val Gly Asn Thr Arg Gly
225                 230                 235                 240

Leu Ala Gln Ala Lys Gln Phe His Gly Lys Glu Met Ser Tyr Asn Asn
                245                 250                 255

Tyr Thr Asp Ser Asp Ala Ala Trp Arg Ala Ala Trp Asp His Glu Arg
            260                 265                 270

Pro Cys Val Ala Ile Ile Lys His Ala Asn Pro Cys Gly Ile Ala Val
        275                 280                 285

Ser Asp Glu Ser Ile Ala Ala Ala His Arg Glu Ala His Ala Cys Asp
    290                 295                 300

Ser Val Ser Ala Phe Gly Gly Val Ile Ala Ser Asn Arg Glu Val Ser
305                 310                 315                 320

Val Glu Met Ala Asn Gln Val Ala Glu Ile Phe Thr Glu Val Ile Ile
                325                 330                 335
```

```
Ala Pro Ser Tyr Glu Glu Gly Ala Val Glu Ile Leu Ser Gln Lys Lys
            340                 345                 350

Asn Ile Arg Ile Leu Gln Ala Glu Ala Pro Val Arg Lys Gly Phe Glu
        355                 360                 365

Ser Arg Glu Ile Ser Gly Gly Leu Leu Val Gln Glu Arg Asp Leu Ile
    370                 375                 380

His Ala Glu Gly Asp Asn Ser Ala Asn Trp Thr Leu Ala Ala Gly Ser
385                 390                 395                 400

Ala Val Ser Pro Glu Val Leu Lys Asp Leu Glu Phe Ala Trp Thr Ala
                405                 410                 415

Val Arg Ser Val Lys Ser Asn Ala Ile Leu Leu Ala Lys Asn Gly Ala
            420                 425                 430

Thr Val Gly Val Gly Met Gly Gln Val Asn Arg Val Asp Ser Ala Arg
        435                 440                 445

Leu Ala Val Asp Arg Ala Gly Ala Glu Arg Ala Thr Gly Ser Val Ala
    450                 455                 460

Ala Ser Asp Ala Phe Phe Pro Phe Ala Asp Gly Phe Glu Val Leu Ala
465                 470                 475                 480

Glu Ala Gly Ile Thr Ala Val Val Gln Pro Gly Gly Ser Ile Arg Asp
                485                 490                 495

Asn Glu Val Ile Glu Ala Ala Asn Lys Ala Gly Val Thr Met Tyr Leu
            500                 505                 510

Thr Gly Ala Arg His Phe Ala His
        515                 520


<210> SEQ ID NO 17
<211> LENGTH: 4385
<212> TYPE: DNA
<213> ORGANISM: Artificial Sequence
<220> FEATURE:
<223> OTHER INFORMATION: Synthesized

<400> SEQUENCE: 17

aaaggaggac catcatgagc acaaacacga ccccctccag ctggacaaac ccactgcgcg     60

acccgcagga taaacgactc ccccgcatcg ctggcccttc cggcatggtg atcttcggtg    120

tcactggcga cttggctcga aagaagctgc tccccgccat ttatgatcta gcaaaccgcg    180

gattgctgcc cccaggattc tcgttggtag gttacggccg ccgcgaatgg tccaaagaag    240

actttgaaaa atacgtacgc gatgccgcaa gtgctggtgc tcgtacggaa ttccgtgaaa    300

atgtttggga gcgcctcgcc gagggtatgg aatttgttcg cggcaacttt gatgatgatg    360

cagctttcga caacctcgct gcaacactca agcgcatcga caaaacccgc ggcaccgccg    420

gcaactgggc ttactacctg tccattccac cagattcctt cacagcggtc tgccaccagc    480

tggagcgttc cggcatggct gaatccaccg aagaagcatg gcgccgcgtg atcatcgaga    540

agcctttcgg ccacaacctc gaatccgcac acgagctcaa ccagctggtc aacgcagtct    600

tcccagaatc ttctgtgttc cgcatcgacc actatttggg caaggaaaca gttcaaaaca    660

tcctggctct gcgttttgct aaccagctgt ttgagccact gtggaactcc aactacgttg    720

accacgtcca gatcaccatg gctgaagata ttggcttggg tggacgtgct ggttactacg    780

acggcatcgg cgcagcccgc gacgtcatcc agaaccacct gatccagctc ttggctctgg    840

ttgccatgga agaaccaatt tctttcgtgc cagcgcagct gcaggcagaa aagatcaagg    900

tgctctctgc gacaaagccg tgctacccat tggataaaac ctccgctcgt ggtcagtacg    960

ctgccggttg gcagggctct gagttagtca agggacttcg cgaagaagat ggcttcaacc   1020
```

-continued

```
ctgagtccac cactgagact tttgcggctt gtaccttaga gatcacgtct cgtcgctggg   1080
ctggtgtgcc gttctacctg cgcaccggta agcgtcttgg tcgccgtgtt actgagattg   1140
ccgtggtgtt taaagacgca ccacaccagc ctttcgacgg cgacatgact gtatcccttg   1200
gccaaaacgc catcgtgatt cgcgtgcagc ctgatgaagg tgtgctcatc cgcttcggtt   1260
ccaaggttcc aggttctgcc atggaagtcc gtgacgtcaa catggacttc tcctactcag   1320
aatccttcac tgaagaatca cctgaagcat acgagcgcct cattttggat gcgctgttag   1380
atgaatccag cctcttccct accaacgagg aagtggaact gagctggaag attctggatc   1440
caattcttga agcatgggat gccgatggag aaccagagga ttacccagcg ggtacgtggg   1500
gtccaaagag cgctgatgaa atgctttccc gcaacggtca cacctggcgc aggccataat   1560
ttaggggcaa aaaatgatct ttgaacttcc ggataccacc acccagcaaa tttccaagac   1620
cctaactcga ctgcgtgaat cgggcaccca ggtcaccacc ggccgagtgc tcaccctcat   1680
cgtggtcact gactccgaaa gcgatgtcgc tgcagttacc gagtccacca atgaagcctc   1740
gcgcgagcac ccatctcgcg tgatcatttt ggtggttggc gataaaactg cagaaaacaa   1800
agttgacgca gaagtccgta tcggtggcga cgctggtgct tccgagatga tcatcatgca   1860
tctcaacgga cctgtcgctg acaagctcca gtatgtcgtc acaccactgt tgcttcctga   1920
cacccccatc gttgcttggt ggccaggtga atcaccaaag aatccttccc aggacccaat   1980
tggacgcatc gcacaacgac gcatcactga tgctttgtac gaccgtgatg acgcactaga   2040
agatcgtgtt gagaactatc acccaggtga taccgacatg acgtgggcgc gccttaccca   2100
gtggcgggga cttgttgcct cctcattgga tcacccacca cacagcgaaa tcacttccgt   2160
gaggctgacc ggtgcaagcg gcagtacctc ggtggatttg gctgcaggct ggttggcgcg   2220
gaggctgaaa gtgcctgtga tccgcgaggt gacagatgct cccaccgtgc caaccgatga   2280
gtttggtact ccactgctgg ctatccagcg cctggagatc gttcgcacca ccggctcgat   2340
catcatcacc atctatgacg ctcataccct tcaggtagag atgccggaat ccggcaatgc   2400
cccatcgctg gtggctattg gtcgtcgaag tgagtccgac tgcttgtctg aggagcttcg   2460
ccacatggat ccagatttgg gctaccagca cgcactatcc ggcttgtcca gcgtcaagct   2520
ggaaaccgtc taaaaaggag gatcctcatg actgctcact ggaaacaaaa ccaaaagaac   2580
ctcatgctgt tttcgggtcg tgcgcaccca gaactggcag aagctgtagc taaagagctc   2640
gacgtcaacg tcaccccaat gacggcacgc gatttcgcca acggtgaaat ctacgtccgc   2700
ttcgaggaat cagttcgtgg ctccgactgc ttcgtcctgc agtcccacac ccagcctctc   2760
aacaagtggc tcatggaaca gctgctgatg atcgacgctt tgaagcgtgg ttccgcaaag   2820
cgcatcaccg cgatcctgcc gttctaccca tatgcccgcc aggacaagaa gcaccgcggc   2880
cgcgagccaa tttctgctcg cctcatcgcc gacctcatgc tcaccgctgg cgcggaccgt   2940
atcgtgtccg tggacttgca caccgatcag atccagggct tcttcgacgg cccagtcgat   3000
cacatgcacg ccatgccgat cctcaccgat cacatcaagg aaaactacaa cctggacaac   3060
atctgcgtgg tctcccctga cgcaggtcgc gtgaaggttg cagagaagtg ggctaacacc   3120
ttgggcgatg ccccaatggc gttcgtgcac aagacccgct ccaccgaggt agcaaaccag   3180
gttgtcgcca accgcgtcgt cggtgacgtc gacggcaagg actgcgtgct tctcgacgac   3240
atgatcgaca ctggcggcac catcgccggc gctgtgggcg tcctgaagaa ggctggcgca   3300
aagtcagtcg tcatcgcctg cacccacggt gtgttctctg acccagcccg cgagcgcctg   3360
```

```
tctgcatgcg gtgctgaaga agtcatcacc accgacaccc tgccacagtc caccgagggc   3420

tggagcaacc tgaccgtttt gtcgatcgca ccgctgctgg ctcgcaccat caacgagatc   3480

ttcgaaaacg gttccgtcac caccctcttc gagggcgagg cctaaaaagg aggacaatca   3540

tgttgaaaat cgctgtccca aacaaaggct cgctgtccga gcgcgccatg gaaatcctcg   3600

ccgaagcagg ctacgcaggc cgtggagatt ccaaatccct caacgttttt gatgaagcaa   3660

acaacgttga attcttcttc cttcgcccta aagatatcgc catctacgtt gctggtggcc   3720

agctcgattt gggtatcacc ggccgcgacc ttgctcgcga ttcccaggct gatgtccacg   3780

aagttctttc cctcggcttc ggttcctcca ctttccgtta cgcagcacca gctgatgaag   3840

agtggagcat cgaaaagctc gacggcaagc gcatcgctac ctcttacccc aaccttgttc   3900

gcgatgacct cgcagcacgt gggctttccg ctgaggtgct ccgcctcgac ggtgcagtag   3960

aggtatccat caagcttggt gtcgcagatg ccatcgccga tgttgtatcc accggccgca   4020

cgctgcgtca gcaaggtctt gcacctttcg gcgaggttct gtgcacctct gaggctgtca   4080

ttgttggccg caaggatgaa aaggtcaccc cagagcagca gatcctgctt cgccgcatcc   4140

agggaatttt gcacgcgcag aacttcctca tgctggatta caaggtcgac cgcgacaacc   4200

tggacgctgc cactgcagta accccaggct tctccggccc agcggtatcc ccactggcac   4260

gcgacaactg ggttgctgta cgcgccatgg tgccacgcag gtcagctaac gccatcatgg   4320

ataagcttgc tggactcggc gctgaagcca tcctggcttc tgaaatccgc atcgcccgca   4380

tctag                                                               4385


<210> SEQ ID NO 18
<211> LENGTH: 1654
<212> TYPE: DNA
<213> ORGANISM: Artificial Sequence
<220> FEATURE:
<223> OTHER INFORMATION: Synthesized

<400> SEQUENCE: 18

tccgcagaaa gcacctcatt cacgatgtgc atggaggaac ggccagtcat cgcaatgcgg     60

gaacgcacct cgaccatgtg gccagaggga atagggcgag tgaagtgaat gtgaccaaca    120

taagcagtga cacagtaggt tccagaccac tgggtagcac aagcataagc agccttatcg    180

atccattcca ggactcggcc accgccaacg ccatggctac cagccatcaa aacgtcagta    240

ggggcagcca tgaaacgaag gacgacttct ggggagcggt gtggattctc acggggattc    300

tcatgcggat tatcagacat atggacactt taacggttcg tactaggctg atgcttcatg    360

aggattgatc cgctggaaac ccggcaagcc gtattggccg tcaaagactg gattgaaggg    420

gagggagacg tcgaaaagcc tggtcgtgcg gcacttgccg ccgcaactcg cctgagcgtc    480

cgactgctcg cgcaagacgc gccgggaaac agcgtggagg tgcgggtacc cccatttgtt    540

gcggtgcaat gcatagaggg gccaaaacat acacgcggca caccacccaa cgtggtggag    600

accgacgcca agacctggtt acgcttagca actgggcaaa ccacatttga tgcagaattt    660

gaaagcggaa aaattagcgc atcaggtacc cgagccaaag agattgcgga ctggttacca    720

gtggtcaaac tttagccgtt gaaaactaaa aagctgggaa ggtgaatcga atttcggggc    780

tttaaagcaa aaatgaacag cttggtctat agtggctagg taccctttttt gttttggaca    840

catgtagggt ggccgaaaca aagtaaaagg aggaccggaa tgacccaggt aaaccacccg    900

tacgatgatc tcaacgaaca ggcaccgcag gaagaatgcg gcgttttcgg cgtttgggcg    960

ccaggtgagg aagtctcgaa acttacctac tttggcctct tcgcacttca gcaccgtggt   1020
```

```
caagaagccg cgggcatcgc agtaggcgat ggcgaacaga tcctggtttt caaagatttg   1080

ggcctagtct cccaagtttt cgacgaacca attctggaat ccctccgcgg aaacatcgcc   1140

atcggacaca cccgatacac caccgccggc ggaaacacct gggaaaatgc ccagcctatg   1200

ttccgcatgg caccagatgg caccgatatc gcccttggac acaacggcaa cctgattaat   1260

tacatcgagt tgttggacaa agccaccgaa cttggcctcg tcgatcccgc caagaagcca   1320

tcagataccg atgtgctcac tggactgctc gcaagcggcg tccatgacgg aaataatctc   1380

tttgattccg ccaaggaact cctccccagc gtcaagggag cctactgcct caccttcacc   1440

gacggacaca ccctgtacgc agcgcgtgat ccattcggca tccgcccact gtccatcggc   1500

cgcctcgagc gcggctgggt agtcgcatct gaaaccgcag cgctcgacat cgtaggtgcc   1560

tcgcatgtgc gcgaggtcga accaggcgaa ctgattgcta tcgacgaatc cggcctcaag   1620

tccgcacgat tcgccgagac aacccgcaaa ggtt                               1654
```

<210> SEQ ID NO 19
<211> LENGTH: 494
<212> TYPE: PRT
<213> ORGANISM: Corynebacterium glutamicum

<400> SEQUENCE: 19

```
Met Thr Gln Val Asn His Pro Tyr Asp Asp Leu Asn Glu Gln Ala Pro
1               5                   10                  15

Gln Glu Glu Cys Gly Val Phe Gly Val Trp Ala Pro Gly Glu Glu Val
            20                  25                  30

Ser Lys Leu Thr Tyr Phe Gly Leu Phe Ala Leu Gln His Arg Gly Gln
        35                  40                  45

Glu Ala Ala Gly Ile Ala Val Gly Asp Gly Glu Gln Ile Leu Val Phe
    50                  55                  60

Lys Asp Leu Gly Leu Val Ser Gln Val Phe Asp Glu Pro Ile Leu Glu
65                  70                  75                  80

Ser Leu Arg Gly Asn Ile Ala Ile Gly His Thr Arg Tyr Thr Thr Ala
                85                  90                  95

Gly Gly Asn Thr Trp Glu Asn Ala Gln Pro Met Phe Arg Met Ala Pro
            100                 105                 110

Asp Gly Thr Asp Ile Ala Leu Gly His Asn Gly Asn Leu Ile Asn Tyr
        115                 120                 125

Ile Glu Leu Leu Asp Lys Ala Thr Glu Leu Gly Leu Val Asp Pro Ala
    130                 135                 140

Lys Lys Pro Ser Asp Thr Asp Val Leu Thr Gly Leu Leu Ala Ser Gly
145                 150                 155                 160

Val His Asp Gly Asn Asn Leu Phe Asp Ser Ala Lys Glu Leu Leu Pro
                165                 170                 175

Ser Val Lys Gly Ala Tyr Cys Leu Thr Phe Thr Asp Gly His Thr Leu
            180                 185                 190

Tyr Ala Ala Arg Asp Pro Phe Gly Ile Arg Pro Leu Ser Ile Gly Arg
        195                 200                 205

Leu Glu Arg Gly Trp Val Val Ala Ser Glu Thr Ala Ala Leu Asp Ile
    210                 215                 220

Val Gly Ala Ser His Val Arg Glu Val Glu Pro Gly Glu Leu Ile Ala
225                 230                 235                 240

Ile Asp Glu Ser Gly Leu Lys Ser Ala Arg Phe Ala Glu Thr Thr Arg
                245                 250                 255
```

```
Lys Gly Cys Val Phe Glu Tyr Val Tyr Leu Ala Arg Pro Asp Ser Val
            260                 265                 270

Ile Lys Gly Arg Asn Val Asn Glu Ala Arg Leu Glu Ile Gly Arg Lys
        275                 280                 285

Leu Ala Ala Glu Ala Pro Ala Val Gly Asp Leu Val Ile Pro Thr Pro
    290                 295                 300

Glu Ser Gly Thr Pro Ala Ala Val Gly Phe Ala Gln Ala Ser Gly Ile
305                 310                 315                 320

Pro Phe Gly Gln Gly Met Val Lys Asn Ala Tyr Val Gly Arg Thr Phe
                325                 330                 335

Ile Gln Pro Ser Asp Thr Leu Arg Gln Leu Gly Ile Arg Leu Lys Leu
            340                 345                 350

Asn Pro Leu Arg Glu Val Ile Ala Gly Lys Arg Leu Val Val Val Asp
        355                 360                 365

Asp Ser Ile Val Arg Gly Asn Thr Gln Arg Ala Val Ile Arg Met Leu
    370                 375                 380

Arg Glu Ala Gly Ala Ala Glu Val His Val Arg Ile Ala Ser Pro Pro
385                 390                 395                 400

Val Lys Trp Pro Cys Phe Tyr Gly Ile Asp Phe Ala Thr Pro Gly Glu
                405                 410                 415

Leu Ile Ala Asn Ala Val Thr Ser Asp Asn Glu Ala Glu Met Val Glu
            420                 425                 430

Ala Val Arg Ser Ala Ile Gly Ala Asp Thr Leu Gly Tyr Val Ser Ile
        435                 440                 445

Asp Ser Met Val Ala Ala Thr Glu Gln Pro Ala Asn Glu Leu Cys Ile
    450                 455                 460

Ala Cys Phe Asp Gly Lys Tyr Pro Met Gly Leu Pro Gln Gly Asn Ser
465                 470                 475                 480

Asn Ala Asp Leu Val Arg Lys Met Gln Ala Thr Ala Ser Ser
                485                 490
```

<210> SEQ ID NO 20
<211> LENGTH: 1473
<212> TYPE: DNA
<213> ORGANISM: Artificial Sequence
<220> FEATURE:
<223> OTHER INFORMATION: Synthesized

<400> SEQUENCE: 20

```
atgatggttc cgaggccgaa gaccgttaac atatctgttg tgaattctga ctctacgacc     60

accattgtcg tgctagcttc cggaacaggc accctccttc agtcactcat tgaagcgcaa    120

ggtacctatt cgatcgtggg cgttgtctct gacgtcgaat gccctgcact ttccagagcc    180

gcagatgcag gtattgatac tgcagttgtt ccgcttggaa aagatcgtgc acagtggaac    240

cacgagcttg cagacgcagt tgcagtaagc gacccagatt tggtggtctc tgcgggattc    300

atgaaaattt tgggcgaagg tttcctctca aggttcccgt cccgcatcat caacacccac    360

ccagctttat tgccttcttt ccctggtgcc cacgcggttc gcgatgcttt ggcatacggt    420

gtgaaagtgt caggttcgac agttcacctt gtcgatgctg gtgtggatac cggcccaatt    480

attgctcaac gagcagtgcc ggtagaagtg aatgatgatg aatccagcct gcatgaaaga    540

atcaagcagg ttgagcgtaa actcattgta gaagtcctga acagcgtgga attttcgcgt    600

cagggtggcg tacaactcaa ctggagaggc taatggccgt taccctgcga atgtccacag    660

ggtagctggt agtttgaaaa tcaacgccgt tgcccttagg attcagtaac tggcacattt    720
```

```
tgtaatgcgc tagatctgtg tgctcagtct tccaggctgc ttatcacagt gaaagcaaaa    780

ccaattcgtg gctgcgaaag tcgtagccac cacgaagtcc aggaggacat acaatgagcg    840

atgatcgtaa ggcaattaaa cgcgcactaa ttagcgtgta tgacaagact ggcctggagg    900

atctagccca ggcacttcac cgcgagaacg tggaaattgt ttccaccgga tccactgcgg    960

cgaagattgc tgagcttggt attcctgtta ccccggttga ggagctcacc ggtttccctg   1020

agtgccttga gggccgtgtg aagacactgc accctaaggt tcacgctggc atcttggcgg   1080

acacccgcaa ggaagaccac ctgcgtcagc tcaaggaact tgaggtcgcc ccattccagc   1140

ttgtcgtggt gaacctgtac ccatttgctg agaccgttgc gtccggcgcc gatttcgatg   1200

cttgcgttga gcagatcgac atcggaggcc catccatggt tcgtgctgcg gcaaagaacc   1260

acccatctgt cgctgtggtt gtttcaccga accgctacga ggatgtccag gaagctttga   1320

agaccggtgg attctcccgc gcggagcgca ccaagttggc tgctgaggct ttccgccaca   1380

ccgcaaccta cgatgtcacc gttgcaacct ggatgagcga gcagctggct gccgaagatt   1440

ctgagactga gttcccaggt tggatcggca cca                                 1473
```

```
<210> SEQ ID NO 21
<211> LENGTH: 27
<212> TYPE: DNA
<213> ORGANISM: Artificial Sequence
<220> FEATURE:
<223> OTHER INFORMATION: Synthesized

<400> SEQUENCE: 21

gctctagagt atcggcgtgg agttgtc                                         27


<210> SEQ ID NO 22
<211> LENGTH: 32
<212> TYPE: DNA
<213> ORGANISM: Artificial Sequence
<220> FEATURE:
<223> OTHER INFORMATION: Synthesized

<400> SEQUENCE: 22

tagtggagta gctttatttt gcgacacctg cc                                   32


<210> SEQ ID NO 23
<211> LENGTH: 34
<212> TYPE: DNA
<213> ORGANISM: Artificial Sequenct
<220> FEATURE:
<223> OTHER INFORMATION: Synthesized

<400> SEQUENCE: 23

gtcgcaaaat aaagctactc cactagtgtg atcg                                 34


<210> SEQ ID NO 24
<211> LENGTH: 30
<212> TYPE: DNA
<213> ORGANISM: Artificial Sequence
<220> FEATURE:
<223> OTHER INFORMATION: Synthesized

<400> SEQUENCE: 24

ggttcctcct ttgcgtaaga cctcactcgc                                      30


<210> SEQ ID NO 25
<211> LENGTH: 40
<212> TYPE: DNA
<213> ORGANISM: Artificial Sequence
```

<220> FEATURE:
<223> OTHER INFORMATION: Synthesized

<400> SEQUENCE: 25
gaggtcttac gcaaaggagg aaccgaatga agacatttga 40

<210> SEQ ID NO 26
<211> LENGTH: 27
<212> TYPE: DNA
<213> ORGANISM: Artificial Sequence
<220> FEATURE:
<223> OTHER INFORMATION: Synthesized

<400> SEQUENCE: 26
cgcggatccc aggatctgct gctctgg 27

<210> SEQ ID NO 27
<211> LENGTH: 27
<212> TYPE: DNA
<213> ORGANISM: Artificial Sequence
<220> FEATURE:
<223> OTHER INFORMATION: Synthesized

<400> SEQUENCE: 27
cccaagcttc gaggaaaccg ttgagga 27

<210> SEQ ID NO 28
<211> LENGTH: 35
<212> TYPE: DNA
<213> ORGANISM: Artificial Sequence
<220> FEATURE:
<223> OTHER INFORMATION: Synthesized

<400> SEQUENCE: 28
tagtggagta gctatggatt tcacctctgt gaatg 35

<210> SEQ ID NO 29
<211> LENGTH: 37
<212> TYPE: DNA
<213> ORGANISM: Artificial Sequence
<220> FEATURE:
<223> OTHER INFORMATION: Synthesized

<400> SEQUENCE: 29
tctccacttt aggtaagcta ctccactagt gtgatcg 37

<210> SEQ ID NO 30
<211> LENGTH: 30
<212> TYPE: DNA
<213> ORGANISM: Artificial Sequence
<220> FEATURE:
<223> OTHER INFORMATION: Synthesized

<400> SEQUENCE: 30
cgatcctcct ttgcgtaaga cctcactcgc 30

<210> SEQ ID NO 31
<211> LENGTH: 38
<212> TYPE: DNA
<213> ORGANISM: Artificial Sequence
<220> FEATURE:
<223> OTHER INFORMATION: Synthesized

<400> SEQUENCE: 31
gaggtcttac gcaaaggagg atcgccatgt tgaatgtc 38

<210> SEQ ID NO 32
<211> LENGTH: 27
<212> TYPE: DNA
<213> ORGANISM: Artificial Sequence
<220> FEATURE:
<223> OTHER INFORMATION: Synthesized

<400> SEQUENCE: 32
cgcggatccg gcagaggcat cagcaag 27

<210> SEQ ID NO 33
<211> LENGTH: 20
<212> TYPE: DNA
<213> ORGANISM: Artificial Sequenc
<220> FEATURE:
<223> OTHER INFORMATION: Synthesized

<400> SEQUENCE: 33
atgtgctgca aggcgattaa 20

<210> SEQ ID NO 34
<211> LENGTH: 20
<212> TYPE: DNA
<213> ORGANISM: Artificial Sequence
<220> FEATURE:
<223> OTHER INFORMATION: Synthesized

<400> SEQUENCE: 34
tatgcttccg gctcgtatgt 20

<210> SEQ ID NO 35
<211> LENGTH: 30
<212> TYPE: DNA
<213> ORGANISM: Artificial Sequence
<220> FEATURE:
<223> OTHER INFORMATION: Synthesized

<400> SEQUENCE: 35
ttttatatat gggtatcggc ggtctatgct 30

<210> SEQ ID NO 36
<211> LENGTH: 27
<212> TYPE: DNA
<213> ORGANISM: Artificial Sequenc
<220> FEATURE:
<223> OTHER INFORMATION: Synthesized

<400> SEQUENCE: 36
cgcggatcca tctacgttgc tggtggc 27

<210> SEQ ID NO 37
<211> LENGTH: 29
<212> TYPE: DNA
<213> ORGANISM: Artificial Sequence
<220> FEATURE:
<223> OTHER INFORMATION: Synthesized

<400> SEQUENCE: 37
acgggcaaca gctgctgctc tggggtgac 29

<210> SEQ ID NO 38
<211> LENGTH: 31
<212> TYPE: DNA
<213> ORGANISM: Artificial Sequence
<220> FEATURE:
<223> OTHER INFORMATION: Synthesized

<400> SEQUENCE: 38
cagagcagca gctgttgccc gtctcactgg t 31

<210> SEQ ID NO 39
<211> LENGTH: 31
<212> TYPE: DNA
<213> ORGANISM: Artificial Sequence
<220> FEATURE:
<223> OTHER INFORMATION: Synthesized

<400> SEQUENCE: 39
ggtagttaaa attacgcccc gccctgccac t 31

<210> SEQ ID NO 40
<211> LENGTH: 31
<212> TYPE: DNA
<213> ORGANISM: Artificial Sequence
<220> FEATURE:
<223> OTHER INFORMATION: Synthesized

<400> SEQUENCE: 40
gcggggcgta attttaacta cccccgaaaa t 31

<210> SEQ ID NO 41
<211> LENGTH: 27
<212> TYPE: DNA
<213> ORGANISM: Artificial Sequence
<220> FEATURE:
<223> OTHER INFORMATION: Synthesized

<400> SEQUENCE: 41
ccggaattcc gaatgaaatc tgggacg 27

<210> SEQ ID NO 42
<211> LENGTH: 29
<212> TYPE: DNA
<213> ORGANISM: Artificial Sequence
<220> FEATURE:
<223> OTHER INFORMATION: Synthesized

<400> SEQUENCE: 42
cgaagcagga tctgctgctc tggggtgac 29

<210> SEQ ID NO 43
<211> LENGTH: 31
<212> TYPE: DNA
<213> ORGANISM: Artificial Sequence
<220> FEATURE:
<223> OTHER INFORMATION: Synthesized

<400> SEQUENCE: 43
cagagcagca gatcctgctt cgccgcatcc a 31

<210> SEQ ID NO 44
<211> LENGTH: 29
<212> TYPE: DNA
<213> ORGANISM: Artificial Sequence
<220> FEATURE:
<223> OTHER INFORMATION: Synthesized

<400> SEQUENCE: 44
ggtagttaaa actagatgcg ggcgatgcg 29

<210> SEQ ID NO 45

<211> LENGTH: 31
<212> TYPE: DNA
<213> ORGANISM: Artificial Sequence
<220> FEATURE:
<223> OTHER INFORMATION: Synthesized

<400> SEQUENCE: 45
cccgcatcta gttttaacta cccccgaaaa t 31

<210> SEQ ID NO 46
<211> LENGTH: 18
<212> TYPE: DNA
<213> ORGANISM: Artificial Sequence
<220> FEATURE:
<223> OTHER INFORMATION: Synthesized

<400> SEQUENCE: 46
tcccaaacaa aggctcgc 18

<210> SEQ ID NO 47
<211> LENGTH: 18
<212> TYPE: DNA
<213> ORGANISM: Artificial Sequence
<220> FEATURE:
<223> OTHER INFORMATION: Synthesized

<400> SEQUENCE: 47
cagtcggcgg tttgctaa 18

<210> SEQ ID NO 48
<211> LENGTH: 16
<212> TYPE: DNA
<213> ORGANISM: Artificial Sequence
<220> FEATURE:
<223> OTHER INFORMATION: Synthesized

<400> SEQUENCE: 48
atgttgaaaa tcgctg 16

<210> SEQ ID NO 49
<211> LENGTH: 52
<212> TYPE: DNA
<213> ORGANISM: Artificial Sequence
<220> FEATURE:
<223> OTHER INFORMATION: Synthesized

<400> SEQUENCE: 49
ttactgcagt ggcagcgtcc aggttgtcgc ggtcgacctt gtaatccagc at 52

<210> SEQ ID NO 50
<211> LENGTH: 52
<212> TYPE: DNA
<213> ORGANISM: Artificial Sequence
<220> FEATURE:
<223> OTHER INFORMATION: Synthesized

<400> SEQUENCE: 50
acctggacgc tgccactgca gtaaccccag gcttctccgg cccagcggta tc 52

<210> SEQ ID NO 51
<211> LENGTH: 19
<212> TYPE: DNA
<213> ORGANISM: Artificial Sequence
<220> FEATURE:
<223> OTHER INFORMATION: Synthesized

<400> SEQUENCE: 51
ctagatgcgg gcgatgcgg 19

<210> SEQ ID NO 52
<211> LENGTH: 37
<212> TYPE: DNA
<213> ORGANISM: Artificial Sequence
<220> FEATURE:
<223> OTHER INFORMATION: Synthesized

<400> SEQUENCE: 52
gctctagaaa aggaggatcc tcatgactgc tcactgg 37

<210> SEQ ID NO 53
<211> LENGTH: 30
<212> TYPE: DNA
<213> ORGANISM: Artificial Sequence
<220> FEATURE:
<223> OTHER INFORMATION: Synthesized

<400> SEQUENCE: 53
ttgtcctcct ttttaggcct cgccctcgaa 30

<210> SEQ ID NO 54
<211> LENGTH: 42
<212> TYPE: DNA
<213> ORGANISM: Artificial Sequence
<220> FEATURE:
<223> OTHER INFORMATION: Synthesized

<400> SEQUENCE: 54
ggcgaggcct aaaaaggagg acaatcatgt tgaaaatcgc tg 42

<210> SEQ ID NO 55
<211> LENGTH: 28
<212> TYPE: DNA
<213> ORGANISM: Artificial Sequence
<220> FEATURE:
<223> OTHER INFORMATION: Synthesized

<400> SEQUENCE: 55
tcccccgggc tagatgcggg cgatgcgg 28

<210> SEQ ID NO 56
<211> LENGTH: 20
<212> TYPE: DNA
<213> ORGANISM: Artificial Sequence
<220> FEATURE:
<223> OTHER INFORMATION: Synthesized

<400> SEQUENCE: 56
caattaatca tcggctcgta 20

<210> SEQ ID NO 57
<211> LENGTH: 20
<212> TYPE: DNA
<213> ORGANISM: Artificial Sequence
<220> FEATURE:
<223> OTHER INFORMATION: Synthesized

<400> SEQUENCE: 57
accgcttctg cgttctgatt 20

<210> SEQ ID NO 58
<211> LENGTH: 27
<212> TYPE: DNA

<213> ORGANISM: Artificial Sequence
<220> FEATURE:
<223> OTHER INFORMATION: Synthesized

<400> SEQUENCE: 58
cgcggatccg ctctttcgga gtgacct 27

<210> SEQ ID NO 59
<211> LENGTH: 30
<212> TYPE: DNA
<213> ORGANISM: Artificial Sequence
<220> FEATURE:
<223> OTHER INFORMATION: Synthesized

<400> SEQUENCE: 59
taagcaagcg agaaaactcc tttattgtcg 30

<210> SEQ ID NO 60
<211> LENGTH: 31
<212> TYPE: DNA
<213> ORGANISM: Artificial Sequence
<220> FEATURE:
<223> OTHER INFORMATION: Synthesized

<400> SEQUENCE: 60
taaaggagtt ttctcgcttg cttatagggt c 31

<210> SEQ ID NO 61
<211> LENGTH: 29
<212> TYPE: DNA
<213> ORGANISM: Artificial Sequence
<220> FEATURE:
<223> OTHER INFORMATION: Synthesized

<400> SEQUENCE: 61
ccggaattct cgggaagcag ttagtgaaa 29

<210> SEQ ID NO 62
<211> LENGTH: 18
<212> TYPE: DNA
<213> ORGANISM: Artificial Sequence
<220> FEATURE:
<223> OTHER INFORMATION: Synthesized

<400> SEQUENCE: 62
ttgacgacgc aagagcca 18

<210> SEQ ID NO 63
<211> LENGTH: 20
<212> TYPE: DNA
<213> ORGANISM: Artificial Sequence
<220> FEATURE:
<223> OTHER INFORMATION: Synthesized

<400> SEQUENCE: 63
caccattacc gatgagaaac 20

<210> SEQ ID NO 64
<211> LENGTH: 45
<212> TYPE: DNA
<213> ORGANISM: Artificial Sequence
<220> FEATURE:
<223> OTHER INFORMATION: Synthesized

<400> SEQUENCE: 64
cccaagctta aaggaggacc atcatgagca caaacacgac cccct 45

<210> SEQ ID NO 65
<211> LENGTH: 27
<212> TYPE: DNA
<213> ORGANISM: Artificial Sequence
<220> FEATURE:
<223> OTHER INFORMATION: Synthesized

<400> SEQUENCE: 65
gctctagatt agacggtttc cagcttg 27

<210> SEQ ID NO 66
<211> LENGTH: 41
<212> TYPE: DNA
<213> ORGANISM: Artificial Sequence
<220> FEATURE:
<223> OTHER INFORMATION: Synthesized

<400> SEQUENCE: 66
tcccccggga aaggaggacc ttcatgagcg atgatcgtaa g 41

<210> SEQ ID NO 67
<211> LENGTH: 29
<212> TYPE: DNA
<213> ORGANISM: Artificial Sequence
<220> FEATURE:
<223> OTHER INFORMATION: Synthesized

<400> SEQUENCE: 67
ccggaattct tagtgagcga agtgtcgcg 29

<210> SEQ ID NO 68
<211> LENGTH: 41
<212> TYPE: DNA
<213> ORGANISM: Artificial Sequence
<220> FEATURE:
<223> OTHER INFORMATION: Synthesized

<400> SEQUENCE: 68
gctctagaaa aggaggacca tcatgagcac aaacacgacc c 41

<210> SEQ ID NO 69
<211> LENGTH: 39
<212> TYPE: DNA
<213> ORGANISM: Artificial Sequence
<220> FEATURE:
<223> OTHER INFORMATION: Synthesized

<400> SEQUENCE: 69
agtcatgagg atcctccttt ttagacggtt tccagcttg 39

<210> SEQ ID NO 70
<211> LENGTH: 48
<212> TYPE: DNA
<213> ORGANISM: Artificial Sequence
<220> FEATURE:
<223> OTHER INFORMATION: Synthesized

<400> SEQUENCE: 70
tcaagctgga aaccgtctaa aaaggaggat cctcatgact gctcactg 48

<210> SEQ ID NO 71
<211> LENGTH: 33
<212> TYPE: DNA
<213> ORGANISM: Artificial Sequence
<220> FEATURE:

<223> OTHER INFORMATION: Synthesized

<400> SEQUENCE: 71
tcccccgggc tagatgcggg cgatgcggat ttc 33

<210> SEQ ID NO 72
<211> LENGTH: 20
<212> TYPE: DNA
<213> ORGANISM: Artificial Sequence
<220> FEATURE:
<223> OTHER INFORMATION: Synthesized

<400> SEQUENCE: 72
caattaatca tcggctcgta 20

<210> SEQ ID NO 73
<211> LENGTH: 20
<212> TYPE: DNA
<213> ORGANISM: Artificial Sequence
<220> FEATURE:
<223> OTHER INFORMATION: Synthesized

<400> SEQUENCE: 73
accgcttctg cgttctgatt 20

<210> SEQ ID NO 74
<211> LENGTH: 27
<212> TYPE: DNA
<213> ORGANISM: Artificial Sequence
<220> FEATURE:
<223> OTHER INFORMATION: Synthesized

<400> SEQUENCE: 74
cgcggatcct ccgcagaaag cacctca 27

<210> SEQ ID NO 75
<211> LENGTH: 33
<212> TYPE: DNA
<213> ORGANISM: Artificial Sequence
<220> FEATURE:
<223> OTHER INFORMATION: Synthesized

<400> SEQUENCE: 75
tttagttttc aacggctaaa gtttgaccac tgg 33

<210> SEQ ID NO 76
<211> LENGTH: 34
<212> TYPE: DNA
<213> ORGANISM: Artificial Sequence
<220> FEATURE:
<223> OTHER INFORMATION: Synthesized

<400> SEQUENCE: 76
gtggtcaaac tttagccgtt gaaaactaaa aagc 34

<210> SEQ ID NO 77
<211> LENGTH: 33
<212> TYPE: DNA
<213> ORGANISM: Artificial Sequence
<220> FEATURE:
<223> OTHER INFORMATION: Synthesized

<400> SEQUENCE: 77
tccggtcctc cttttacttt gtttcggcca ccc 33

<210> SEQ ID NO 78
<211> LENGTH: 47
<212> TYPE: DNA
<213> ORGANISM: Artificial Sequence
<220> FEATURE:
<223> OTHER INFORMATION: Synthesized

<400> SEQUENCE: 78
ggccgaaaca aagtaaaagg aggaccggaa tgacccaggt aaaccac 47

<210> SEQ ID NO 79
<211> LENGTH: 27
<212> TYPE: DNA
<213> ORGANISM: Artificial Sequence
<220> FEATURE:
<223> OTHER INFORMATION: Synthesized

<400> SEQUENCE: 79
ccggaattca acctttgcgg gttgtct 27

<210> SEQ ID NO 80
<211> LENGTH: 27
<212> TYPE: DNA
<213> ORGANISM: Artificial Sequence
<220> FEATURE:
<223> OTHER INFORMATION: Synthesized

<400> SEQUENCE: 80
cccaagcttt ccagcaacca cctggat 27

<210> SEQ ID NO 81
<211> LENGTH: 30
<212> TYPE: DNA
<213> ORGANISM: Artificial Sequence
<220> FEATURE:
<223> OTHER INFORMATION: Synthesized

<400> SEQUENCE: 81
aattggcagc tattagcctt cctggttgtg 30

<210> SEQ ID NO 82
<211> LENGTH: 30
<212> TYPE: DNA
<213> ORGANISM: Artificial Sequence
<220> FEATURE:
<223> OTHER INFORMATION: Synthesized

<400> SEQUENCE: 82
caggaaggct aatagctgcc aattattccg 30

<210> SEQ ID NO 83
<211> LENGTH: 30
<212> TYPE: DNA
<213> ORGANISM: Artificial Sequence
<220> FEATURE:
<223> OTHER INFORMATION: Synthesized

<400> SEQUENCE: 83
ttgtcctcct ttgggtaaaa aatcctttcg 30

<210> SEQ ID NO 84
<211> LENGTH: 43
<212> TYPE: DNA
<213> ORGANISM: Artificial Sequence
<220> FEATURE:
<223> OTHER INFORMATION: Synthesized

<400> SEQUENCE: 84
gattttttac ccaaaggagg acaaccatga ctgctcactg gaa 43

<210> SEQ ID NO 85
<211> LENGTH: 27
<212> TYPE: DNA
<213> ORGANISM: Artificial Sequence
<220> FEATURE:
<223> OTHER INFORMATION: Synthesized

<400> SEQUENCE: 85
cgcggatccc gccattgggg catcgcc 27

<210> SEQ ID NO 86
<211> LENGTH: 27
<212> TYPE: DNA
<213> ORGANISM: Artificial Sequence
<220> FEATURE:
<223> OTHER INFORMATION: Synthesized

<400> SEQUENCE: 86
cccaagcttt caacgatcac tgcccag 27

<210> SEQ ID NO 87
<211> LENGTH: 29
<212> TYPE: DNA
<213> ORGANISM: Artificial Sequence
<220> FEATURE:
<223> OTHER INFORMATION: Synthesized

<400> SEQUENCE: 87
gggtaacggc cagtgtgtct tagaaaatg 29

<210> SEQ ID NO 88
<211> LENGTH: 29
<212> TYPE: DNA
<213> ORGANISM: Artificial Sequence
<220> FEATURE:
<223> OTHER INFORMATION: Synthesized

<400> SEQUENCE: 88
ctaagacaca ctggccgtta ccctgcgaa 29

<210> SEQ ID NO 89
<211> LENGTH: 30
<212> TYPE: DNA
<213> ORGANISM: Artificial Sequence
<220> FEATURE:
<223> OTHER INFORMATION: Synthesized

<400> SEQUENCE: 89
ttgtcctcct tttgtatgtc ctcctggact 30

<210> SEQ ID NO 90
<211> LENGTH: 44
<212> TYPE: DNA
<213> ORGANISM: Artificial Sequence
<220> FEATURE:
<223> OTHER INFORMATION: Synthesized

<400> SEQUENCE: 90
ggaggacata caaaaggagg acaaccttga ccaccttgac gctg 44

<210> SEQ ID NO 91
<211> LENGTH: 27
<212> TYPE: DNA
<213> ORGANISM: Artificial Sequence
<220> FEATURE:
<223> OTHER INFORMATION: Synthesized

<400> SEQUENCE: 91
cgcggatcca agcgatctca gtgttgt 27

<210> SEQ ID NO 92
<211> LENGTH: 20
<212> TYPE: DNA
<213> ORGANISM: Artificial Sequence
<220> FEATURE:
<223> OTHER INFORMATION: Synthesized

<400> SEQUENCE: 92
tgtgacccgc tacccgataa 20

<210> SEQ ID NO 93
<211> LENGTH: 18
<212> TYPE: DNA
<213> ORGANISM: Artificial Sequence
<220> FEATURE:
<223> OTHER INFORMATION: Synthesized

<400> SEQUENCE: 93
cgttaccctg cgaatgtc 18

<210> SEQ ID NO 94
<211> LENGTH: 31
<212> TYPE: DNA
<213> ORGANISM: Artificial Sequence
<220> FEATURE:
<223> OTHER INFORMATION: Synthesized

<400> SEQUENCE: 94
ctggagaggc taatggccgt taccctgcga a 31

<210> SEQ ID NO 95
<211> LENGTH: 30
<212> TYPE: DNA
<213> ORGANISM: Artificial Sequence
<220> FEATURE:
<223> OTHER INFORMATION: Synthesized

<400> SEQUENCE: 95
atcatcgctc attgtatgtc ctcctggact 30

<210> SEQ ID NO 96
<211> LENGTH: 26
<212> TYPE: DNA
<213> ORGANISM: Artificial Sequence
<220> FEATURE:
<223> OTHER INFORMATION: Synthesized

<400> SEQUENCE: 96
gctctagaat gatggttccg aggccg 26

<210> SEQ ID NO 97
<211> LENGTH: 30
<212> TYPE: DNA
<213> ORGANISM: Artificial Sequence
<220> FEATURE:
<223> OTHER INFORMATION: Synthesized

<400> SEQUENCE: 97
gggtaacggc cattagcctc tccagttgag 30

<210> SEQ ID NO 98
<211> LENGTH: 30
<212> TYPE: DNA
<213> ORGANISM: Artificial Sequence
<220> FEATURE:
<223> OTHER INFORMATION: Synthesized

<400> SEQUENCE: 98
ggaggacata caatgagcga tgatcgtaag 30

<210> SEQ ID NO 99
<211> LENGTH: 27
<212> TYPE: DNA
<213> ORGANISM: Artificial Sequence
<220> FEATURE:
<223> OTHER INFORMATION: Synthesized

<400> SEQUENCE: 99
tcccccgggt ggtgccgatc caacctg 27